(12) United States Patent
Diebold et al.

(10) Patent No.: US 10,324,019 B2
(45) Date of Patent: Jun. 18, 2019

(54) CELL SORTING USING A HIGH THROUGHPUT FLUORESCENCE FLOW CYTOMETER

(71) Applicant: BD Biosciences, San Jose, CA (US)

(72) Inventors: Eric Diebold, Los Angeles, CA (US); Keegan Owsley, Los Angeles, CA (US); Jonathan Lin, Los Angeles, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 21 days.

(21) Appl. No.: 15/462,124

(22) Filed: Mar. 17, 2017

(65) Prior Publication Data
US 2017/0268981 A1    Sep. 21, 2017

Related U.S. Application Data

(60) Provisional application No. 62/309,806, filed on Mar. 17, 2016.

(51) Int. Cl.
*G01N 21/00* (2006.01)
*G01N 15/14* (2006.01)
(Continued)

(52) U.S. Cl.
CPC ....... *G01N 15/1434* (2013.01); *G01N 15/147* (2013.01); *G01N 15/1429* (2013.01);
(Continued)

(58) Field of Classification Search
CPC .................................................. G01N 15/1434
See application file for complete search history.

(56) References Cited

U.S. PATENT DOCUMENTS 4,545,677 A * 10/1985 Chupp ............... G01N 15/1434
356/39
4,883,656 A    11/1989 Konrad et al.
(Continued)

FOREIGN PATENT DOCUMENTS

DE    102010044013 A1    5/2012
JP    11-6719 A    1/1999
(Continued)

OTHER PUBLICATIONS

Bertero et al. "Iterative image reconstruction: a point of view," Proceedings of the Interdisciplinary Workshop on Mathematical Methods in Biomedical Imaging and Intensity-Modulated Radiation Therapy (IMRT), Oct. 31, 2007, pp. 1-25. Retrieved from the Internet: URL:http://homes.dl.unimi.lt/borghesejTeachingjintelligentSystemsjDocumentsjSymbolic/07.Berteropaper.pdf.
(Continued)

*Primary Examiner* — Roy M Punnoose
(74) *Attorney, Agent, or Firm* — Khin K. Chin; Bret E. Field; Bozicevic, Field & Francis, LLP

(57) ABSTRACT

In one aspect, a method of sorting cells in a flow cytometry system is disclosed, which includes illuminating a cell with radiation having at least two optical frequencies shifted from one another by a radiofrequency to elicit fluorescent radiation from the cell, detecting the fluorescent radiation to generate temporal fluorescence data, and processing the temporal fluorescence data to arrive at a sorting decision regarding the cell without generating an image (i.e., a pixel-by-pixel image) of the cell based on the fluorescence data. In some cases, the sorting decision can be made with a latency less than about 100 microseconds. In some embodiments, the above method of sorting cells can have a sub-cellular resolution. In some embodiments, a single radiofrequency shift is employed to separate the optical
(Continued)

frequencies while in other such embodiments a plurality of different radiofrequency shifts are employed.

24 Claims, 41 Drawing Sheets

(51) Int. Cl.
　　*G01N 21/64*　　(2006.01)
　　*G01N 15/10*　　(2006.01)

(52) U.S. Cl.
　　CPC ..... *G01N 21/6402* (2013.01); *G01N 21/6428* (2013.01); *G01N 2015/1006* (2013.01); *G01N 2015/149* (2013.01); *G01N 2015/1447* (2013.01); *G01N 2021/6439* (2013.01)

(56) References Cited

U.S. PATENT DOCUMENTS

| | | | |
|---|---|---|---|
| 5,111,332 A | 5/1992 | Kuwabara et al. | |
| 5,192,870 A | 3/1993 | Batchelder et al. | |
| 5,293,213 A | 3/1994 | Klein et al. | |
| 5,296,911 A | 3/1994 | Weyrauch et al. | |
| 5,485,530 A | 1/1996 | Lakowicz et al. | |
| 5,489,977 A * | 2/1996 | Winslow | G01N 21/53 356/339 |
| 5,504,337 A | 4/1996 | Lakowicz et al. | |
| 5,968,738 A * | 10/1999 | Anderson | G01N 33/5005 435/243 |
| 6,016,196 A | 1/2000 | Mermelstein | |
| 6,057,814 A | 5/2000 | Kalt | |
| 6,236,454 B1 | 5/2001 | Almogy | |
| 6,252,669 B1 | 6/2001 | Drabarek | |
| 6,271,924 B1 | 8/2001 | Ngoi et al. | |
| 6,297,884 B1 | 10/2001 | Drabarek | |
| 6,396,069 B1 | 5/2002 | MacPherson et al. | |
| 6,592,822 B1 | 7/2003 | Chandler | |
| 6,642,018 B1 * | 11/2003 | Koller | A61K 41/00 435/173.4 |
| 6,867,899 B2 | 3/2005 | Knebel | |
| 7,400,457 B1 | 7/2008 | Cayer | |
| 7,630,063 B2 | 12/2009 | Padmanabhan et al. | |
| 7,724,426 B2 | 5/2010 | Yamashita et al. | |
| 7,889,348 B2 | 2/2011 | Tearney et al. | |
| 8,184,279 B2 | 5/2012 | Feldkhun | |
| 8,253,938 B2 | 8/2012 | Vacca et al. | |
| 9,201,011 B2 | 12/2015 | Kalkbrenner et al. | |
| 9,423,353 B2 | 8/2016 | Diebold et al. | |
| 9,784,661 B2 * | 10/2017 | Jalali | G01N 15/1459 |
| 2003/0031352 A1 | 2/2003 | Nelson et al. | |
| 2003/0226977 A1 | 12/2003 | Storz et al. | |
| 2005/0081245 A1 | 4/2005 | Arad et al. | |
| 2005/0121603 A1 | 6/2005 | Seyfried et al. | |
| 2006/0014212 A1 * | 1/2006 | Benkovic | B82Y 5/00 435/7.1 |
| 2000/8012929 | 6/2008 | Vaughan | |
| 2008/0129298 A1 | 6/2008 | Vaughan et al. | |
| 2008/0285606 A1 | 11/2008 | Kippenberg et al. | |
| 2009/0237289 A1 | 9/2009 | Stoddard | |
| 2009/0323061 A1 | 12/2009 | Novotny et al. | |
| 2010/0210952 A1 | 8/2010 | Taira et al. | |
| 2010/0301024 A1 | 12/2010 | Unrath | |
| 2011/0192991 A1 | 8/2011 | Fukumoto et al. | |
| 2011/0317910 A1 | 12/2011 | Suzuki | |
| 2012/0270306 A1 | 10/2012 | Vacca et al. | |
| 2012/0294319 A1 | 11/2012 | Maleki et al. | |
| 2012/0307244 A1 | 12/2012 | Sharpe et al. | |
| 2015/0177133 A1 | 6/2015 | Choi et al. | |
| 2016/0003741 A1 | 1/2016 | Diebold et al. | |
| 2017/0102314 A1 | 4/2017 | Diebold et al. | |
| 2017/0227444 A1 | 8/2017 | Jalai et al. | |
| 2018/0364146 A1 | 12/2018 | Jalali et al. | |

FOREIGN PATENT DOCUMENTS

| | | |
|---|---|---|
| JP | 2007285999 A | 11/2007 |
| JP | 2008-9395 A | 1/2008 |
| JP | 2009-20492 A | 1/2009 |
| JP | 2009-509684 A | 3/2009 |
| JP | 2011-158413 A | 8/2011 |
| JP | 2011-191496 A | 9/2011 |
| WO | WO 93/09423 A1 | 5/1993 |
| WO | WO 03/029882 A2 | 4/2003 |
| WO | WO 2007/041412 A1 | 4/2007 |
| WO | WO 2007/066126 A1 | 6/2007 |
| WO | WO 2009/087392 A1 | 7/2009 |
| WO | WO 2011/023593 A1 | 3/2011 |
| WO | WO 2012/127907 A1 | 9/2012 |
| WO | WO 2014/110290 A1 | 7/2014 |
| WO | WO 2014/152048 A2 | 9/2014 |
| WO | WO 2015/143041 A1 | 9/2015 |
| WO | WO 2016/054293 A1 | 4/2016 |
| WO | WO 2017066404 A1 | 4/2017 |
| WO | 2017161247 A1 | 9/2017 |

OTHER PUBLICATIONS

Diebold et al. "Digitally synthesized beat frequency multiplexing for sub-millisecond fluorescence microscopy," Nature Photonics, Oct. 2013, vol. 7, No. 10, pp. 806-810, published online Sep. 22, 2013.

Digman et al. "Fluorescence correlation spectroscopy and fluorescence cross-correlation spectroscopy," Wiley Interdisciplinary Reviews, Systems Biology and Medicine, vol. 1, No. 2, Apr. 29, 2009, pp. 273-282.

Dutta et al. "Quantitative Statistical Methods for Image Quality Assessment," Theranostics, vol. 3, No. 10, Oct. 4, 2013, pp. 741-756.

Eisenstein, M. "Fluorescence microscopy gets a frequency boost", Nature Methods, Dec. 2013, vol. 10, No. 12, p. 1149.

Fessler, J. A. "Penalized weighted least-squares image reconstruction for positron emission tomography," IEEE Trans. Medical Imaging, vol. 13, No. 2, Jun. 1994, pp. 290-300.

Hanley et al. "Fluorescence lifetime imaging in an optically sectioning programmable array microscope (PAM)", Cytometry, Part A, vol. 67A, No. 2, Jan. 1, 2005, pp. 112-118.

Hoffman, Robert A. "Pulse Width for Particle Sizing," Current Protocols in Cytometry, 50, Unit 1.23, pp. 1.23.1-1.23.17 (Oct. 2009).

Sisan et al. "Event Ordering in Live-Cell Imaging Determined from Temporal Cross-Correlation Asymmetry," Biophysical Journal, vol. 98, No. 11, Jun. 1, 2010, pp. 2432-2441.

Subramaniam et al. "Photophysics of Green and Red Fluorescent Proteins: Implications for Quantitative Microscopy", Methods in Enzymology, vol. 360, Jan. 1, 2003, pp. 178-201.

Thews et al. "Cross Talk Free Fluorescence Cross Correlation Spectroscopy in Live Cells," Biophysical Journal, vol. 89, No. 3, Sep. 30, 2005, pp. 2069-2076.

Varma et al. "Fast image reconstruction for fluorescence microscopy," AIP Advances, vol. 2, No. 3, Sep. 17, 2012, pp. 32174-32174.

Wu et al. "Frequency Division Multiplexed Multichannel High-Speed Fluorescence Confocal Microscope," Biophysical Journal, vol. 91, Sep. 2006, pp. 2290-2296.

Notification of Reasons for Refusal for Japanese patent application No. 2016-556971, dated Nov. 22, 2018, 5 pages.

\* cited by examiner

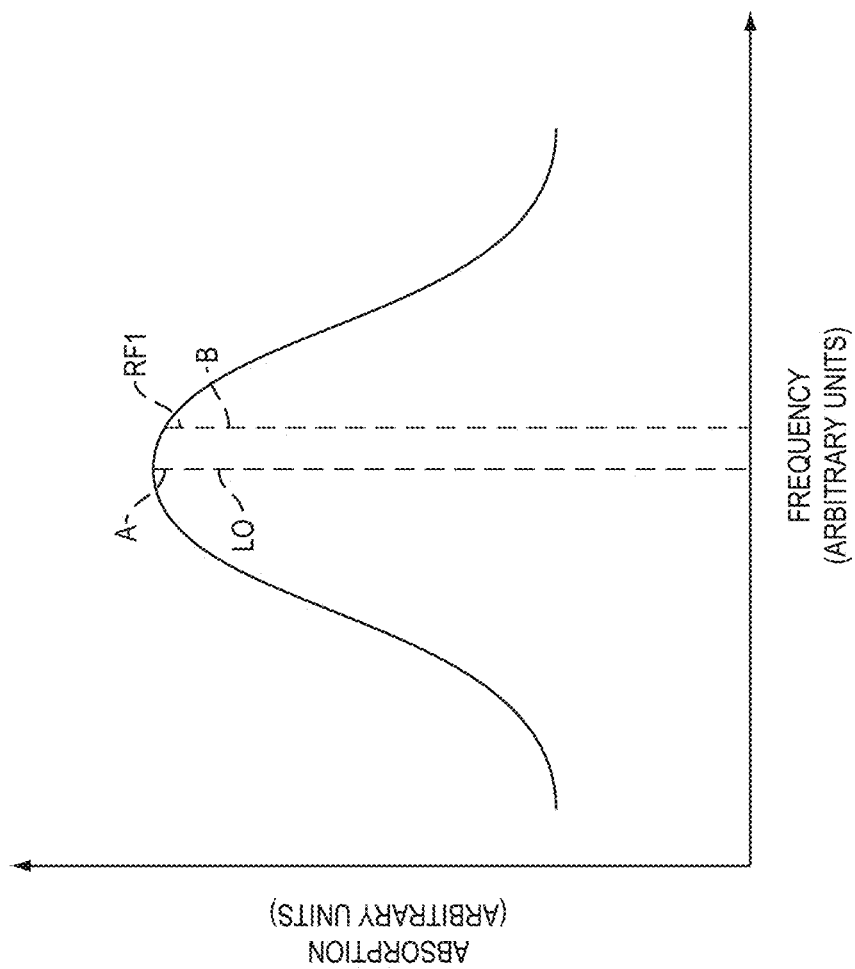

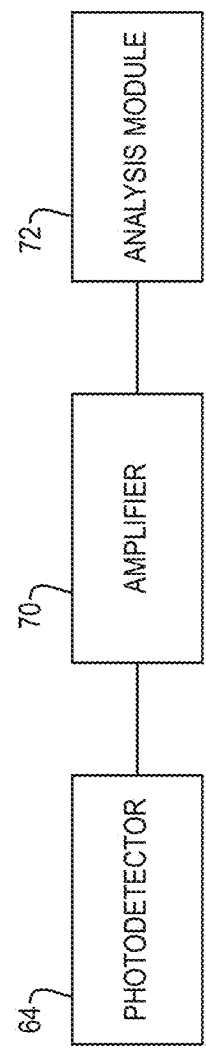

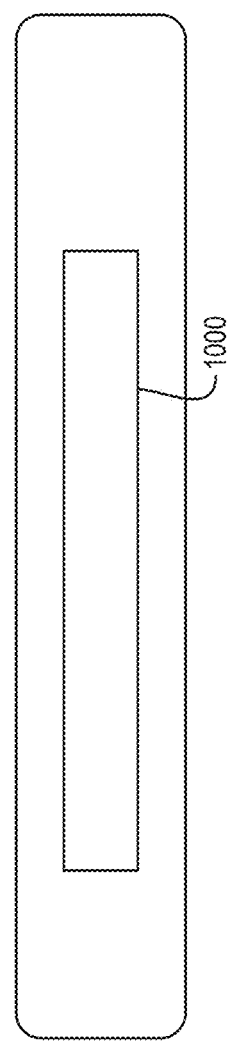

| A1 | A2 | A3 | A4 | A5 | A6 | A7 | A8 | A9 | A10 |

1700

| B1 | B2 | B3 | B4 | B5 | B6 | B7 | B8 | B9 | B10 |

1701

| A1B1 | A2B2 | A3B3 | A4B4 | A5B5 | A6B6 | A7B7 | A8B8 | A9B9 | A10B10 |

CELL SORTING USING A HIGH THROUGHPUT FLUORESCENCE FLOW CYTOMETER

RELATED APPLICATION

The present application claims priority to provisional application No. 62/309,806 titled "Cell Sorting Using A High Throughput Fluorescence Flow Cytometer," which was filed on Mar. 17, 2016 and which is herein incorporated by reference in its entirety.

GOVERNMENT RIGHTS

This invention is funded by the National Science Foundation, Grant No. NSF 1447381. The Government has certain rights in this invention.

BACKGROUND

The present invention relates generally to devices and methods for determining characteristics of particles flowing through a flow cytometer, e.g., via fluorescence analysis of samples, and more particularly to devices and methods for sorting particles, e.g., sorting cells in a flow cytometer based, for example, on their characteristics.

The isolation of subpopulations or even single cells from heterogeneous populations has a variety of applications in modern biology and biomedicine. Some conventional techniques for separating cell subpopulations include fluorescence activated cell sorting (FACS), magnetic activated cell sorting (MACS), laser capture microdissection, and DEP array sorting. These techniques, while employed routinely in cell sorting applications, present a number of shortcomings. For example, FACS, which is widely used across all areas of cell biology, lack sub-cellular resolution and hence makes sorting decisions based only on an average of a cell's parameters. Moreover, conventional sorting methods based on imaging cells are not generally capable of being used in high throughput cell separation applications due to their high latency in making sorting decisions.

Accordingly, there is a need for improved methods and systems for sorting cells, for example, in a flow cytometry system.

SUMMARY

In one aspect, a method of determining a characteristic of a particle is disclosed, which includes illuminating a particle as it flows through a flow cytometry system with a radiofrequency-modulated optical beam so as to elicit at least one radiative response from the particle, detecting the radiative response emanating from the particle to generate temporal waveform data associated with the radiative response, and processing the waveform data to obtain an estimate of at least one characteristic of the particle. In some embodiments, the processing step is performed without generating an image of the particle based on the waveform data. In some embodiments, the radiative response can be any of fluorescent or scattered radiation. In some embodiments, the processing step is sufficiently fast such that a latency associated with obtaining the estimate of at least one characteristic of the particle is equal or less than about 100 microseconds, e.g., equal to or less than about 20 microseconds.

In some embodiments, the radiofrequency-modulated optical beam includes at least two optical frequencies separated from one another by at least a radiofrequency. In such embodiments, the processing step can include analyzing at least one beat frequency associated with the at least one radiofrequency detected in said radiative response to determine the estimate of the at least one characteristic of the particle.

The above method can be employed to determine estimates of a variety of different characteristics of the particle. By way of example, the characteristic of the particle can be at least one of a dimensional size of the particle, a ratio of sizes of the particle along two different dimensions, co-localization of fluorescent radiation emitted by two or more markers associated with the particle, a degree of punctateness of the radiative response, a measure of the spatial distribution of a fluorescent radiation emanated from the particle, a measure of location or orientation of the particle, a measure of the eccentricity of the particle, a measure of the particle's similarity to a reference particle, a combination of one or more spatial Fourier components of the particle, a measure of the degree to which the particle lies in a focal point of the illuminating radiation.

In a related aspect, the estimate of the at least one characteristic of the particle can be used to arrive at a sorting decision regarding that particle.

In a related aspect, a method of determining one or more characteristics of a particle is disclosed, which includes illuminating a particle as it flows through a flow cytometry system with radiation having at least two optical frequencies shifted from one another by a radiofrequency to elicit fluorescent radiation from the particle, detecting the fluorescent radiation from the particle to generate temporal fluorescence data, and processing the temporal fluorescence data to obtain an estimate of at least one characteristic of the particle. In some embodiments, the processing step is performed without generating a fluorescence image based on the temporal fluorescence data. In some embodiments, the processing step can include analyzing one or more beat frequencies modulating the temporal fluorescence data to obtain said estimate of the at least one characteristic of the particle. In some embodiments, the processing step is sufficiently fast such that a latency associated with obtaining said estimate of at least one characteristic of the particle is less than about 100 microseconds, e.g., less than about 20 microseconds.

In some embodiments, the determined characteristic can be associated with an internal component of the particle. In some embodiments, the determined characteristic can be any of a dimensional size of the particle, a ratio of sizes of the particle along two different dimensions, co-localization of fluorescent radiation emitted by two or more markers associated with the particle, a degree of punctateness of the fluorescent radiation, a measure of the spatial distribution of the fluorescent radiation, a measure of location or orientation of the particle, a measure of the eccentricity of the particle, a measure of the particle's similarity to a reference particle, a combination of one or more spatial Fourier components of the particle, a measure of the degree to which the particle lies in a focal point of the illuminating radiation.

In some embodiments, the step of illuminating the particle includes exposing the particle to an optical radiation beam comprising at least two beamlets each having one of said at least two optical frequencies such that said beamlets illuminate at least two spatial locations within the particle. In some embodiments, the two illuminated spatial locations are partially overlapping.

In some embodiments, the particle can be stained with at least two fluorescence markers, where each marker is configured to emit fluorescent radiation in response to illumination by radiation having one of the optical frequencies. In such embodiments, the method can further include collecting and digitizing fluorescence signals emanated from these markers to generate temporal fluorescence waveforms each corresponding to one of the markers. The fluorescence waveforms can be processed to obtain a measure of co-localization of the fluorescence signals. By way of example, the processing of the fluorescence waveforms can include applying a high-pass or band-pass filter to at least one of the waveforms to generate at least one filtered waveform followed by a point-wise multiplication of the waveforms to generate at least one multiplicative waveform, integrating the multiplicative waveform to obtain an integrated value, and comparing the integrated value with a predefined threshold to obtain a measure of co-localization. In some embodiments, the determination of a measure of co-localization can include applying a high-pass or band-pass filter to at least one of the waveforms to generate at least one filtered waveform followed by a point-wise multiplication of the waveforms to generate a resultant multiplicative waveform, integrating the multiplicative waveform to obtain an integrated value, subtracting a background value from the integrated value and scaling the resultant value by intensity to generate a finalized value, and comparing the finalized value with a predefined threshold to obtain a measure of co-localization.

In some embodiments of the above method, the step of processing comprises obtaining an estimate of a lateral size of the particle along a direction substantially perpendicular to direction of particle flow in the flow cytometry system.

In some embodiments of the above method, the fluorescence waveform is employed to obtain an estimate of a lateral size of the particle by squaring the waveform, applying a bandpass filter to the squared waveform, integrating the filtered waveform, and comparing the integrated value with a predefined threshold.

In some embodiments, an estimate of the particle size in a direction parallel to the direction of particle flow in the flow cytometer can be obtained based on a temporal duration of a pulse of fluorescent radiation emanating from the particle in response to the illumination step.

In some embodiments, the estimates of the size of the particle in a direction perpendicular and in a direction parallel to the direction of particle flow can be used to obtain an estimate of the aspect ratio of the particle.

The above methods can be applied to a variety of different particles. By way of example, the particle can be any of a cell, a small organism (e.g., the nematode c. elegan), a bead, a microparticle, a nanoparticle, a viral particle, a bacterium, an exosome, or a pharmaceutical product. In some embodiments, the particle can be a mammalian cell, e.g., a diseased cell.

In a related aspect, the estimate of the at least one characteristic of the particle can be used to arrive at a sorting decision regarding that particle, as discussed in more detail below.

In a related aspect, a method of determining a characteristic of a particle is disclosed, which includes illuminating a particle with a radiofrequency-modulated optical beam so as to elicit any of fluorescent and scattered radiation from the particle, detecting fluorescent or scattered radiation emanating from the particle to generate temporal fluorescence or scattering waveform data, and processing any of the fluorescence and scattering data to obtain an estimate of at least one characteristic of the particle. In some embodiments, the processing step can be formed without generating an image of the particle based on the temporal fluorescence or scattering waveform data. In some such embodiments, the processing step is sufficiently fast such that a latency associated with obtaining the estimate of at least one characteristic of the particle is less than about 100 microseconds, e.g., less than about 20 microseconds.

In some embodiments of the above methods, the characteristic of the particle can include at least one of a dimensional size of the particle, a ratio of sizes of the particle along two different dimensions, co-localization of fluorescent radiation emitted by two or more markers associated with the particle, a degree of punctateness of the fluorescent radiation, a measure of the spatial distribution of the fluorescent radiation, a measure of location or orientation of the particle, a measure of the eccentricity of the particle, a measure of the particle's similarity to a reference particle, a combination of one or more spatial Fourier components of the particle, a measure of the degree to which the particle lies in a focal point of the illuminating radiation.

In some embodiments, both the fluorescent and scattered radiation emanated from a particle can be detected to generate fluorescence and scattering waveform data. The fluorescence data can be used to obtain an estimate of a lateral size of the particle in a direction substantially perpendicular to direction of particle flow and the scattering waveform data can be employed to obtain an estimate of a size of the particle in a direction parallel to the direction of particle flow in said flow cytometry system.

In some embodiments, the estimates of the at least one characteristic of the particle can be used to arrive at a sorting decision with respect to that particle as the particle flows through the flow cytometer.

In a related aspect, a method for performing computer-aided flow cytometry is disclosed, which includes introducing a sample containing a plurality of particles into a flow cytometer, obtaining, from one or more flow cytometer measurements, estimates of at least one particle characteristic for said plurality of particles, where said obtaining step comprises illuminating a particle as it flows through the flow cytometer with radiation having at least two optical frequencies shifted from one another by a radiofrequency, e.g., a radiofrequency in a range of about 50 MHz to about 250 MHz, to elicit a radiative response from the particle, detecting the radiative response from the particle to generate temporal waveform data associated with the response. The method can further include processing the temporal waveform data to obtain a value of said at least one particle characteristic, such as those discussed above, by analyzing one or more beat frequencies modulating said temporal waveform data, and identifying, via a computer processor, a gate indicative of one or more of said particles having a value of said particle characteristic within a predefined range. By way of example, the radiative response can be any of fluorescent, scattered, or transmitted radiation.

In one aspect, a method of sorting cells in a flow cytometry system is disclosed, which includes illuminating a cell with radiation having at least two optical frequencies shifted from one another by a radiofrequency to elicit fluorescent radiation from the cell, detecting the fluorescent radiation to generate temporal fluorescence data, and processing the temporal fluorescence data to arrive at a sorting decision regarding the cell. In some embodiments, the sorting decision can be made without generating an image (i.e., a pixel-by-pixel image) of the cell based on the fluorescence data. In other words, while the fluorescence data can contain image data that would allow generating a pixel-by-pixel fluorescence intensity map, the method arrives at the sorting decision without generating such a map. In some cases, the sorting decision can be made with a latency less than about 100 microseconds. In some embodiments, the above method of sorting cells can have a sub-cellular resolution, e.g., the sorting decision can be based on characteristics of a component of the cell. In some embodiments in which more than two frequency-shifted optical frequencies are employed, a single radiofrequency shift is employed to separate the optical frequencies while in other such embodiments a plurality of different shifts are employed.

The processing step can include analyzing one or more beat frequencies that modulate the fluorescence data in order to arrive at the sorting decision. The beat frequencies can correspond to the differences between the frequencies of the radio-frequency shifted optical frequencies. For example, when the optical beam includes two beamlets, which interfere at an illuminated cell and have two optical frequencies separated by a radiofrequency, the beat frequency corresponds to the difference between the optical frequencies. The beat frequency is typically in the frequency range of about 1 MHz to about 250 MHz.

In some embodiments, the processing step can include operating on the fluorescence data to obtain an estimate of a characteristic of the cell and making the sorting decision based on that estimate. A variety of different characteristics of the cell can be employed. For example, the cell's characteristic can relate to a characteristic of cellular component and/or the way the cell, or a component thereof, responds to the excitation radiation. By way of example, the cell characteristic may be associated with an internal organelle of the cell, such as the size of its nucleus. Some examples of cell characteristics that can be employed include, without limitation, cell size, a ratio of sizes of the cell along different dimensions, co-localization of fluorescence radiation emitted by two or more markers associated with the cell, a ratio of the sizes of the cell's cytoplasm to its nucleus, a degree of punctateness of fluorescent radiation emitted from the cell, a measure of the spatial distribution of the fluorescent radiation, a measure of location and/or orientation of the cell, a measure of the eccentricity of the cell, a measure of the cell's similarity to a reference cell, a combination of one or more spatial Fourier components of the cell, a measure of the degree to which the cell lies in a focal point of the illuminating radiation. It should be understood that the present teachings are not limited to the enumerated characteristics, but can be utilized in connection with any suitable characteristic of the cell.

In some embodiments, the processing step is sufficiently fast such that a latency associated with arriving at the sorting decision is less than about 100 microseconds, e.g., in a range of about 10 microseconds to about 100 microseconds, or in a range of about 20 microseconds to about 80 microseconds, or in a range of about 30 microseconds to about 50 microseconds.

In some embodiments, the optical beam is configured such that an optical frequency at which each of a plurality of spatial locations within the cell is illuminated corresponds to a different one of the radiofrequency-shifted optical frequencies. By way of example, in some embodiments, the optical beam can include a plurality of angularly or spatially separated beamlets each of which has a radiofrequency shift relative to another.

In some embodiments, the cell can be stained with at least two fluorescence markers and the optical radiation is configured to elicit fluorescent radiation from those markers. The fluorescent radiation can be collected and digitized to generate temporal fluorescence waveforms (i.e., waveforms indicating fluorescence intensity as a function of time) each corresponding to one of the markers. The processing step includes operating on the waveforms to obtain a measure of co-localization of the fluorescence signals corresponding to the fluorescence markers and making the sorting decision based on the co-localization estimate. In particular, the method can include applying a high-pass or band-pass filter to at least one of the waveforms to generate at least one filtered waveform followed by a point-wise multiplication of the waveforms to generate a resultant multiplicative waveform, integrating the multiplicative waveform to obtain an integrated value, and comparing the integrated value with a predefined threshold to obtain a measure of co-localization. In some embodiments, the determination of a measure of co-localization can include applying a high-pass or band-pass filter to at least one of the waveforms to generate at least one filtered waveform followed by a point-wise multiplication of the waveforms to generate a resultant multiplicative waveform, integrating the multiplicative waveform to obtain an integrated value, subtracting a background value from the integrated value and scaling the resultant value by intensity to generate a finalized value, and comparing the finalized value with a predefined threshold to obtain a measure of co-localization. The measure of co-localization can be employed to arrive at a sorting decision with respect to the cell.

In some embodiments, the processing step includes operating on the fluorescence data to obtain an estimate of a size of the cell and making the sorting decision based on the estimated cell size. By way of example, the fluorescence data can be analyzed to obtain an estimate of the cell size in a direction of cell flow (i.e., along a direction substantially parallel to the direction of cell flow) in a flow cytometry system or a lateral size of the cell (e.g., in a direction orthogonal to the direction of cell flow). In some such embodiments, the cell size in the direction of cell flow can be estimated based on a temporal duration of a pulse of the fluorescent radiation emitted by the cell. Further, an estimate of the lateral size of the cell can be obtained by squaring the detected fluorescence data, applying a bandpass filter to the squared fluorescence data, integrating the filtered data, and comparing the filtered data with a predefined threshold. In some case, the processing step includes operating on the fluorescence data to obtain a ratio of cell size along two different dimensions and utilizing that ratio to make the sorting decision.

In some embodiments, a cell is labeled with two fluorescence markers one of which is coupled to the cell's membrane and the other to the cell's nucleus. The optical radiation applied to the cell is configured to elicit fluorescence from both markers. The fluorescence signals emitted by both markers are detected in two different channels and analyzed to obtain an estimate of a ratio of the size of the cytoplasm relative to that of the nucleus. A sorting decision regarding that cell is made based on that ratio.

In some embodiments, the method includes obtaining a Fourier transform of the fluorescence data and determining frequencies in the transform different than the radiofrequencies used to modulate the optical radiation employed to elicit fluorescence radiation from the cell. A sum of the Fourier transform values at those different frequencies can be obtained and compared with a predefined threshold to make the sorting decision. By way of example, the different frequencies can be one or more frequencies between those frequencies used to modulate the optical radiation.

In a related aspect, a method for sorting cells in a flow cytometry system is disclosed, which comprises illuminating a cell with radiation having two or more optical frequencies shifted from one another by one or more radiofrequencies to elicit fluorescent radiation from the cell, detecting the fluorescent radiation to generate temporal fluorescence data, and processing the temporal fluorescence data to arrive at a sorting decision regarding the cell with a latency equal to or less than about 100 microseconds. By way of example, the sorting decision can be made with a latency in a range of about 10 microseconds to about 100 microseconds, or in a range of about 20 microseconds to about 80 microseconds, or in a range of about 30 microseconds to about 50 microseconds.

In the above method, the processing step can include operating on the fluorescence data to obtain an estimate of at least one characteristic of the cell and making the sorting decision based on that estimate. Further, the processing step can include analyzing modulation of the fluorescence data at one or more beat frequencies associated with interference of the optical frequencies of the optical radiation so as to arrive at the sorting decision.

In another aspect, a method of sorting cells in a flow cytometry system is disclosed, which includes introducing a plurality of cells, each of which is associated with at least one fluorophore, into an optical interrogating region one at a time at a rate greater than about 1000 cells per second to illuminate each of the cells with radiofrequency-modulated optical radiation so as to elicit fluorescent radiation from the fluorophore(s). For each cell, the fluorescent radiation emitted from the cell is detected to generate a time-frequency waveform, and the waveform is processed to arrive at a sorting decision regarding the cell. The method can further include guiding the cell into one of a plurality of containers based on that sorting decision.

In another aspect, a method of sorting particles (e.g., biological particles such as cells) is disclosed, which includes illuminating a particle with a radiofrequency-modulated optical beam so as to elicit any of fluorescent and scattered radiation from the particle, detecting the fluorescent or scattered (or transmitted) radiation emanating from the particle to generate fluorescence or scattering (or transmission) waveform data, and processing any of the fluorescence and scattering (or transmission) data to make a sorting decision regarding the particle without computing an image (i.e., a pixel-by-pixel fluorescence or scatter (or transmitted) intensity map) of the particle based on the data. The optical beam can be, e.g., a laser beam. Further, the optical beam can have, in some embodiments, an optical frequency in a range of about 300 THz to about 1000 THz. By way of example, in some embodiments, the radiofrequency modulation of the optical beam can be achieved by modulating the beam at radiofrequencies in a range of about 50 MHz to about 250 MHz, e.g., in a range of about 100 MHz to about 200 MHz. Further, in some embodiments, the radiofrequency-modulated optical beam can include a plurality of angularly or spatially separated beamlets each of which has a radiofrequency shift relative to another. In the above method, the processing step can include analyzing one or more beat frequencies detected in any of the fluorescent or scattered radiation to arrive at the sorting decision. The beat frequencies can correspond to the optical frequencies of the optical radiation illuminating a particle (e.g., a cell).

In a related aspect, a system for determining a characteristic of a particle is disclosed, which includes an illumination system for illuminating a particle with radiofrequency-modulated optical radiation, a detection system for detecting any of fluorescent and scattered radiation emanating from the particle in response to said illumination to generate fluorescence or scattering data, and an analysis module in communication with said detection system for receiving said fluorescence and scattering data and processing said data to calculate an estimate of at least one characteristic of the particle. In some embodiments, the analysis module can calculate an estimate of at least one characteristic of the particle without forming an image of the particle based on said fluorescence or scattering data. By way of example, the at least one characteristic of the particle can include any of a dimensional size of the particle, a ratio of sizes of the particle along two different dimensions, co-localization of fluorescence radiation emitted by two or more markers associated with the particle, a degree of punctateness of fluorescent radiation emitted from the particle, a measure of the spatial distribution of the fluorescent radiation, a measure of location or orientation of the particle, a measure of the eccentricity of the particle, a measure of the particle's similarity to a reference particle, a combination of one or more spatial Fourier components of the particle, a measure of the degree to which the particle lies in a focal point of the illuminating radiation.

The above system can be employed to obtain an estimate of at least one characteristic of a variety of different particles. By way of example, the particle can be any of a cell, a micro-vesicle, a cellular fragment, a liposome, a bead, and a small organism. In some embodiments, the particle is a cell, and the determined characteristic is a ratio of sizes of the cell's cytoplasm and nucleus.

In some embodiments of the above system, the illumination system can include an optical beam comprising a plurality of angularly or spatially-separated beamlets having optical frequencies separated from one another by at least one radiofrequency. In some such embodiments, the illumination system can include a source for generating a laser beam, a single acousto-optic deflector (AOD) receiving said laser beam, and a radiofrequency (RF) comb generator for applying a plurality of RF drive signals to said AOD to diffract said received laser beam into said plurality of angularly-separated beamlets.

In another aspect, a system for sorting particles (e.g., biological particles) is disclosed, which includes an illumination system for illuminating a particle with radiofrequency-modulated radiation, a detection system for detecting any of fluorescent and scattered (or transmitted) radiation emanating from the particle in response to the illumination to generate fluorescence or scattering data (or transmitted data), an analysis module in communication with the detection system for receiving the fluorescence and/or scattering (or transmission) data and processing the data to arrive at a sorting decision regarding the particle without forming an image of the particle based on the fluorescence and/or scattering (or transmission) data, and an actuator capable of diverting the particles from their flow path, if needed, to separate containers based upon said sorting decision. In some embodiments, the radiofrequency-modulated radiation can be in the form of an optical beam composed of a plurality of angularly or spatially separated beamlets, each of which has a radiofrequency shift relative to another.

Further understanding of various aspects of the invention can be obtained by reference to the following detailed description in conjunction with the associated drawings, which are described briefly below.

DETAILED DESCRIPTION

The present teachings relate generally to methods and systems for determining one or more characteristics of particles, such as cells, in a flow cytometer, and using those characteristics in some embodiments for sorting the particles. In embodiments discussed below, the methods employ computer processors for their implementation. Various terms used below to describe the present teachings have their ordinary meaning in the art, unless stated otherwise. For example, the term "fluorophore" is used herein consistent with its customary meaning in the art to refer to a fluorescent chemical compound that can emit radiation in response to illumination by excitation radiation.

The terms "cytometry" and "flow cytometry" are also used consistent with their customary meanings in the art. In particular, the term "cytometry" can refer to a technique for identifying and/or sorting or otherwise analyzing cells. The term "flow cytometry" can refer to a cytometric technique in which cells present in a fluid flow can be identified, and/or sorted, or otherwise analyzed, e.g., by labeling them with fluorescent markers and detecting the fluorescent markers via radiative excitation. The terms "about" and "substantially" as used herein to denote a maximum variation of 10%, or 5%, with respect to a property including numerical values.

The teachings of the present invention for determining characteristics of particles, such as cells, and sorting the particles can be implemented in a variety of different ways. The fluorescence and/or scattering data employed for making sorting decisions can be obtained by using a variety of systems. In some embodiments, the particle is illuminated by an optical beam having a plurality of radiofrequency-shifted beamlets and the fluorescence from the particle is collected and analyzed according to the present teachings to make a sorting decision. Some examples of such systems for eliciting fluorescence data from particles in which the present teachings can be incorporated are described below followed by detailed description of methods and systems for sorting particles according to the present teachings.

Figure 1:
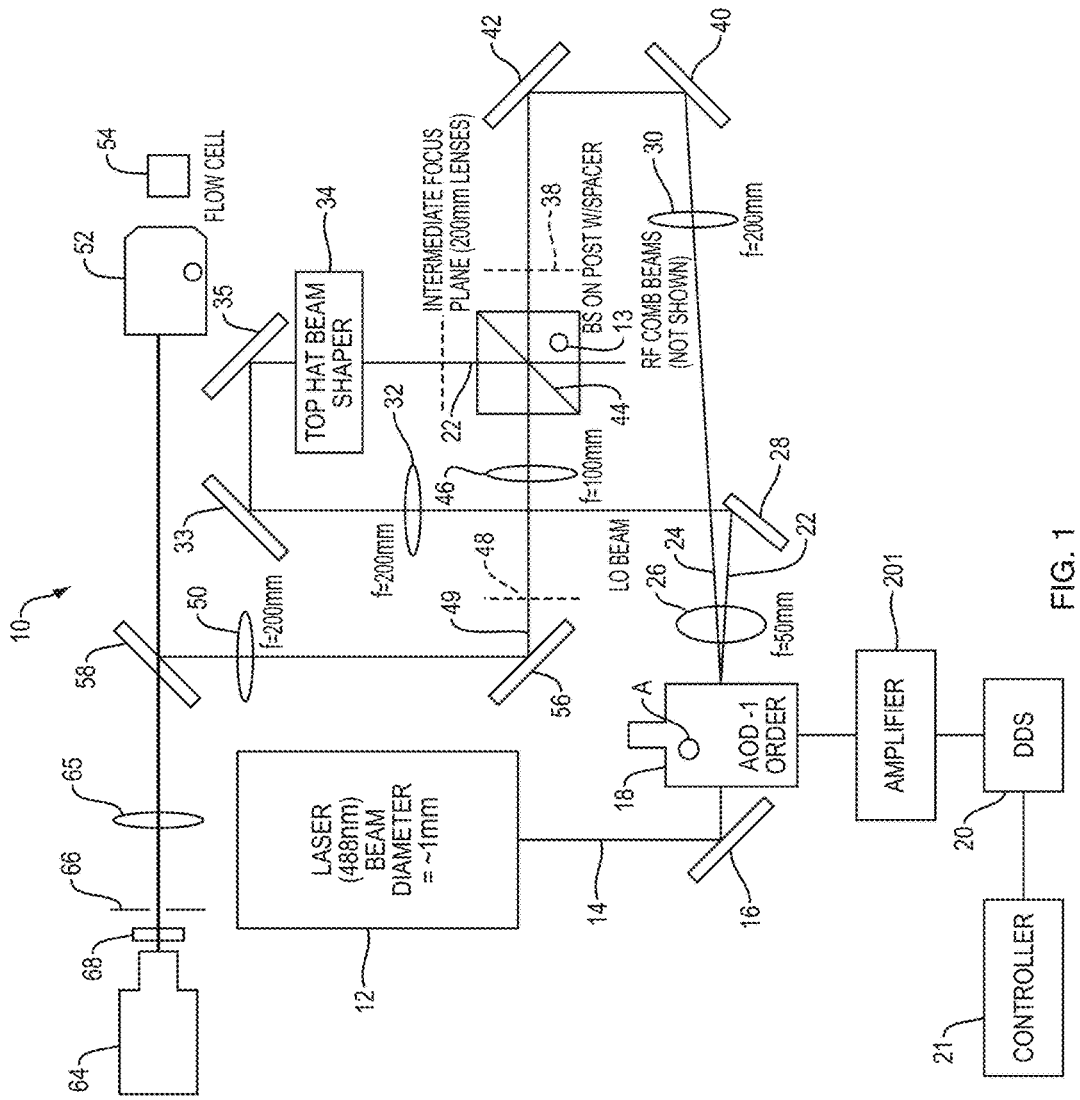
FIG. 1 schematically depicts a system in accordance with an embodiment of the invention.

By way of example, FIG. 1 schematically depicts a system 10 for performing cytometry in which the present teachings for sorting particles can be incorporated. The system 10 can be operated in three operational modes. As discussed in more detail below, in one operational mode, a sample under study can be illuminated concurrently with a plurality of excitation frequencies, each of which can be obtained, e.g., by shifting the central frequency of a laser beam. More specifically, a plurality of sample locations can be concurrently illuminated by a laser beam that is generated by mixing a reference laser beam (herein also referred to as a local oscillator beam) with a plurality of radiofrequency-shifted laser beams such that each sample location is illuminated by the reference beam and one of the radiofrequency-shifted beams to excite a fluorophore of interest at that location, if present. In some embodiments, the reference beam can itself be generated via radiofrequency shifting of a laser beam. Thus, each spatial location of the sample can be "tagged" with a different beat frequency corresponding to a difference between the frequency of the reference beam and that of one of the radiofrequency-shifted beams. In other words, the fluorescence radiation emitted by the fluorophore will spatially encode the beat frequencies. The fluorescence emission can be detected and its frequency components can be analyzed to construct a fluorescence image of the sample.

In another operational mode, a sample can be illuminated successively over a time interval by a laser beam at a plurality of excitation frequencies. In some such embodiments, the excitation frequencies can be obtained by applying a time-varying drive signal to an acousto-optic deflector (AOD), which receives a laser beam. In many embodiments, the laser beam has a frequency in the hundreds of terahertz (THz) range, e.g., in a range of about 300 THz to about 1000 THz. The drive signal applied to the AOD is typically in the radiofrequency range, e.g., in a range of about 10 MHz to about 250 MHz. The passage of the laser beam through the AOD generates a plurality of diffracted beams, each corresponding to a different diffraction order. While the zeroth diffracted beam exhibits no frequency shift relative to the frequency of the input laser beam, the higher-order diffracted beams exhibit a frequency shift relative to the frequency of the input laser beam corresponding to the frequency of the drive signal or a multiple thereof. In some embodiments, the first order diffracted beam having a frequency corresponding to the frequency of the input laser beam shifted by the drive signal is employed as the excitation beam for exciting a fluorophore of interest, if present in a sample under analysis. As the drive signal varies over time, the frequency and angular shift of the first-order diffracted beam also varies, thereby allowing the illumination of the sample at different excitation frequencies at different locations. The fluorescence emission, if any, from each illuminated location can be collected and analyzed to construct a fluorescence image of the sample.

In yet another operational mode, the system 10 can be operated to illuminate a plurality of locations of a sample concurrently by a single excitation frequency, which can be generated, e.g., by shifting the central frequency of a laser beam by a radiofrequency. For example, a horizontal extent of the sample can be illuminated by a laser beam at a single excitation frequency. The detected fluorescence radiation can be used to analyze the fluorescence content of the sample, e.g., a cell/particle.

Thus, one advantage of system 10, among others discussed below, is that it provides significant flexibility in obtaining fluorescence emission data in different modes without a need to utilize different instruments or to make any mechanical modifications to the system when switching between different operational modes.

In certain embodiments, systems include one or more light sources. In some instances, the light source is a narrow band light source, including but not limited to a narrow wavelength LED, laser or a broadband light source coupled to one or more optical bandpass filters, diffraction gratings, monochromators or any combination thereof which in combination produces a narrow band of illuminating light. In certain instances, the light source is a single wavelength laser, such as a single wavelength diode laser (e.g., a 488 nm laser). In some embodiments, the subject systems include a single light source (e.g., a laser). In other embodiments, the subject systems include two or more different light sources, such as 3 or more different light sources, such as 4 or more different light sources and including 5 or more different light sources. For example, systems may include a first light source (e.g., a laser) outputting a first wavelength and a second light source outputting a second wavelength. In other embodiments, systems include a first light source outputting a first wavelength, a second light source outputting a second wavelength and a third light source outputting a third wavelength.

Each light source may have a wavelength which ranges from 300 nm to 1000 nm, such as from 350 nm to 950 nm, such as from 400 nm to 900 nm and including from 450 nm to 850 nm. In certain embodiments, the light source has a wavelength that corresponds to an absorption maximum of one or more fluorophores (as described below). For example, the light source may output light having a wavelength that is in the range of one or more of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In certain embodiments, each light source outputs light having a wavelength that is selected from 348 nm, 355 nm, 405 nm, 407 nm, 445 nm, 488 nm, 640 nm and 652 nm.

The system 10 includes a laser radiation source 12 generating a laser beam 14. By way of example, the laser beam can have a frequency in a range of about 1000 THz to about 300 THz, corresponding to a vacuum wavelength in a range of about 300 nm to about 1000 nm. The beam diameter of the laser beam (e.g., the beam waist when a Gaussian laser beam is employed) can be, for example, in a range of about 0.1 mm to about 10 mm. Without any loss of generality, in this embodiment the laser 12 emits radiation at a wavelength of 488 nm with a beam diameter of about 1 mm.

The frequency of the laser beam can be selected based on a particular application(s) for which the system is intended. Specifically, as discussed in more detail below, the laser frequency can be suitable for exciting an electronic transition of a fluorophore of interest, e.g., via absorption of the radiation, so as to cause the fluorophore to emit fluorescence radiation at a lower frequency. A variety of laser sources can be employed. Some examples of such laser sources include, without limitation, Sapphire 488-SF, marketed by Coherent, Inc. of Santa Clara, Calif. U.S.A., Genesis MX-488-1000-STM (Coherent, Inc.), OBIS 405-LX (Coherent, Inc.), Stadus 405-250 marketed by Vortran Laser Technology, Inc. of Sacramento, Calif. U.S.A., and LQC-660-110 of Newport Corporation of Irvine, Calif. U.S.A. Without any loss of generality, in the present embodiment the laser beam is assumed to have a Gaussian intensity profile in a plane perpendicular to its propagation direction.

A mirror 16 receives the laser radiation beam 14 and directs the laser beam via reflection to an acousto-optic deflector (AOD) 18. In this embodiment, the AOD 18 is mounted on an adjustable post holder mount (A) that allows rotation of the AOD about an axis perpendicular to the propagation direction of the beam 14. A direct digital synthesizer (DDS) 20 operating under control of a controller 21 can apply one or more drive signals to the AOD 18. By way of example, in some embodiments, these drive signals can span a frequency range of about 50 MHz to about 250 MHz. For example, the drive signals applied to the AOD may range from about 55 MHz to about 255 MHz, such as from about 60 MHz to about 200 MHz, such as from about 65 MHz to about 175 MHz, such as from about 70 MHz to about 150 MHz and including from about 75 MHz to about 125 MHz. In some embodiments, the drive signals may be separated from one another by a frequency in a range of about 0.1 MHz to about 4 MHz. For example, the drive signals may be separated from one another by a frequency of from about 0.2 MHz to about 3.9 MHz, such as from about 0.3 MHz to about 3.8 MHz, such as from about 0.4 MHz to about 3.7 MHz, such as from about 0.5 MHz to about 3.6 MHz and including from about 1 MHz to about 3.5 MHz. In this embodiment, an electronic power amplifier 21' amplifies the radiofrequency signals generated by the DDS 20 for application to the AOD 18.

In the operational mode in which a sample is illuminated concurrently with a plurality of excitation frequencies, the RF comb generator 20 applies a plurality of RF drive signals concurrently to the AOD 18. By way of example, the number of simultaneously applied RF drive signals can be in a range of about 20 to about 200. The interaction of the laser beam and the drive signals results in generation of a plurality of angularly separated laser beams each having a frequency shift corresponding to one of the drive signals relative to the frequency of the laser beam generated by the laser 12. Without being limited to any particular theory, in an AOD, a piezoelectric transducer can generate radiofrequency phonons in a crystal, e.g., a quartz crystal, and the scattering of the optical photons of the laser beam by such radiofrequency phonons can result in the generation of the frequency-shifted laser beams. One of these frequency-shifted beams 22 is herein referred to as a "local oscillator" (LO) beam and the remainder of the frequency shifted beams 24 are herein referred to as "RF comb beams." The angular separation of the frequency shifted beams can be, for example, in a range of about 1 milliradians to about 100 milliradians. For example, the angular separation of the frequency shifted beams may range from 2 milliradians to about 95 milliradians, such as from 3 milliradians to about 90 milliradians, such as from 4 milliradians to about 85 milliradians, such as from 5 milliradians to about 80 milliradians and including from 10 milliradians to about 75 milliradians.

The LO and the RF comb beams pass through a lens 26, which is in this embodiment a positive lens with a focal length of about 50 mm. After passage through the lens 26, the LO laser beam is intercepted by a mirror 28, which redirects the LO beam in a different direction (in this embodiment in a direction substantially orthogonal to the original propagation direction of the LO beam). The mirror 28 is positioned relative to the RF comb beams such that these beams miss the mirror 28 and propagate to a lens 30 (which in this embodiment has a focal length of 200 mm). In this manner, the LO beam and the RF comb beams are directed along different propagation directions. The use of the pickoff mirror 28 in a manner disclosed above allows utilizing a single AOD to generate both the LO beam and the RF comb beams and combining them in a manner discussed below to generate an excitation beam for illuminating a sample. The use of a single AOD, rather than multiple AODs (e.g., two AODs, one for generating the LO beam and the other for generating the RF comb beams), simplifies the design of the system and further allows efficient use of the system in multiple distinct operational modes, as discussed in more detail below.

In some embodiments, the beam profile of the LO beam is modified before recombining with the RF comb beams. For example, the beam profile of the LO beam may be adjusted (increased or decreased) in spatial dimension, beam shape, intensity, spatial distribution of beam, or any combination thereof. In certain embodiments, the spatial dimensions of the beam profile of the LO beam are modified. For example, the beam profile may be adjusted to elongate the beam profile in one or more dimensions, such as along an axis that is orthogonal to the longitudinal axis of a flow stream. In one example according to these embodiments, the spatial dimension (e.g., in one or more dimensions) of the beam profile may be increased by 1% or more, such as by 2% or more, such as by 3% or more, such as by 5% or more, such as by 10% or more, such as by 25% or more, such as by 50% or more, such as by 75% or more, such as by 90% or more, such as by 1.5-times or more, such as by 2-times or more, such as by 3-times or more and including by 5-times or more. In another example according to these embodiments, the spatial dimension (e.g., in one or more dimensions) of the beam profile may be decreased by 1% or more, such as by 2% or more, such as by 3% or more, such as by 5% or more, such as by 10% or more, such as by 25% or more, such as by 50% or more, such as by 75% or more, such as by 90% or more, such as by 1.5-times or more, such as by 2-times or more, such as by 3-times or more and including by 5-times or more.

In other embodiments, the beam shape of the LO beam is modified. For example, the beam shape may be modified to elongate the beam profile in one or more dimensions. In certain instances, the beam shape of the LO beam is elongated in a plane perpendicular to the propagation direction of the LO beam. In certain embodiments, the shape of the LO beam profile is changed from a circular beam profile to an oval beam profile that is elongated in an axis orthogonal to the longitudinal axis of the flow stream. In other embodiments, the shape of the LO beam profile is changed from a circular beam profile to a rectangular beam profile that has a long dimension in an axis orthogonal to the longitudinal axis of the flow stream. In still other embodiments, the intensity of the LO beam is modified. For example, the intensity of the LO beam may be increased, such as by 1% or more, such as by 2% or more, such as by 3% or more, such as by 5% or more, such as by 10% or more, such as by 25% or more, such as by 50% or more, such as by 75% or more, such as by 90% or more, such as by 1.5-times or more, such as by 2-times or more, such as by 3-times or more and including by 5-times or more. In certain embodiments, the intensity of the LO beam is modified to match the intensity of the RF comb beam. For example, the LO beam may have an intensity that differs from the intensity of the RF comb beams by 10% or less, such as by 9% or less, such as by 8% or less, such as by 7% or less, such as by 6% or less, such as by 5% or less, such as by 4% or less, such as by 3% or less, such as by 2% or less, such as by 1% or less, such as by 0.01% or less and including where the intensity of the LO beam differs from the RF comb beams by 0.001% or less. In certain instances, the intensities of the LO beam and the RF comb beams are identical.

In yet other embodiments, the spatial distribution of the beam profile may also be modified. For example, the LO beam may be modified such that the intensity of the LO beam is no longer Gaussian in one or more dimensions. For example, the LO beam may be modified to have a Gaussian distribution along a first axis that is parallel to the longitudinal axis of the flow stream and non-Gaussian along a second axis that is orthogonal to the longitudinal axis of the flow stream.

Any beam shaping protocol may be employed to modify the beam profile of the LO beam, including but not limited to refractive and diffractive beam shaping protocols. In some embodiments, the LO beam is modified by a top-hat beam shaper.

In this embodiment, the LO beam propagates to another positive lens 32 (which in this embodiment has a focal length of about 200 mm). The combination of the lens 26 and the lens 32 magnifies and collimates the LO beam in order to appropriately fill the back aperture of a top-hat beam shaper 34. More specifically, the LO beam 22 passes through the lens 32 and is reflected by mirrors 33 and 35 to the top-hat beam shaper 34.

The top-hat beam shaper 34 shapes the phase front of the Gaussian LO beam to enable formation of a top-hat intensity profile. More specifically, the LO laser beam 22' exiting the top-hat beam shaper is reflected by a beam splitter 44 and is focused by lens 46 (which in this embodiment has a focal length of 100 mm) onto an intermediate image plane 48. The laser beam on the intermediate image plane 48 has a top-hat intensity profile along a horizontal direction in a plane perpendicular to the propagation direction of the beam. Similar to the AOD 18, in this embodiment, the beam splitter 44 is mounted on an adjustable post holder mount (B). In this embodiment, the top-hat beam shaper generates a top-hat beam profile in which the polarization of radiation is substantially uniform along the top-hat direction of the beam (along the horizontal direction in this embodiment).

Figure 2A:
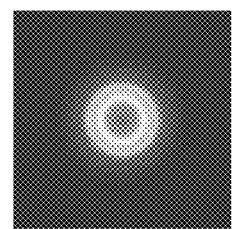
FIG. 2A is a schematic, exemplary profile of a Gaussian beam in a plane perpendicular to the beam's propagation direction.
Figure 2B:
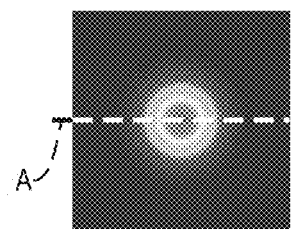
FIG. 2B is a schematic, top-hat beam profile obtained by passing the Gaussian beam shown in FIG. 2A through a top-hat beam shaper and focusing the output beam of the beam shaper, FIG. 3 schematically depicts components of an exemplary top-hat beam shaper, FIG. 4 schematically depicts cross-sectional beam profiles of a plurality of RF comb beams, FIG. 5 schematically depicts superposition of the RF comb beams depicted in FIG. 4 and an LO beam having a top-hat beam profile, FIG. 6 schematically depicts the combined beam shown in FIG. 5 illuminating a sample under analysis, FIG. 7 schematically depicts exemplary energy levels of a hypothetical fluorophore, FIG. 8 schematically depicts an absorption curve corresponding to the hypothetical fluorophore of FIG. 7, FIG. 9A schematically depicts a detection system according to an embodiment of the present teachings, which includes an optical fiber for transmission of fluorescence radiation, FIG. 9B schematically depicts another detection system according to an embodiment of the present teachings in which fluorescence radiation propagates through free space to reach a plurality of photodetectors, FIG. 9C schematically depicts a brightfield and a darkfield image generation arms for use in some embodiments of the present teachings, FIG. 9D schematically depicts a detection system for use in some embodiments of the present teachings, which includes a detection arm for generating a brightfield image and a detection arm which integrates the capabilities for the detection of excitation radiation scattered from a sample as well as fluorescence radiation emitted by the sample, FIG. 10 schematically depicts that a fluorescence signal generated by a photodetector in an embodiment of a system according to the present invention can be amplified by an amplifier and the amplified signal can be analyzed by an analysis module to construct a fluorescence image of a sample under analysis.

By way of illustration, FIG. 2A schematically depicts the Gaussian intensity profile of the LO laser beam as it enters the top-hat beam shaper. As shown schematically in FIG. 2B, on the intermediate image plane 48, the LO laser beam exhibits a beam profile that is stretched in the horizontal direction (in a direction perpendicular to the page in this illustration) and is substantially constant along each horizontal line extending through the profile, e.g., the horizontal line A, but varies vertically according to a Gaussian profile.

Figure 3:
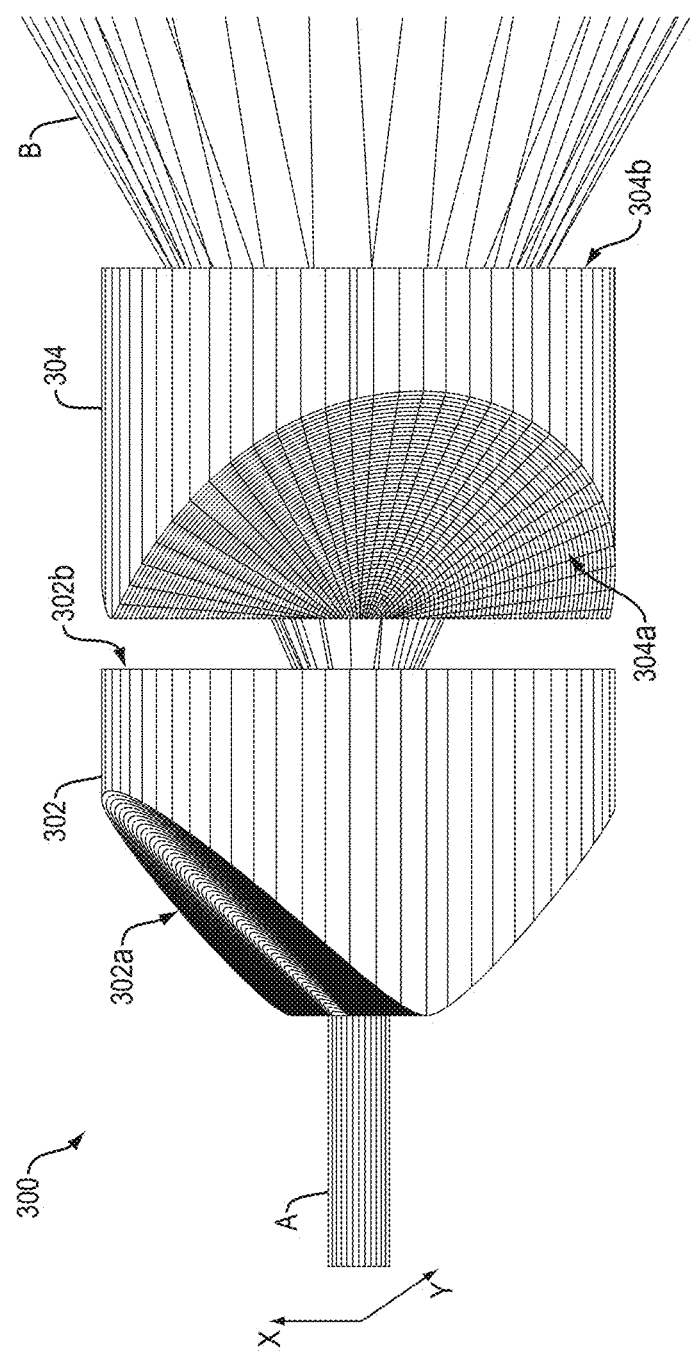

A variety of top-hat beam shapers can be employed. By way of example, refractive optical elements having an aspherical surface or diffractive optical elements can be used to produce beams with appropriate spatial phase fronts, which, after focusing by a lens, will produce a top hat profile pattern at the focal plane of the lens. Multiple form factors exist for such top-hat beam shapers, and a variety of implementations of this approach are available to create the appropriate LO beam shape at the sample in various embodiments of the present teachings. For example, U.S. Pat. No. 6,295,168 entitled "Refractive optical system that converts a laser beam to a collimated flat-top beam" and U.S. Pat. No. 7,400,457 entitled "Rectangular flat-top beam shaper," both of which are herein incorporated by reference in their entirety, disclose beam shaping systems that can be employed as the flat-top beam shaper in a system according to some embodiments of the present teachings. By way of illustration, FIG. 3 is a reproduction of FIG. 1 of U.S. Pat. No. 7,400,457 (with different reference numerals) that schematically depict a beam shaping system 300 for providing a square or a rectangular beam, which includes two orthogonally disposed acylindrical lenses 302 and 304. The first acylindrical lens 302 is for shaping an incident beam A along the X-axis and the second acylindrical lens 304 for shaping the incident beam A along the Y-axis. The two crossed acylindrical lenses are adapted to provide a resulting rectangular laser beam B having a flat-top profile along the X-axis. The input surface 302a of the acylindrical lens 302 is a convex acylindrical surface having a variable radius of curvature that is smaller in the center of the surface and increases smoothly toward both X-extremities of the lens. The second acylindrical lens 304 is similar to the first acylindrical lens but is orthogonally disposed relative to the lens 302 in order to shape the beam along the Y-axis. The profiles of input surfaces 302a/304a, and output surfaces 302b/304b of the lenses 302 and 304 can be independently selected as a function of the X and Y-profiles of the incident beam A and the desired intensity profile of the resultant rectangular beam B (See, e.g., columns 5 and 6 of the patent).

An example of a commercially available top-hat beam shaper that can be employed include, for example, DTH-1D-0.46deg-4 mm marketed by Osela, Inc. of Lachine, Canada.

As discussed in more detail below, the use of a beam shaper to stretch the LO beam along the horizontal direction provides a number of advantages. For example, it can ensure that the combination of the LO beam and the RF comb beams illuminates a plurality of sample locations with a substantially similar illumination intensity, in order to match the intensities of the LO and RF comb beams across the entirety of the sample locations, thereby creating an intensity amplitude modulation of the fluorescence signal with high modulation depth. In absence of such intensity matching, the imaging system may have a small view and may not utilize all of the frequencies (pixels) driving the AOD. As the modulation depth of the fluorescence signal plays an important role in the ability of the system to reconstruct a fluorescence image of the sample, a uniformly-high modulation depth of the excitation beat frequencies at all pixels is particularly advantageous to the operation of the system. Further, the amplitudes of electronic signals applied to the AOD for generating the RF comb beams can be adjusted by controlling the output of the direct digital synthesizer (e.g., by employing the controller 21) in order to equalize the RF comb beams such that their intensities are equal to that of the LO beam across all spatial locations in which the RF comb beams and the LO beam overlap. This feature provides an advantage in that it ensures high modulation depth of the intensity amplitude modulation of the fluorescence radiation.

Referring again to FIG. 1, the RF comb beams 24 are imaged via the combination of the lenses 26 and 30 onto an intermediate image plane 38. More specifically, the RF comb beams 24 pass through the lens 26 and miss the mirror 28 to reach the lens 30, which directs the RF comb beams via mirrors 40 and 42 to the intermediate image plane 38.

Figure 4:
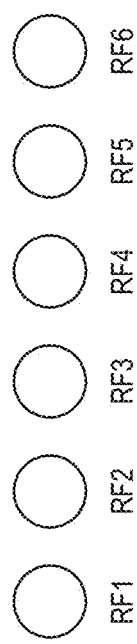

FIG. 4 schematically depicts the distribution of an exemplary number of RF comb beams in the intermediate image plane 38 (without loss of generality, the number of RF comb beams is selected to be 6 for illustration purposes (labeled as RF1, . . . , RF6), though other numbers can also be employed). As shown in FIG. 4, in the intermediate image plane 38, the RF comb beams 24 are spatially separated from one another along the horizontal direction. In other embodiments, two or more of the RF comb beams 24 may partially overlap. Thus, the combination of the lenses 26 and 30 transforms the angularly separated RF comb beams into a set of spatially separated beams that span over a horizontal extent.

Referring again to FIG. 1, as discussed above, the beam splitter 44 receives the laser beam 22' exiting the top-hat beam shaper 34 and reflects that beam to lens 46, which in turn focuses the beam on the intermediate image plane 48 in which the LO beam exhibits a top-hat beam profile. The beam splitter also receives the RF comb beams 24 from the intermediate image plane 38 and allows the passage of the RF comb beams there through. The lens 46 focuses the RF comb beams 24 onto the intermediate image plane 48 to be combined with the LO beam having a top-hat beam profile to generate a combined beam 49.

Figure 5:
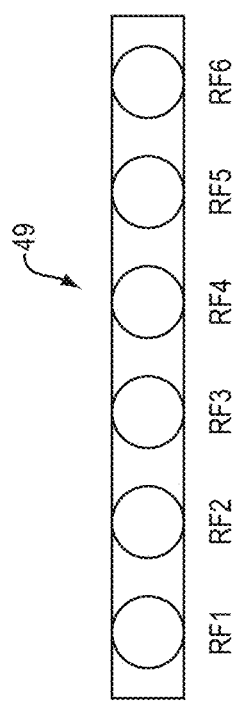

By way of illustration, FIG. 5 schematically depicts one exemplary profile of the combined beam 49 in a plane perpendicular to its propagation axis. The intensity profile of the combined beam is generated as a superposition of the intensity profile of the top-hat LO beam (shown schematically by the square) and those of the RF comb beams 24 (each shown schematically by one of the circles). As discussed in more detail below, this superposition of the LO beam and the RF comb beams provides, along a horizontal extent, a plurality of beat frequencies each corresponding to one spatial location along that horizontal extent. Upon illuminating a horizontal extent of a sample, the fluorescence radiation emitted from a location of the sample encodes, via amplitude modulation, the beat frequency associated with radiation illuminating that location.

Referring again to FIG. 1, a positive lens 50 (200-mm lens in this embodiment) and an objective lens 52, mounted in this embodiment on an adjustable post holder mount C, form a telescope for relaying the image at the intermediate plane 48 onto a sample flowing through a flow cell 54. In this embodiment, a mirror 56 reflects the combined beam 49 to the lens 50, and a dichroic mirror 58 reflects the combined light beam after its passage through the lens 50 toward the objective lens 52.

Figure 6:
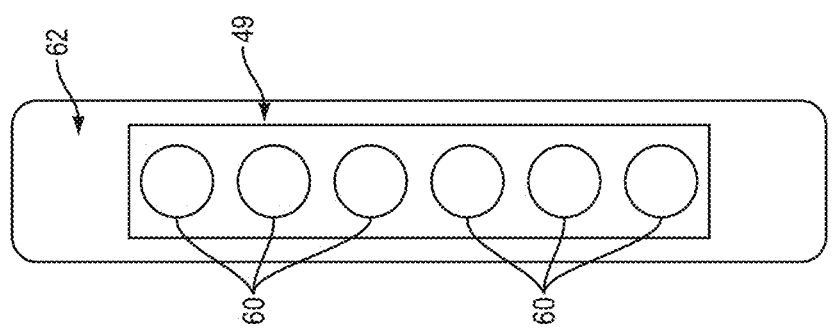

As shown schematically in FIG. 6, the combined beam 49 concurrently illuminates a plurality of spatial locations 60 of a sample 62 flowing through the flow cell 54. Thus, each location 60 is illuminated by the overlap of one of the RF comb beams with a portion of the top-hat shaped LO laser beam. At these spatial locations, the radiation will excite a fluorophore of interest in the sample, if present. More specifically, in this embodiment, the LO beam and the RF comb beams excite concurrently the fluorophore, e.g., via causing electronic transition thereof to an excited electronic state, at a plurality of sample locations 60.

In some embodiments, the sample can include a flowing fluid, in which a plurality of cells are entrained. In some cases, the cells can be labeled with one or more fluorescent markers (fluorophores). Some examples of fluorescent markers include, without limitation, fluorescent proteins (e.g., GFP, YFP, RFP), antibodies labeled with fluorophores (e.g., fluorescein isothiocyanate) (FITC), phycoerythrin (PE), allophycocyanin (APC)), nucleic acid stains (e.g., 4',6-diamidino-2-phenylindole (DAPI), SYTO16, propidium iodide (PI)), cell membrane stains (e.g., FMI-43), and cell function dyes (e.g., Fluo-4, Indo-1). In other cases, endogenous fluorophores present in cells can be employed to elicit fluorescent radiation from the cells. As discussed in more detail below, such exogenous or endogenous fluorophores undergo electronic excitation in response to the illuminating radiation and emit fluorescent radiation (typically at a lower frequency than the excitation frequency), which is collected and analyzed.

Figure 7:
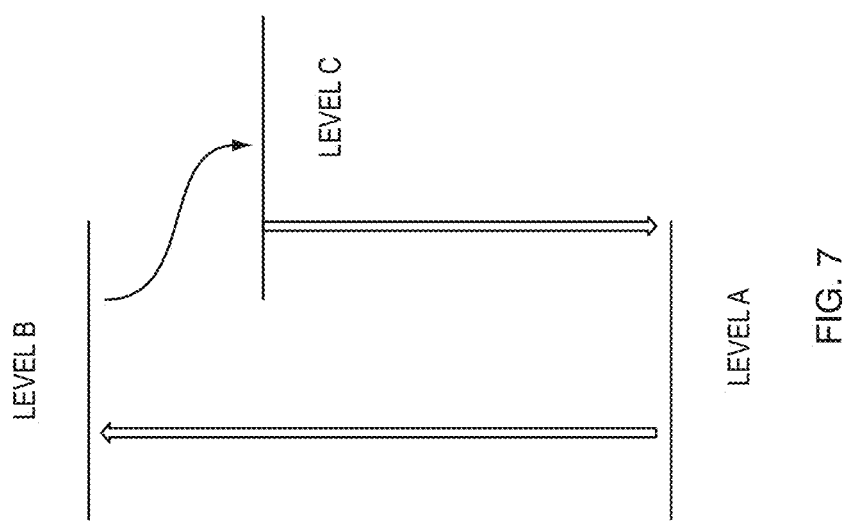

By way of illustration and without being limited to any particular theory, FIG. 7 shows hypothetical energy levels corresponding to a ground electronic state A as well as two electronic excited electronic states B and C of a fluorophore. The fluorophore can be excited from its ground electronic state (A) to the excited electronic state (B) via absorption of radiation energy. The fluorophore can then relax into the lower excited state B, e.g., via a radiation-less transition mediated by vibrational modes of the fluorophore. The fluorophore can further relax from the lower electronic state C to the ground state, via an optical transition, thereby emitting fluorescence radiation at a frequency less than that of the excitation frequency. It should be understood that this hypothetical example is provided only for illustration purposes, and not to indicate the only mechanism by which fluorescence radiation can be emitted.

In many cases, the fluorophore can absorb electromagnetic radiation over a range of frequencies to be excited from the ground state to the excited electronic state. By way of illustration, FIG. 8 shows an absorption curve for the hypothetical fluorophore discussed in connection with FIG. 7. In one implementation of an embodiment according to the present teachings the LO frequency can be selected to coincide with the frequency corresponding to the peak absorption of a fluorophore of interest. The radiofrequency-shifted beams can have frequencies separated from the peak absorption by their respective beat frequencies. Typically, these frequency separations are small in comparison to the absorption bandwidth of the fluorophore so as to avoid any degradation of the excitation frequency. By way of example and only by way of illustration, the dashed lines A and B schematically depict the frequency of the LO beam and one of the RF comb beams (the figures is not drawn to scale for ease of description). The concurrent illumination of a spatial location of the sample by both the LO laser beam and one of the depicted RF comb beams results in fluorescence radiation exhibiting an amplitude modulation at a beat frequency corresponding to a difference between the LO and the RF comb beam frequencies.

Again by way of illustration and without being limited to any particular theory, the electric field applied to the fluorophore via its concurrent illumination by the LO beam and one of the RF comb beams can be mathematically defined as follows:

$$E_{com} = E_{RF} e^{j(\omega_0 + \omega_{RF})} + E_{LO} e^{j(\omega_0 + \omega_{LO})} \qquad \text{Eq. (1)}$$

wherein, $E_{com}$ denotes the electric field of the combined beam, $E_{RF}$ denotes the amplitude of the electric field associated with one of the RF comb beams, $E_{LO}$ denotes the amplitude of the electric field associated with the LO beam, $\varphi_0$ denotes the frequency of the laser beam generated by the laser 12, $\varphi_{RF}$ denotes the frequency shift associated with the RF comb beam, and $\varphi_{LO}$ denotes the frequency shift associated with the LO beam.

The intensity of the fluorescence radiation emitted in response to the superposition of the electric fields of the LO and RF comb beams would exhibit a modulation at a beat frequency corresponding to $(\omega_{RF} - \omega_{LO})$. Hence, the fluorescence radiation emanating from each spatial location of the sample illuminated by superposition of the LO beam and one of the RF comb beams exhibits a modulation at a beat frequency corresponding to the difference between the radiofrequency shift associated with the LO beam and that associated with the RF comb beam illuminating that spatial location.

As the process of fluorescence emission requires a finite amount of time (typically 1-10 nanoseconds for common organic fluorophores), the emitted fluorescence will not exhibit a high modulation depth if the excitation beat frequency is too high. Thus, in many embodiments, the excitation beat frequencies are selected to be considerably less than $1/\tau_f$, where $\tau_f$ is the characteristic fluorescence lifetime of the fluorophore. In some instances, the excitation beat frequencies may be less than $1/\tau_f$ by 1% or more, such as by 2% or more, such as by 3% or more, such as by 5% or more, such as by 10% or more, such as by 25% or more, such as by 50% or more, such as by 75% or more, such as by 90% or more, such as by 1.5-times of more, such as by 2-times or more, such as by 3-times or more and including by 5-times or more. For example, the excitation beat frequencies may be less than $1/\tau_f$ by 0.01 MHz or more, such as by 0.05 MHz or more, such as by 0.1 MHz or more, such as by 0.5 MHz or more, such as by 1 MHz or more, such as by 5 MHz or more, such as by 10 MHz or more, such as by 25 MHz or more, such as by 50 MHz or more, such as by 100 MHz or more, such as by 250 MHz or more, such as by 500 MHz or more and including 750 MHz or more. In some embodiments, the photodetector is configured to detect light (e.g., luminescence such as fluorescence) from the irradiated sample. In some embodiments, the photodetector may include one or more detectors, such as 2 or more detectors, such as 3 or more detectors, such as 4 or more detectors, such as 5 or more detectors, such as 6 or more detectors, such as 7 or more detectors and including 8 or more detectors. Any light detecting protocol may be employed, including but not limited to active-pixel sensors (APSs), quadrant photodiodes, image sensors, change-coupled devices (CCDs), intensified charge-coupled devices (IC-CDs), light emitting diodes, photon counters, bolometers, pyroelectric detectors, photoresistors, photovoltaic cells, photodiodes, photomultiplier tubes, phototransistors, quantum dot photoconductors or photodiodes and combination thereof, among other photodetectors. In some embodiments, photodetectors of interest are configured to detect light that ranges from 350 nm to 1200 nm, such as from 450 nm to 1150 nm, such as from 500 nm to 1100 nm, such as from 550 nm to 1050 nm, such as from 500 nm to 1000 nm and including from 400 nm to 800 nm. In certain embodiments, the photodetector is configured to detect light at the emission maximum of the luminescence, such as at 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, or 805 nm.

In some embodiments, the fluorescence radiation emitted by the sample can be collected in a variety of different ways, e.g., along an optical path that is perpendicular to the propagation direction of the excitation beam. In other embodiments, the fluorescence radiation is detected in an epi-direction.

Referring again to FIG. 1, in this embodiment, the fluorescence radiation emitted by one or more fluorophores present in the illuminated sample passes through the objective lens 52 and is transmitted through the dichroic mirror 58 to reach a photodetector 64. More specifically, in this embodiment, a lens 65 focuses the fluorescent radiation transmitted through the dichroic mirror 58 onto a slit aperture 66. The fluorescent radiation that is transmitted through the slit passes through a fluorescence emission filter 68 to reach the photodetector 64. The slit aperture 66 (or an optical filter in other embodiments discussed below) disposed in front of the photodetector substantially allows the passage of the fluorescence radiation emitted from a particular plane of the sample while rejecting out-of-plane fluorescence emission. Further, the fluorescence emission filter 68, e.g., a passband filter, allows the passage of fluorescence radiation to the photodetector 64 while substantially blocking the passage of radiation at other frequencies.

The photodetector 64 has sufficient RF bandwidth to detect and transmit signals from the entire range of the beat frequencies. Some examples of suitable photodetectors include, without limitation, a photomultiplier tube, avalanche photodiode, PIN photodiode, and a hybrid photodetector, among others. By way of example, in some embodiments, a photomultiplier tube marketed by Hamamatsu Corporation can be employed (e.g., R3896, R10699, H11462). The photodetector generates a signal, e.g., an analog signal in this embodiment, in response to the detection of the received fluorescence radiation.

Figure 9A:
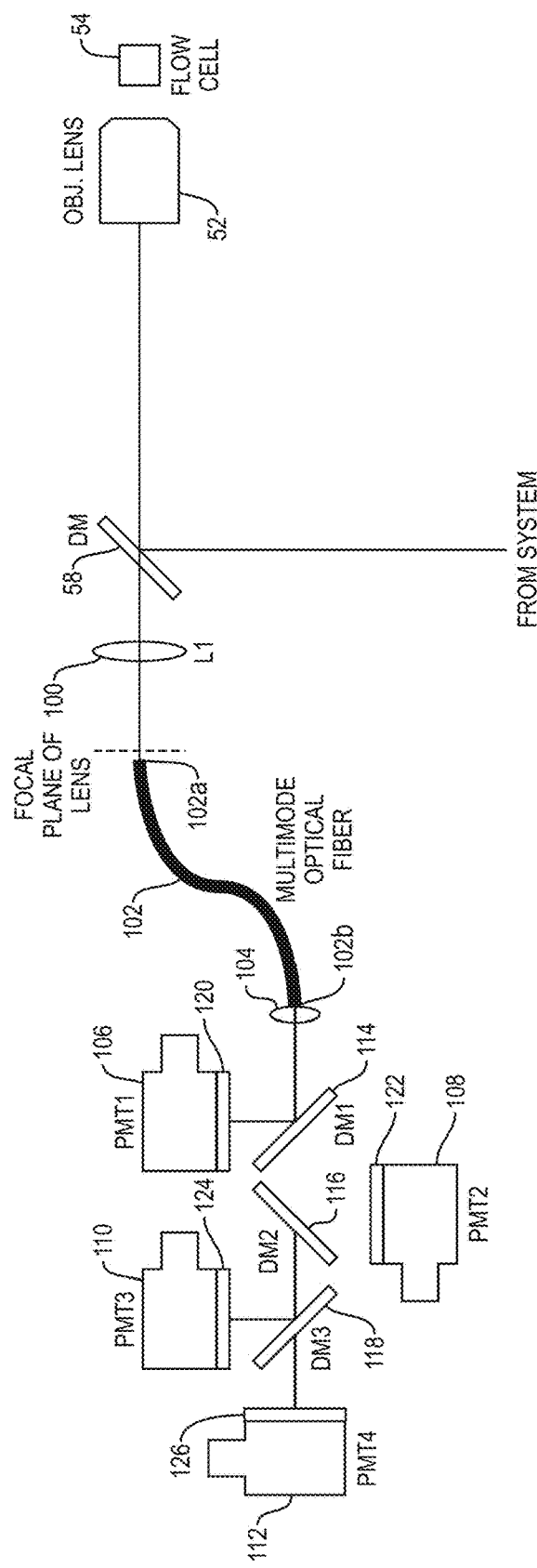

By way of another example and with reference to FIG. 9A, the fluorescence radiation emitted by the sample in response to concurrent illumination by the LO beam and the spatially separated RF comb beams passes through the objective lens 52 and the dichroic mirror 58 to be coupled via a lens 100 onto a multimode optical fiber 102, which extends from a proximal end 102*a* to a distal end 102*b*. More specifically, the proximal end 102*a* of the optical fiber 102 is positioned in proximity of the focal plane of the lens 100 so as to receive the fluorescent radiation. An outcoupling lens 104, coupled to the distal end 102*b* of the optical fiber, collimates the radiation exiting the fiber.

In many cases, the excitation radiation illuminating the sample excites multiple fluorophores (e.g., organic fluorophores) that can have broad enough radiation absorption spectra such that the excitation frequencies fall within the absorption spectra of multiple fluorophores in the sample. Each fluorophore would then emit fluorescence radiation at a different frequency. Without loss of generality and for purposes of illustration, in this embodiment, the detection system includes four photomultiplier tubes 106, 108, 110 and 112, each of which receives a portion of the collimated radiation corresponding to the fluorescence radiation emitted by one of four fluorophores excited by the excitation radiation in the illuminated sample. More specifically, a dichroic mirror 114 reflects the fluorescence radiation emitted by one of the fluorophores at a first frequency to the photomultiplier tube 106 while allowing fluorescence radiation at other frequencies to pass through. Another dichroic mirror 116 reflects the fluorescence radiation emitted by a different fluorophore at a different second frequency to the photomultiplier tube 108 while allowing the rest of the radiation containing fluorescence radiation emitted by yet another fluorophore at a third frequency to reach a third dichroic mirror 118, which reflects that fluorescence radiation to the photomultiplier tube 110. The dichroic mirror 118 allows the rest of the radiation including the fluorescence radiation emitted by a fourth fluorophore at a fourth radiation frequency to pass through to reach the photomultiplier tube 112.

A plurality of bandpass filters 120, 122, 124, and 126, each centered at one of the four fluorescence frequencies, are placed in front of the photomultiplier tubes 106, 108, 110, and 112, respectively. The signal detected by each of the photomultiplier tubes is analyzed in a manner discussed below to generate a fluorescence image at the respective fluorescence frequency. In some embodiments, rather than using multiple photodetectors, a single photodetector, e.g., a single photomultiplier tube can be used to detect fluorescence radiation, e.g., fluorescence frequency corresponding to emission from a single fluorophore.

In some embodiments, as the sample flows through the flow cell different horizontal rows of the sample are illuminated and fluorescence radiation associated with each horizontal row is detected by one or more photodetectors, such as the photomultipliers 106, 108, 110 and 112.

Figure 9B:
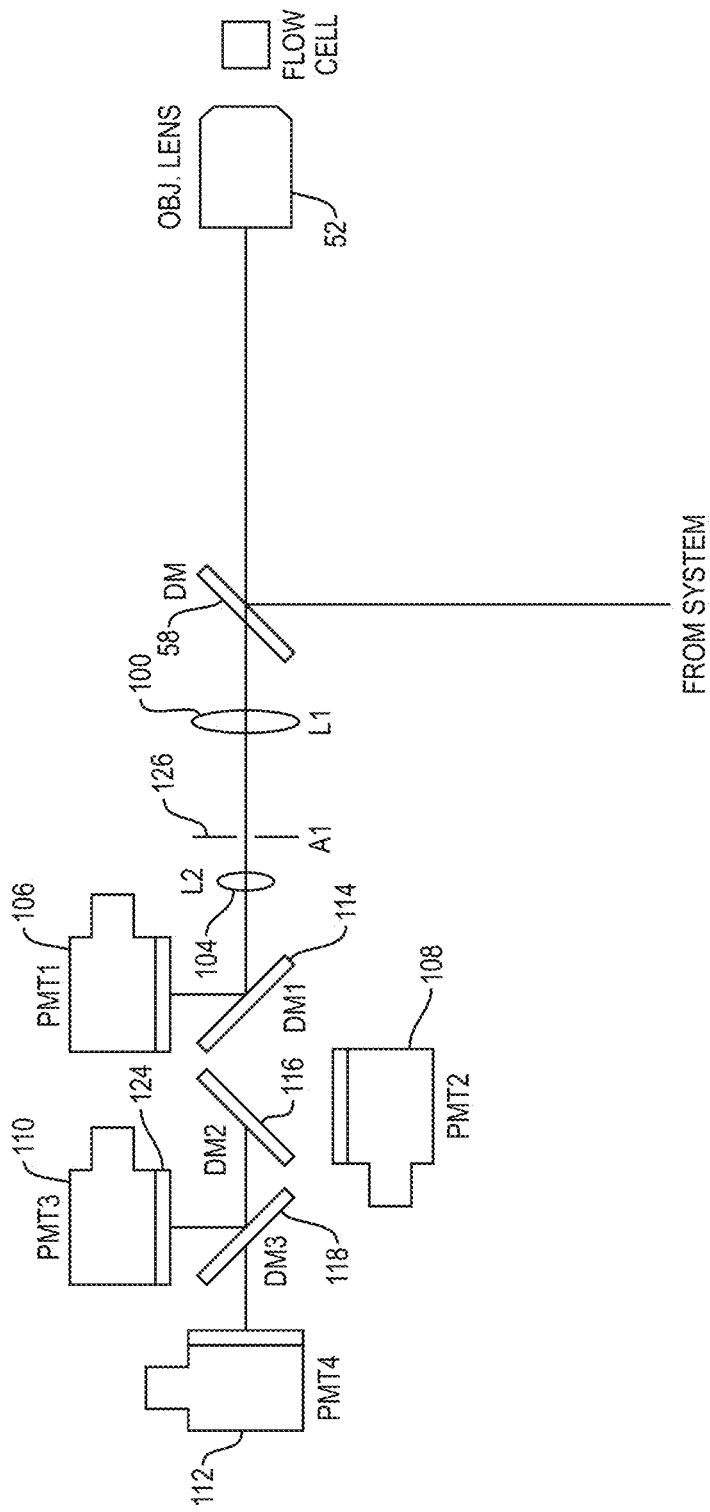

FIG. 9B schematically depicts a detection system similar to that discussed above in connection with FIG. 9A except that this detection system, rather than using an optical fiber, the fluorescence radiation containing fluorescence emission from a plurality of fluorophores passing through the dichroic mirror 58 propagates in free space to reach the photomultiplier tubes 106, 108, and 112. More specifically, the lens 100 focuses the fluorescence radiation onto an aperture 126 disposed between the lenses 100 and 104, where the aperture can reject out-of-focus radiation. The lens 104 collimates the radiation passing through the aperture, where the collimated radiation is distributed among the photomultiplier tubes in a manner discussed above in connection with FIG. 9A.

Figure 9C:
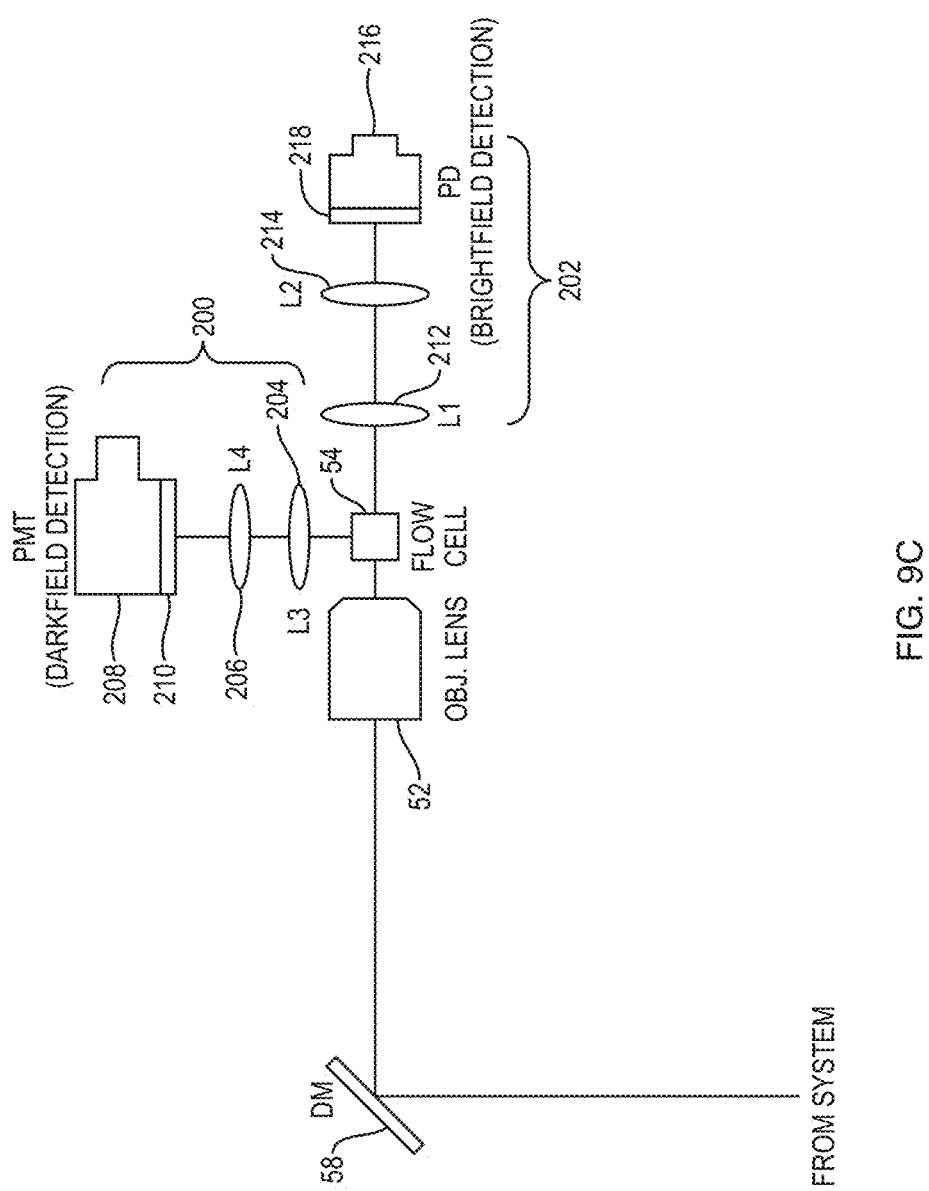

In some embodiments, the system 10 can be configured to provide a darkfield image and a brightfield image of the sample (of the flow cell in absence of the sample) using the excitation radiation. By way of example, FIG. 9C schematically depicts an embodiment of the system 10 that includes two detection arms 200 and 202 for detecting, respectively, a darkfield image and a brightfield image of the sample.

More specifically, the detection arm 200 is positioned perpendicular to the propagation of the excitation radiation so as to receive a portion of the excitation radiation that is scattered by the sample flowing through the flow cell. The detection arm 200 includes two lenses 204 and 206 that collectively direct at least a portion of the excitation radiation scattered by the sample into a solid angle subtended by the lens 204 onto a photomultiplier tube 208. More specifically, the lens 204 collimates the received scattered radiation and the lens 206 focuses the collimated scattered radiation onto the photomultiplier tube 208. In this embodiment, an appropriate bandpass filter 210 is disposed in front of the photomultiplier tube 208 to allow the passage of radiation having the desired frequency to the photomultiplier tube 208 while blocking radiation at unwanted frequencies. The output of the photomultiplier tube 208 can be processed in a manner known in the art, e.g., by an analysis module such as that discussed below to generate a darkfield image.

The detection arm 202 in turn includes two lenses 212 and 214, where the lens 212 collimates the excitation radiation exiting the flow cell in a forward direction (substantially along the propagation direction of the excitation radiation entering the flow cell 54) and the lens 214 focuses the collimated radiation onto a photodetector 216. An appropriate filter 218, e.g., a bandpass filter, disposed in front of the photodetector allows transmission of the excitation frequencies to the photodetector 216 while substantially blocking other radiation frequencies. The output of the photodetector 216 can be processed in a manner known in the art to generate a brightfield image of the flow cell.

Thus, the detection arm 200 detects the excitation radiation that is scattered by the fluid flowing through the cell, and the detection arm 202 detects the excitation radiation that is transmitted through the flow cell. When no fluid is flowing through the flow cell, the signal detected by the photomultiplier tube 208 is low and the signal detected by the photodetector 216 is high as there is little scattering of the excitation radiation passing through the flow cell and hence a large percentage, and in some cases all, of the excitation radiation is transmitted through the flow cell. In contrast, the flow of a fluid sample through the flow cell can cause the signal generated by the photomultiplier tube 208 to increase due to scattering of a portion of the excitation radiation by the sample, and the signal generated by the photodetector 216 decreases as the level of the excitation radiation transmitted through the flow cell decreases.

Figure 9D:
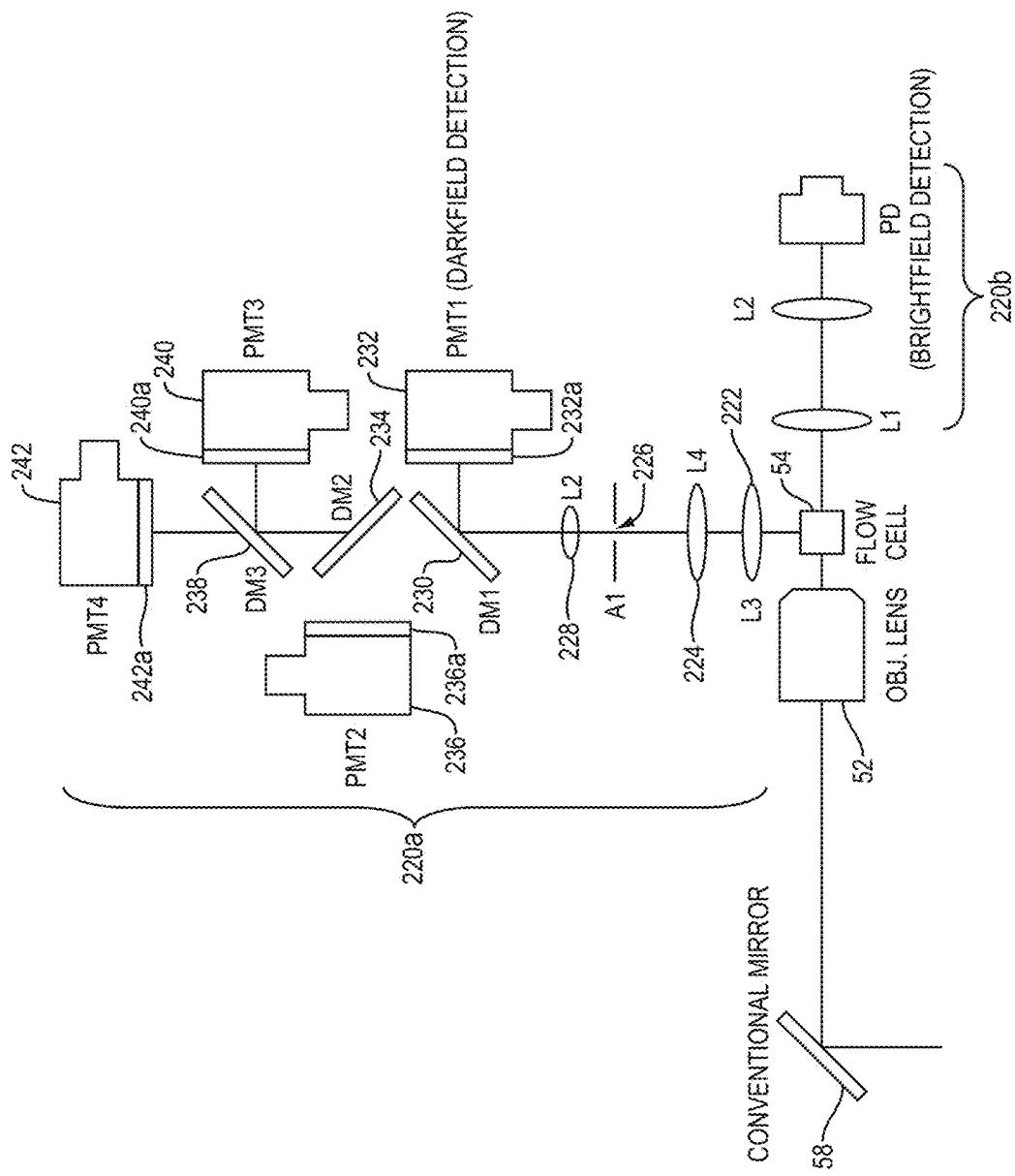

By way of further example and with reference to FIG. 9D, in one embodiment of a system according to the present teachings, a detection arm 220*a* positioned relative to the flow cell 54 in a direction substantially orthogonal to the propagation direction of the excitation radiation includes photodetectors for detecting both the fluorescence radiation emitted by a plurality of fluorophores in the sample as well as excitation radiation that is scattered by the sample. More specifically, the detection arm 220 includes lenses 222 and 224 that direct the fluorescence radiation as well as the scattered excitation radiation onto an aperture 226, which rejects unfocused radiation. A lens 228 collimates the radiation passing through the aperture. A dichroic mirror 230 reflects the portion of the radiation at the excitation frequencies onto a photomultiplier tube 232 for detection of a darkfield image while allowing fluorescence radiation to pass through. An appropriate filter 232a, e.g., a bandpass filter, disposed in front of the photomultiplier tube 232 allows the passage of radiation at excitation frequencies to the photomultiplier tube 232 while blocking unwanted radiation frequencies. Another dichroic mirror 234 reflects fluorescence radiation emitted by a fluorophore at a first frequency onto a photomultiplier tube 236 while allowing the passage of fluorescence radiation emitted by other fluorophores at other frequencies. Another dichroic mirror 238 reflects fluorescence radiation emitted by another fluorophore at a second frequency onto a photomultiplier tube 240 while allowing the passage of fluorescence radiation emitted by yet another fluorophore at a third frequency, where it is detected by the photomultiplier tube 242. Similar to the previous embodiments, a plurality of filters 236a, 240a, and 242a are disposed in front of the photomultiplier tubes 236, 240, and 242, respectively, to allow the transmission of radiation at desired frequencies while substantially blocking unwanted radiation frequencies.

With continued reference to FIG. 9D, this implementation of a system according to the present teachings further includes another detection arm 220b for generating a brightfield image, e.g., in a manner discussed in connection with FIG. 9C. More specifically, the detection arm 202 includes two lenses 212 and 214 that focus the light onto a photodetector 216 for generating a brightfield image of the excitation radiation. A filter 218, e.g., a bandpass filter, is placed in front of the photodetector 216 to allow the passage of the excitation radiation to the detector while rejecting unwanted radiation frequencies.

Referring again to FIG. 1 as well as FIG. 10, in this embodiment, a transimpedance amplifier 70 can be coupled to the output of photodetector 64 (or each of the photodetectors discussed in connection with FIGS. 9A-9D) to amplify the signal generated by the photodetector. A data analysis unit 72 (herein also referred to as an analysis module or an analyzer) receives the amplified signal and analyzes the signal to generate a fluorescence image of the sample. The data analysis unit 72 can be implemented in hardware, firmware, and/or software. By way of example, a method for analyzing the detected fluorescence data can be stored in a read-only-memory (ROM) unit of the analysis module to be accessed under the control of a processor to analyze the received fluorescence signal.

As discussed in more detail below, the analysis method determines the frequency components of the time-varying photodetector's output and constructs a fluorescence image of the sample based on those frequency components. A variety of methods for determining the frequency content of the photodetector's output can be employed. Some examples of such suitable methods include, without limitation, Fourier transform, lock-in detection, filtering, I/Q demodulation, homodyne detection, and heterodyne detection.

Figure 11A:
FIGS. 11A and 11B depict various steps in a method according to an embodiment of the present invention for analysis of fluorescence signal obtained by illuminating a sample with a combined beam composed of a plurality of RF comb beams and a top-hat profiled LO beam, FIG. 12 schematically depicts selected components of an exemplary hardware implementation of an analysis module according to an embodiment of the present invention.
Figure 11B:
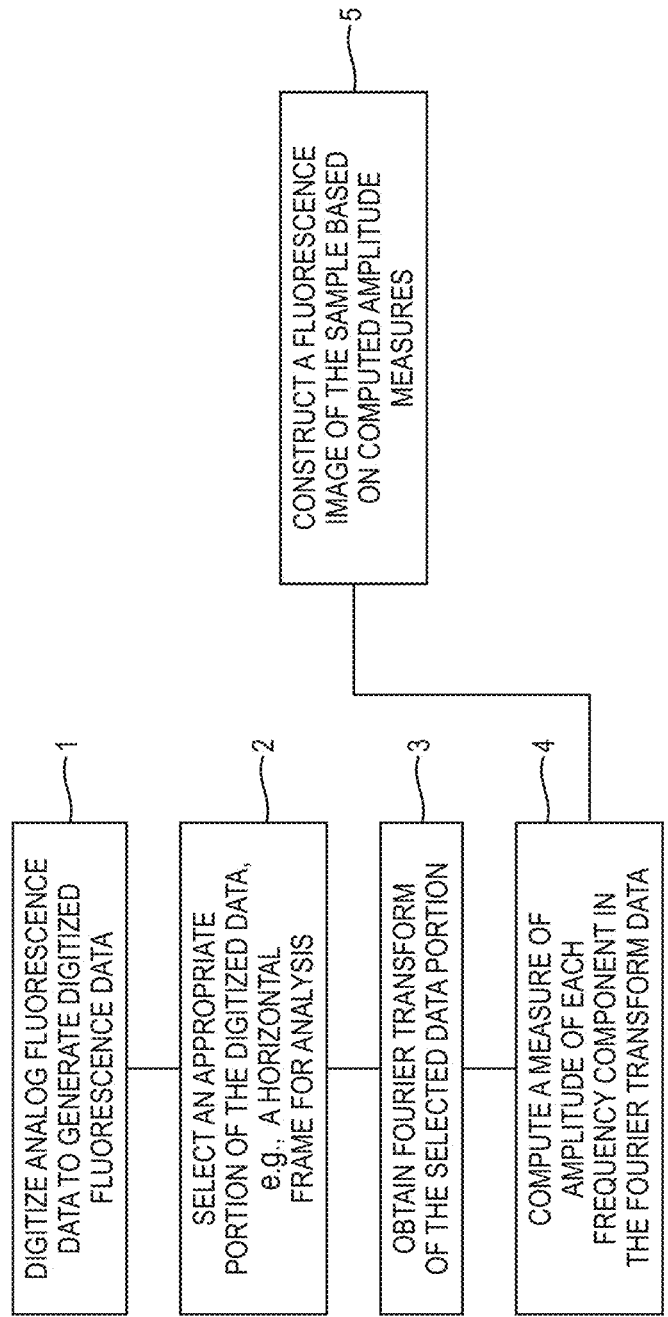

By way of example, FIGS. 11A and 11B show exemplary analysis steps that can be performed by the analysis module 72 to generate a fluorescence image of the sample. In step (1), the analog amplified signal is digitized to generate digitized fluorescence data. In step (2), an appropriate portion (length) of the digitized data is selected for analysis. For example, the fluorescence data corresponding to an illuminated row of the sample (herein also referred to as a frame) can be chosen for analysis. Alternatively, a portion of a data frame can be selected for analysis.

In step (3), a Fourier transform of the selected data is performed. By way of example, in some embodiments, a Fast Fourier Transform (FFT) of the data is performed to determine frequency components of the data. In some such embodiments, the bins of the FFT can correspond to the frequencies chosen for data acquisition. For example, for a 256 MHz sampling rate, 256 samples can yield frequency bins that are separated from one another by 1 MHz, e.g., from DC to 128 MHz. The FFT analysis provides frequencies corresponding to the beat frequencies at which the emitted fluorescence emission exhibits amplitude modulation.

With continued reference to FIGS. 11A and 11B, in this embodiment, in step (4), a measure of the amplitude of each frequency component present in the FFT data is computed by obtaining the square root of the sum of squares of the real and imaginary components of that frequency component. As each frequency component corresponds to one of the beat frequencies employed to elicit the fluorescence radiation from a particular location of the sample, the measure of the amplitude of the frequency component can provide a pixel value for a location associated with that frequency component along a horizontal row of the sample. In this manner, pixel values for an image of a horizontal row of the sample can be determined. The above steps can be repeated for fluorescence data obtained for each horizontal row of the sample as the sample flows through the flow cell in a vertical direction. The pixels values can be used to construct a fluorescence image (step 5).

Figure 12:
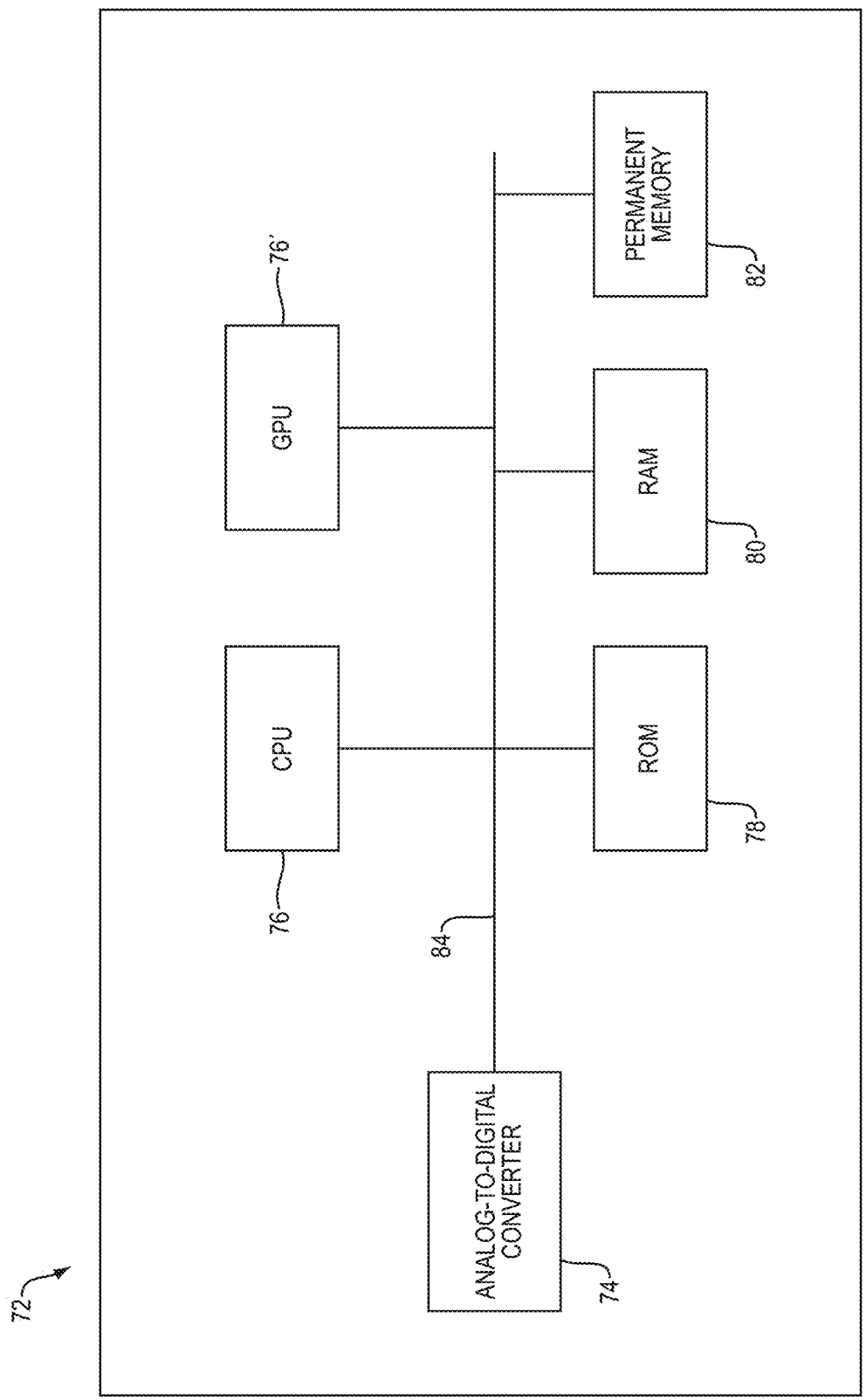

As noted above, the analysis module 72 can be implemented in hardware, firmware and/or software using techniques known in the art and in accordance with the present teachings. By way of example, FIG. 12 schematically depicts an exemplary implementation of analyzer 72, which includes an analog-to-digital converter 74 for receiving the amplified fluorescence signal from the amplifier 70 and digitizing that signal to generate digitized fluorescence data. The analysis module further includes a central processing unit (CPU) 76 for controlling the operation of the analysis module, including performing calculations and logic operations. The analysis module also includes ROM (read only memory) 78, RAM (random access memory) 80 and permanent memory 82. A communications bus 84 facilitates communication among various components of the analysis module, including communications between the CPU 76 and other components. The memory modules can be used to store instructions for analyzing the fluorescence data and the analysis results. By way of example, in some embodiments, instructions for data analysis, e.g., instructions for performing the above steps discussed in connection with FIGS. 11A and 11B, can be stored in the ROM 78. The CPU can employ instructions stored in ROM 78 to operate on digitized fluorescence data stored in RAM 80 to generate a fluorescence image of the sample (e.g., a one-dimensional or a two-dimensional image). The CPU can effect the storage of the fluorescence image in permanent memory 82, e.g., in a database. As shown schematically in FIG. 12, the analysis module can optionally include a graphics processing unit (GPU) 76' for performing calculations of pixel intensities and other quantities from the received data (e.g., fluorescence data).

Figure 13A:
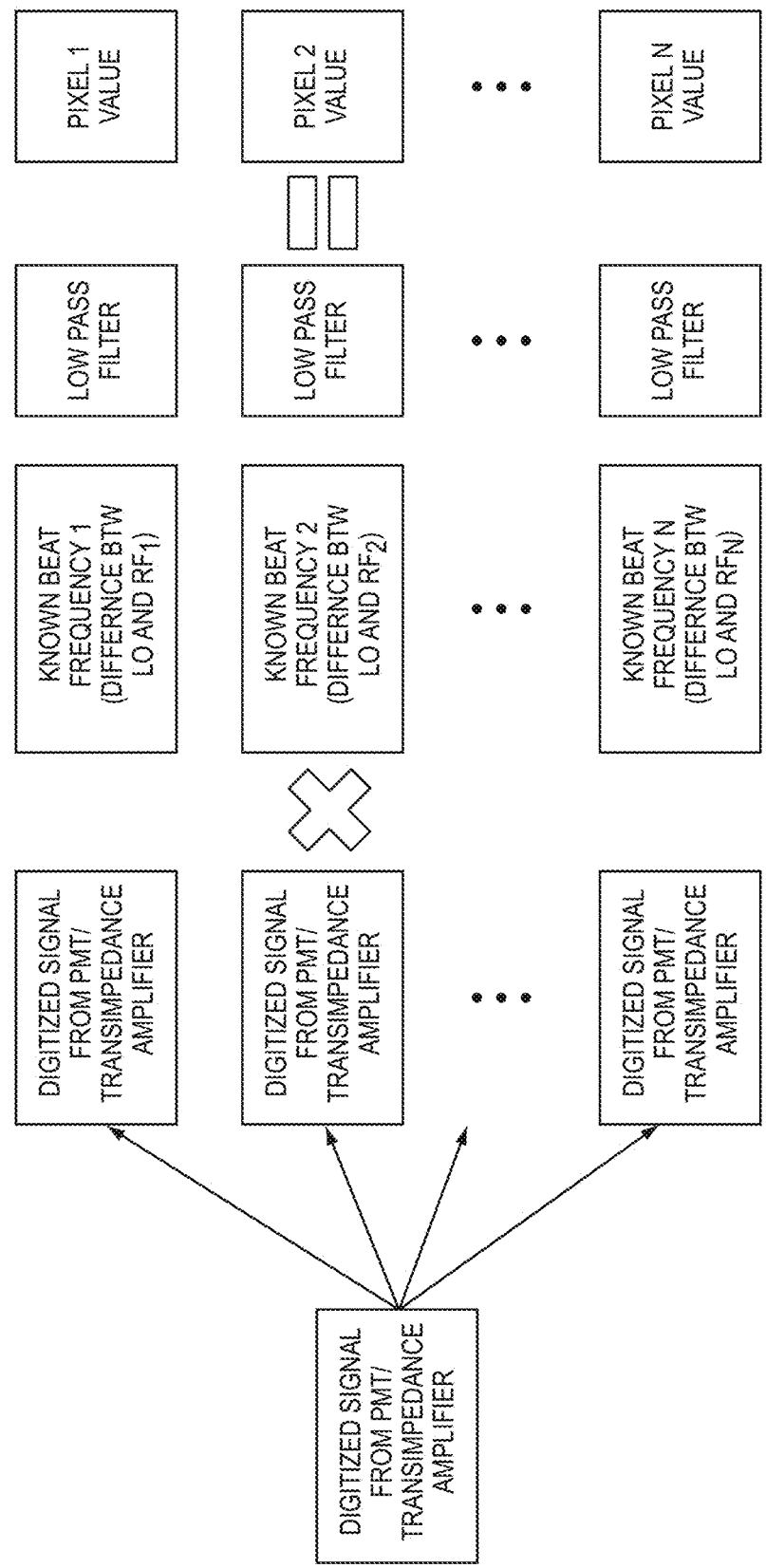
FIGS. 13A and 13B depict various steps in another method according to an embodiment of the invention for analysis of fluorescence signal obtained by illuminating a sample with a combined beam composed of a plurality of RF comb beams and a top-hat profiled LO beam.
Figure 13B:
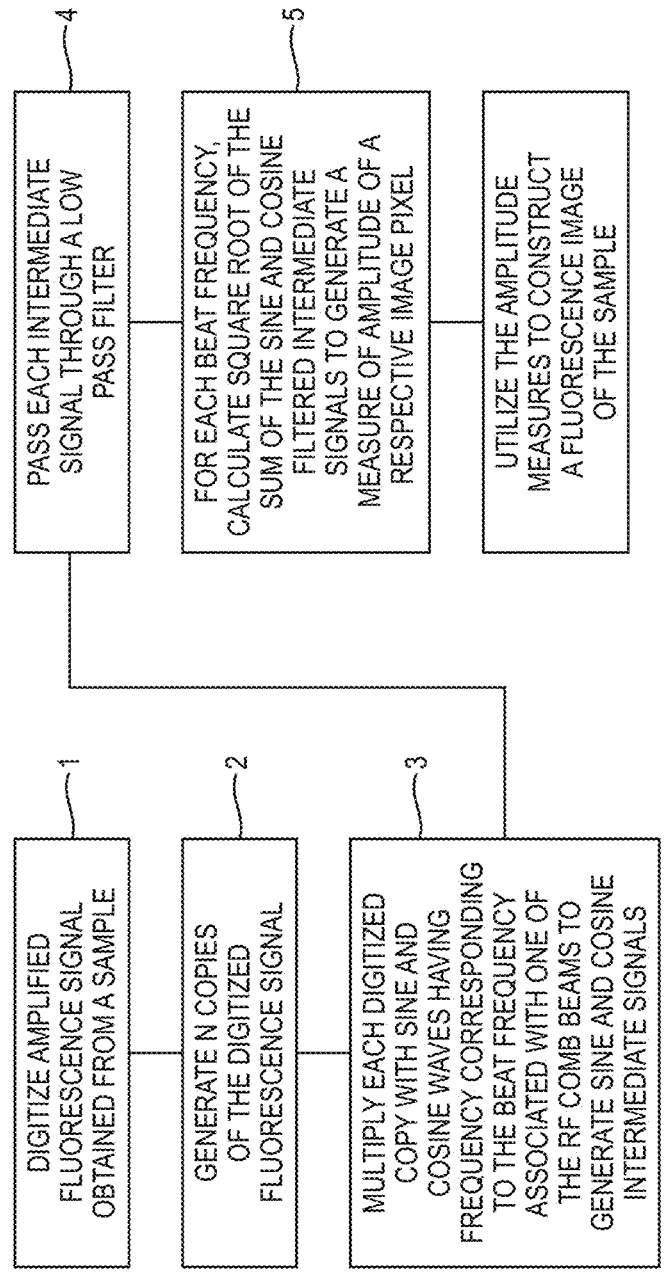

In some embodiments, the frequency demodulation of the output signal generated by the photodetector can be achieved using lock-in detection techniques. By way of example, with reference to FIGS. 13A and 13B, in one such embodiment, the amplified fluorescence signal is digitized (step 1) and several copies of the digitized fluorescence signal are generated (step 2), where the number (N) of the digitized copies corresponds to the number of frequencies associated with the RF comb beams. Each digitized copy of the signal is multiplied with sine and cosine waves having a frequency corresponding to a beat frequency equal to a difference between the frequencies of one of the RF comb beams and the LO beam to generate a plurality of intermediate signals (step 2). Each intermediate signal is passed through a low-pass filter (step 3), which has a bandwidth equal to one half of the frequency spacing between the RF comb frequencies.

For each beat frequency corresponding to one of the RF comb frequencies (in other words, for each frequency corresponding to a spatial location of the illuminated sample), square root of the sum of the squares of the two filtered intermediate signals corresponding to that frequency is obtained as a measure of the amplitude of an image pixel corresponding to the sample location illuminated by the LO beam and the RF comb beam having that frequency (step 4). In some embodiments, multiple fluorescence data signals corresponding to the same beat frequency (i.e., corresponding to the same sample location) can be processed in a manner discussed above and the pixel values can be averaged so as to obtain an average pixel value.

The above steps can be repeated for fluorescence data obtained for each horizontal row of the sample as the sample flows through the flow cell in a vertical direction. The pixels values can be used to construct a fluorescence image (step 5).

The above lock-in detection method can be implemented in software, firmware and/or hardware. By way of example, in one embodiment the above lock-in detection method can be implemented using a field programmable gate array (FPGA), particularly if more than 6 frequencies are used. In some embodiments, a multi-frequency lock-in amplifier, such as HF2L-MF multi-frequency amplifier marketed by Zurich Instruments of Zurich, Switzerland can be employed.

Figure 14A:
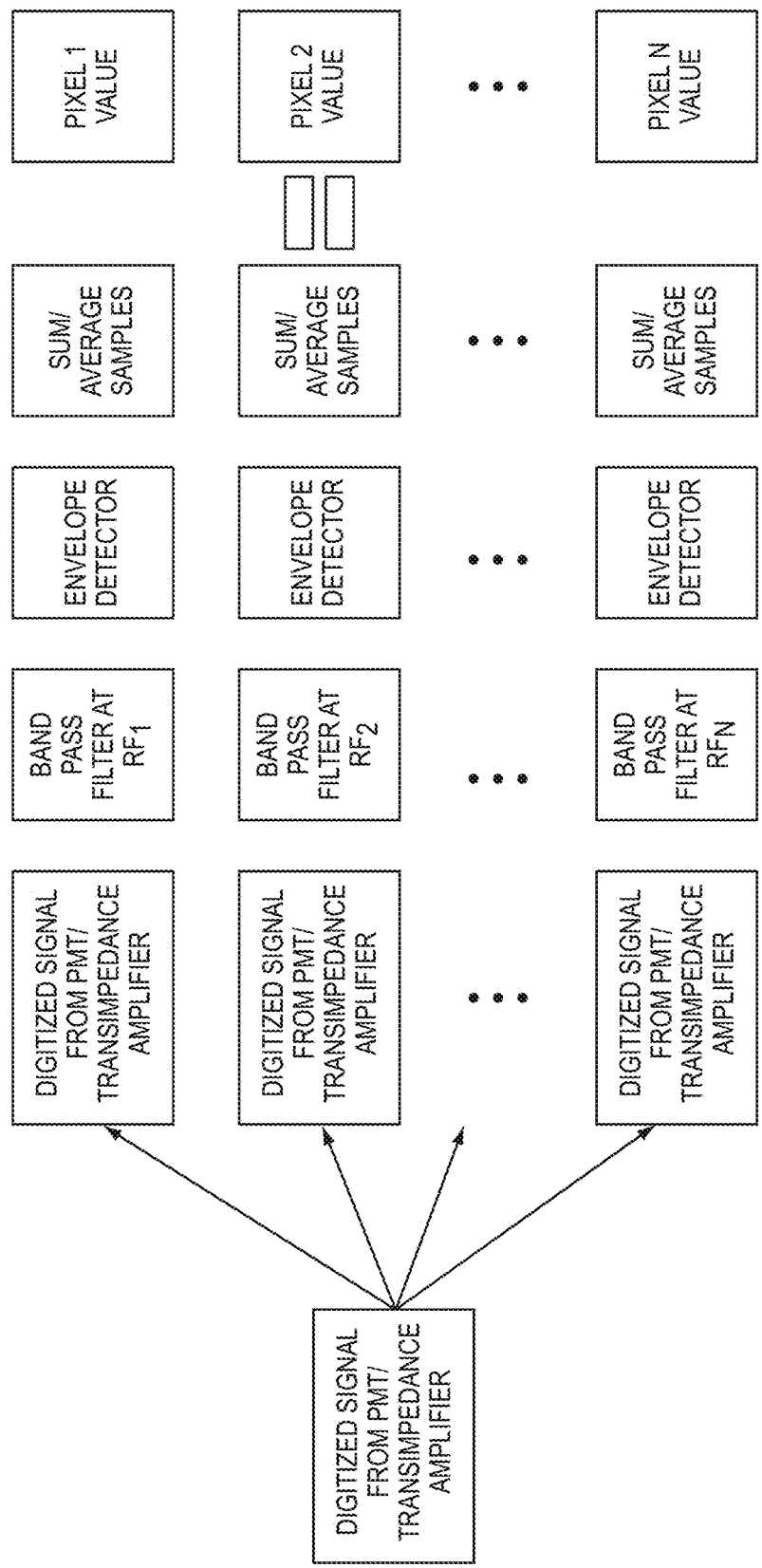
FIGS. 14A and 14B depict various steps in yet another method according to an embodiment of the invention for analysis of fluorescence signal obtained by illuminating a sample with a combined beam composed of a plurality of RF comb beams and a top-hat profiled LO beam, FIG. 15A schematically depicts illumination of a sample by a top-hat profiled beam at a single excitation frequency.
Figure 14B:
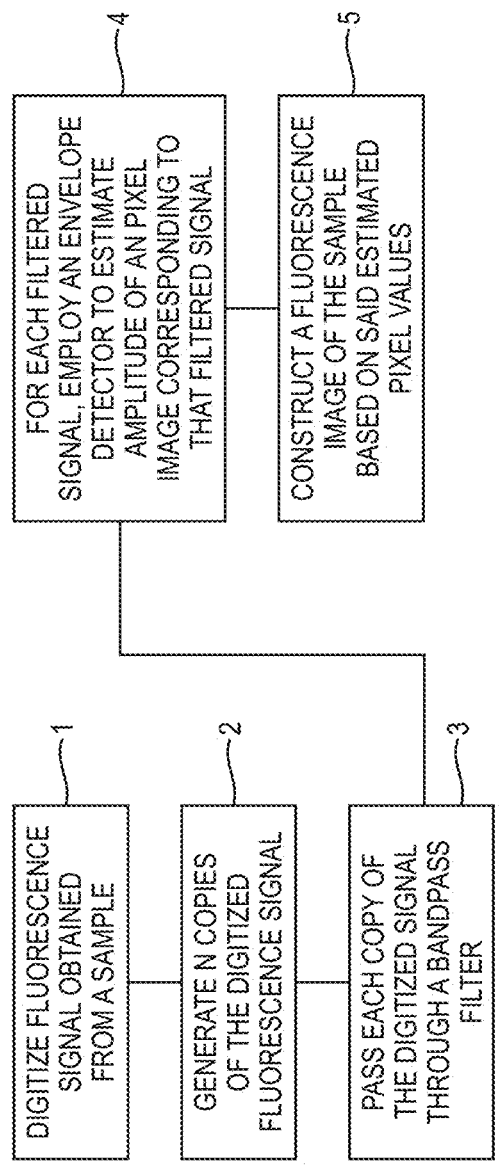

By way of further examples, in some embodiments the frequency demodulation of the detected fluorescence signal can be achieved by employing a bandpass filter-based image demodulation technique. By reference to FIGS. 14A and 14B, in one embodiment of such a frequency demodulation method, the fluorescence signal provided by the photodetector 64 and the amplifier 70 is digitized (step 1) and several copies of the digitized signal are generated (step 2), where the number (N) of the digitized copies corresponds to the number of frequencies associated with the RF comb beams. Each copy of the digitized fluorescence signal is filtered by passing that signal through a bandpass filter centered at a beat frequency associated with one of the RF comb beams (i.e., a beat frequency associated with a particular location of the sample) (step 3). More specifically, each bandpass filter is centered at one of N beat frequencies and has a bandwidth that is equal to half of the frequency spacing between adjacent beat frequencies.

An envelope detector at each beat frequency is employed to estimate, for each horizontal line, the amplitude of each pixel corresponding to that frequency (step 4). In some cases, a plurality of pixel values corresponding to a pixel, obtained by processing multiple fluorescent signals corresponding to a sample location associated with that pixel, is averaged to obtain an average pixel value. The above steps can be repeated for fluorescence data obtained for each horizontal row of the sample as the sample flows through the flow cell in a vertical direction. The pixels values can be used to construct a one-dimensional or a two-dimensional fluorescence image of the sample (step 5).

The analysis module can also be configured to receive and process the brightfield and darkfield image data. For example, with reference to FIG. 9C and FIG. 10, the analysis module 72 can be further configured to receive the darkfield and brightfield image data from photodetectors 208 and 218 to generate darkfield and brightfield images. For example, with reference to FIG. 12, the instructions for generating the darkfield and brightfield images, e.g., in a manner known in the art, can be stored in permanent memory 82. The processor 76 can employ these instructions to process the received darkfield and brightfield image data to generate the images. The analysis module can be also configured to generate composite images by overlaying, e.g., a fluorescence image and one or both of the brightfield and darkfield images.

The fluorescence images as well as the brightfield and darkfield images generated by a system according to the present teachings, such as the above system 10, can be used for a variety of different ways. For example, the fluorescence image can be integrated to produce a value comparable to the data produced by a conventional flow cytometer. The fluorescence image can also be analyzed to determine the location of fluorescent probe giving rise to that image (e.g., it can be determined whether the probe is the nucleus, cytoplasm, localized to organelles, or on the outside of the cell membrane). Further, in some applications, multiple fluorescent images obtained by detecting different fluorescent bands, all of which taken from the same cell, can be used to determine the degree of co-localization of multiple fluorescent probes within a cell. Additionally, the analysis of cell morphology, cell signaling, internalization, cell-cell interaction, cell death, cell cycle, and spot counting (e.g., FISH), among others, are possible using multi-color fluorescence, brightfield, and darkfield images.

As noted above, the system 10 can be operated in at least three different modes. In one mode discussed above, an LO beam and a plurality of RF comb beams concurrently illuminate a portion of the sample (e.g., locations disposed along a horizontal extent), and the fluorescence radiation emitted from the illuminated locations is detected and analyzed in order to construct a fluorescence image of the sample. In another operational mode, rather than applying a plurality of RF drive signals concurrently to the AOD, a frequency ramp containing the drive signals is applied to the AOD such that the frequency of the laser beam is changed over time from a start frequency ($f_1$) to an end frequency ($f_2$). For each drive frequency in the frequency ramp, the frequency of the laser beam is shifted by that drive frequency and the sample is illuminated by the frequency-shifted laser beam to elicit fluorescence radiation from the sample. In other words, in this mode, the system is operated to obtain fluorescence radiation from the sample by illuminating the sample successively over a temporal interval with a plurality of frequencies, which are shifted from the central laser frequency. The frequency shift generated by the AOD is accompanied by an angular deflection such that using the same optical path, the beam is scanned across the sample at a high speed.

More specifically, in this operational mode, the RF frequency synthesizer 10 is employed to ramp a drive signal applied to the AOD 18 from a start frequency ($f_1$) to an end frequency ($f_2$). By way of example, the frequency range over which the drive signal is ramped can be from about 50 MHz to about 250 MHz. In some embodiments, the drive signal is ramped from about 100 MHz to about 150 MHz. In this embodiment, the drive frequency is changed over time continuously, e.g., to achieve a high speed. In other embodiments, the drive frequency can be changed in discrete steps from a start frequency ($f_1$) to an end frequency ($f_2$).

The drive frequencies are chosen such that the frequency-shifted beam would miss the mirror 28 and propagate along an optical path defined by lens 26, lens 30, mirrors 40/42, a beam splitter 44, lens 46, mirror 56, lens 50, mirror 58 and the objective lens 52 to illuminate a portion of the sample flowing through the sample holder. The ramp rate is preferably fast enough so as to ameliorate and preferably prevent, any blur in the vertical direction of a fluorescence image to be generated based on the emitted fluorescence radiation as the sample flows across the beam. This can be achieved, for example, by matching the ramp rate with the sample's flow speed. The laser spot size at the sample can be used to estimate appropriate rates. By way of example, for a laser spot size of 1 micrometer, the scan time across 1 line should be 10 microseconds or less for a sample flow speed of 0.1 meters per second to avoid image blur.

The fluorescence radiation emitted from the sample in response to illumination by the excitation radiation is collected and detected in a manner discussed above. Specifically, with reference to FIG. 10, the fluorescence radiation is detected by photodetector 64. The detected fluorescence is amplified by the amplifier 70 and the amplified signal is analyzed by the analysis module 72 to reconstruct a fluorescence image of the sample. The reconstruction of the image is performed by assigning a horizontal pixel location to a specific time within the scan period from the start frequency ($f_1$) to the end frequency ($f_2$). As opposed to analyzing the amplitude of a frequency component to obtain pixel values as in the above operational mode, the demodulation approach used in this operational mode only uses the time domain values of the detected fluorescence signal to assign values to the pixels of the image. The process can be repeated as the sample flows in a vertical direction so as to obtain a two-dimensional fluorescence image of the sample.

The fluorescence radiation, if any, emitted by the sample is collected by photodetector 64. Referring to FIG. 10, the detected fluorescence radiation is amplified by the amplifier 70. The analysis module 72 receives the amplified signal. In this operational mode, the analysis module analyzes the fluorescence signal to determine the fluorescence content of the sample, e.g., a cell/particle. Since there is only one beam exciting the sample in this operational mode, no beat frequencies are generated in response to exciting the sample. Hence, there is no image information in the frequency domain of the fluorescence signal. Rather, the detected fluorescence signal has image information encoded in the time domain. In this operational mode, an image can be digitally reconstructed using the time values of the detected fluorescence signal as the horizontal pixel coordinate, and the digitized voltage values of the fluorescence signal as the pixel values (brightness). Each scan of the drive frequencies applied to the AOD produces one horizontal line (row) of the image. The image reconstruction is achieved via consecutive scans as the sample flows through the illumination area (point).

In yet another operational mode, the system 10 can be operated to illuminate a plurality of locations of a sample concurrently by a single excitation frequency, which can be generated, e.g., by shifting the central frequency of a laser beam by a radiofrequency. More specifically, referring again to FIG. 1, in such an operational mode a single drive radio frequency can be applied to the AOD 18 to generate a laser beam having a frequency that is shifted relative to the laser beam entering the AOD 18. Further, the frequency-shifted laser beam exhibits an angular shift relative to the laser beam entering the AOD such that the radiofrequency laser beam is intercepted and reflected by the mirror 28 towards the top-hat beam shaper 34 via lens 32 and mirrors 33 and 35. The beam exiting the top-hat beam shaper is reflected by the beam splitter 44 and is focused by the lens 46 onto the intermediate image plane 48. In this plane, as shown schematically in FIG. 15A, the laser beam 1000 shows a stretched profile along the horizontal direction.

The horizontally-stretched laser beam is reflected by the mirror 56 to the positive lens 50. After passage through the lens 50, the laser beam is reflected by the mirror 58 to the objective lens 52. As discussed above, the positive lens 50 and the objective lens 52 form a telescope for relaying the top-hat profiled laser beam from the intermediate image plane 48 onto a sample flowing through the flow cell 54.

The horizontally-stretched laser beam illuminates a horizontal extent of the sample to excite a fluorophore of interest, if present in the sample, along that horizontal extent. Thus, in this operational mode, unlike the first operational mode in which a plurality of horizontal locations of the sample is illuminated at different excitation frequencies, a plurality of horizontal locations of the sample is illuminated at the same excitation frequency. This operational mode does not enable a user to obtain an image of cells or particles that flow by. However, in this operational mode, a higher optical power can typically be applied to the sample than in the other two operational modes, which can be useful for obtaining a higher signal-to-noise ratio data if images are not required. This operational mode is accessible by merely altering the electronic signal driving the acousto-optic deflector, without a need to make any mechanical changes to the system.

Thus, the system 10 can be operated in three distinct operational modes to elicit fluorescence radiation from a sample.

Figure 15B:
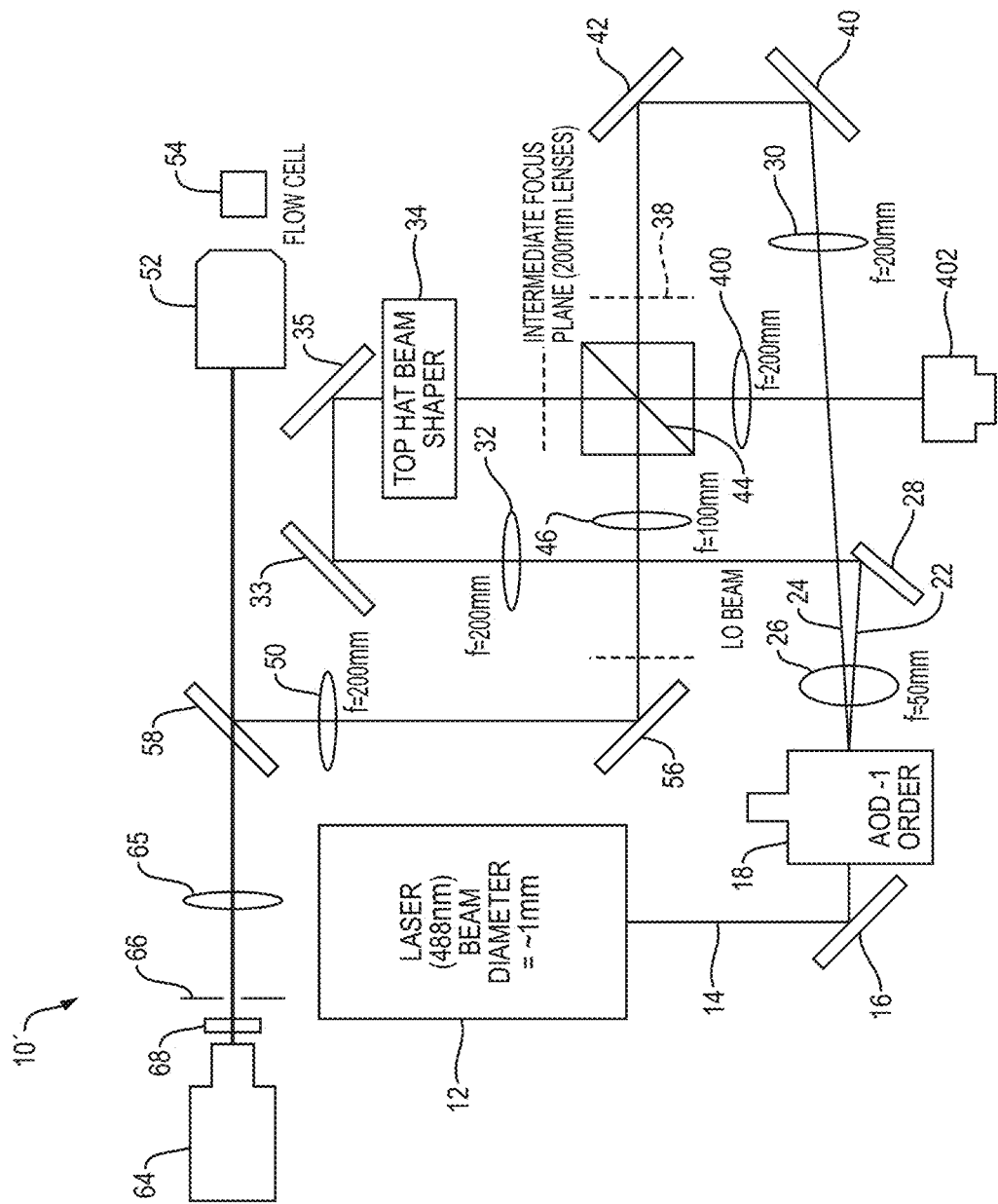
FIG. 15B is a schematic view of a system according an embodiment of the present teachings that allows for fluorescence lifetime measurements and fluorescence lifetime imaging.

In some embodiments, fluorescence lifetime measurements can be performed at each spatial position on the sample, e.g., by comparing the phase of the beats of each of the radiofrequency-shifted and local oscillator beams with the phase of a respective radiofrequency component in the detected fluorescence signal. By way of example, FIG. 15B shows a system 10', a modified version of the system 10 discussed above, that allows for such fluorescence lifetime measurements (certain components shown in FIG. 1 are not depicted in this figure for brevity). Specifically, a portion the RF comb beams incident on the beam splitter 44 is reflected by the beam splitter onto a convergent lens 400 (by way of illustration in this embodiment the lens 400 has a focal length of 200 mm, though other focal lengths can also be used). The lens 400 focuses that portion of the RF comb beams onto a photodiode 402, which detects the excitation beam. The output of the photodiode 402 can be received by the analysis module 72 (See, FIG. 10). The analysis module can provide frequency de-multiplexing of the excitation beam, e.g., using one of the de-modulation techniques discussed above and determine the phase of each radio frequency component in the excitation beam. This can provide, for each radiofrequency component in the detected fluorescence signal, a reference phase with which the phase of that radiofrequency component can be compared. For example, the real and imaginary components of an FFT of the excitation signal or the I and Q components of lock-in type demodulation can be employed. Alternatively, the output of the detector detecting the brightfield image of the sample/flow cell can be used to obtain reference phases with which the phases of the fluorescence beat frequencies can be compared.

More specifically, the analysis module 72 can provide frequency de-multiplexing of the detected fluorescence signal, e.g., in a manner discussed above. As will be appreciated by one skilled in the art, for each beat frequency in the fluorescence signal, the phase of the radiofrequency component can be compared with the respective reference phase of the excitation beam to obtain spatially-resolved fluorescence lifetime measurements and a fluorescence lifetime image.

In certain embodiments, the subject systems include flow cytometry systems employing the optical configurations described above for detecting light emitted by a sample in a flow stream. In certain embodiments, the subject systems are flow cytometry systems which include one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494; and 9,097,640, the disclosures of which are herein incorporated by reference in their entirety As discussed above, in some embodiments the subject systems are configured for imaging particles (e.g., cells) in a sample flowing as a flow stream, such as in the flow stream of a flow cytometer. The flow rate of particles in the flow stream may be 0.00001 m/s or more, such as 0.00005 m/s or more, such as 0.0001 m/s or more, such as 0.0005 m/s or more, such as 0.001 m/s or more, such as 0.005 m/s or more, such as 0.01 m/s or more, such as 0.05 m/s or more, such as 0.1 m/s or more, such as 0.5 m/s or more, such as 1 m/s or more, such as 2 m/s or more, such as 3 m/s or more, such as 4 m/s or more, such as 5 m/s or more, such as 6 m/s or more, such as 7 m/s or more, such as 8 m/s or more, such as 9 m/s or more, such 10 m/s or more, such as 15 m/s or more and including 25 m/s or more. For example, depending on the size of the flow stream (e.g., the flow nozzle orifice), the flow stream may have a flow rate in the subject systems of 0.001 µL/min or more, such as 0.005 µL/min or more, such as 0.01 µL/min or more, such as 0.05 µL/min or more, such as 0.1 µL/min or more, such as 0.5 µL/min or more, such as 1 µL/min or more, such as 5 µL/min or more, such as 10 µL/min or more, such as 25 µL/min or more, such as 50 µL/min or more, such as 100 µL/min or more, such as 250 µL/min or more and including 500 µL/min or more.

Figure 16A:
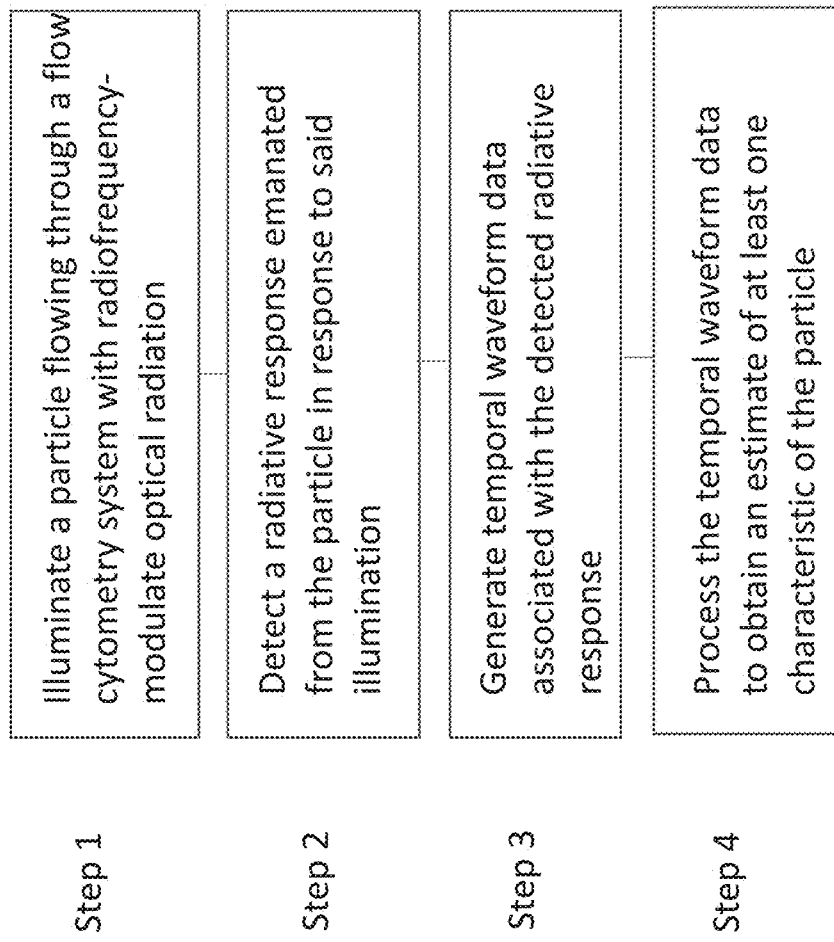
FIG. 16A is a flow chart depicting various steps for determining an estimate of at least one characteristic of a particle flowing through a flow cytometry system, FIG. 16B schematically depicts a system according to an embodiment for determining an estimate of at least one characteristic of a particle flowing through a flow cytometry system, FIG. 16AA is a flow chart depicting various steps in a method according to an embodiment for gating particles in a flow cytometry system based on values of one or more particle characteristics.
Figure 16A:
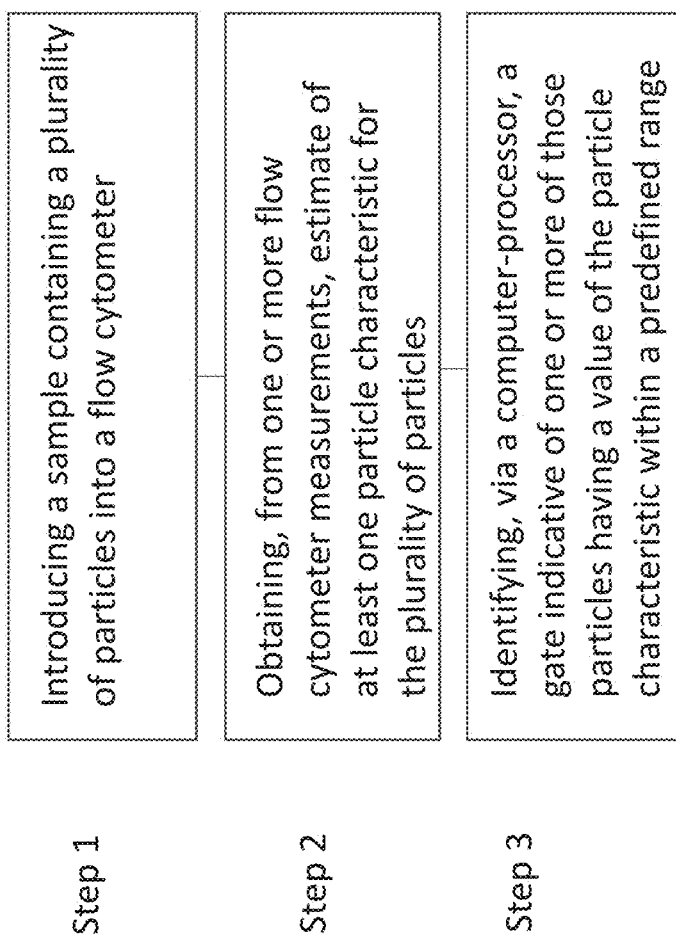

In some aspects, methods and systems are disclosed for providing an estimate of one or more characteristics of a particle, e.g., a cell. By way of example, FIG. 16A presents a flow chart depicting various steps in one exemplary method according to an embodiment of the present teachings for determining one or more characteristics of a particle. A particle is illuminated with a radiofrequency-modulated optical beam as the particle flows through a flow cytometry system so as to elicit at least one radiative response from the particle (step 1). By way of example, the radiofrequency-modulated optical beam can include at least two beamlets having optical frequencies shifted from one another by a radiofrequency. In some embodiments, the radiofrequency shift can be in a range of about 10 MHz to about 250 MHz. For example, the radiofrequency shift can be in a range of about 55 MHz to about 225 MHz, such as from about 60 MHz to about 200 MHz, such as from about 65 MHz to about 175 MHz, such as from about 70 MHz to about 150 MHz and including from about 75 MHz to about 125 MHz. By way of example, in some embodiments, the radiofrequency-modulated optical beam can be generated by introducing a laser beam to an acousto-optic deflector (AOD) and applying one or more drive signals at one or more radiofrequencies to the AOD in order to generate a plurality of angularly-separated beamlets having optical frequencies that are shifted relative to one another by said radiofrequencies, e.g., in a manner discussed above.

In some embodiments, the radiative response elicited from the particle in response to the illumination of the particle by the radio-frequency modulated optical beam can be any of fluorescent and/or scattered radiation.

With continued reference to the flow chart of FIG. 16A, the radiative response emanating from the particle can be detected (step 2) and a temporal waveform data associated with the radiative response can be generated (step 3). A variety of radiation detection modalities and detectors, such as those discussed above, can be used to detect the elicited radiation response. In some embodiments, the generated waveform can be a fluorescence and/or scattering waveform data. The waveform data can be processed to obtain an estimate of at least one characteristic of the particle. In many embodiments, such processing of the waveform data to obtain an estimate of at least one characteristic of the particle can be performed without generating an image of the particle based on the waveform data. In some embodiments, the processing step includes analyzing one or more beat frequencies modulating the temporal waveform data to obtain the estimate of at least one characteristic of the particle. In some embodiments, the processing step is performed sufficiently fast such that a latency associated with obtaining an estimate of at least one characteristic of the particle is less than about 100 microseconds.

In some embodiments, the above method can be used to obtain an estimate of any of a dimensional size of the particle, a ratio of sizes of the particle along two different dimensions, co-localization of fluorescence radiation emitted by two or more markers associated with the particle, or a degree of punctateness of the radiative response (e.g., the degree of punctateness of fluorescent radiation emitted by the particle), among others.

The above method can be used to obtain estimates of one or more characteristics of a variety of different particles. By way of example, the particle can be any of a cell, a small organism (e.g., the nematode c. elegan), a bead, a micropart, a nanoparticle, a viral particle, a bacterium, an exosome, or a pharmaceutical product.

Figure 16B:
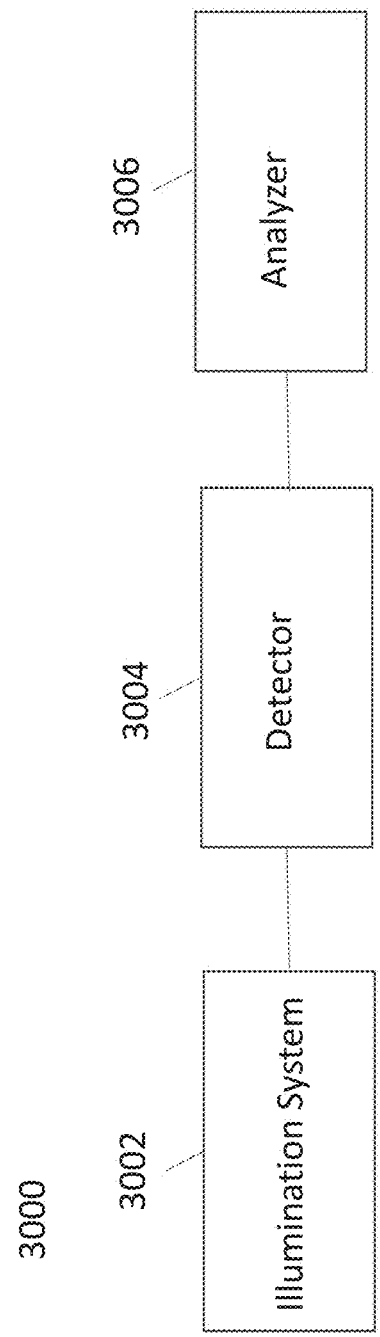
FIG. 16C is a flow chart depicting various steps in an embodiment for making a sorting decision based on co-localization of fluorescence radiation emitted from a particle, e.g., a cell, in two or more different frequency channels, FIG. 17 schematically depicts hypothetical fluorescence time-frequency waveforms corresponding to two channels and their product used in the method shown in the flow chart of FIG. 16.

FIG. 16B schematically depicts a system 3000 according to an embodiment for estimating at least one characteristic of a particle, such as a cell. The exemplary system 3000 includes an illuminating system 3002 for illuminating one or more particles flowing through a cell of a flow cytometry system with a radiofrequency-modulated optical laser beam. A detector 3004 can detect a radiative response of the particle, e.g., fluorescent and/or scattered radiation, in response to its illumination, and generate one or more signals indicative of the radiative response. An analyzer 3006 can receive the signal(s) from the detector and generate temporal waveform data and operate on that waveform data so as to derive an estimate of one or more characteristics of the particle.

The analyzer 3006 can employ a variety of different methods for analyzing the waveform data to obtain an estimate of one or more characteristics of a particle, such as a cell. By way of example, in some embodiments, a particle can be stained with at least two fluorescence markers, where each marker is configured to emit fluorescent radiation in response to illumination by radiofrequency-modulated optical radiation. The fluorescent radiation can be detected and digitized to generate fluorescence waveforms each corresponding to one of the markers. The analyzer can operate on the fluorescence waveforms to obtain a measure of co-localization of the fluorescence radiation emanating from the markers. Specifically, the analyzer can apply a high-pass or a band-pass filter to at least one of the waveforms to generate at least one filtered waveform followed by a point-wise multiplication of the waveforms to generate a resultant multiplicative waveform, integrate the multiplicative waveform to obtain an integrated value, and compare the integrated value with a predefined threshold to obtain a measure of co-localization. By way of another example, in some embodiments, an estimate of the size of a particle along a direction perpendicular or parallel to the direction of the particle flow in a flow cytometry system can be obtained. For example, in some such embodiments, an estimate of a particle size in a direction perpendicular to the direction of particle flow can be obtained by squaring a fluorescence waveform corresponding to fluorescent radiation emitted by the particle in response to illumination by a radiofrequency-modulated optical beam, applying a bandpass filter to the squared waveform, integrating the filtered waveform, and comparing the integrated value with a predefined threshold. Further, in some embodiments, the analyzer can use scattering data to obtain an estimate of the size of a particle in a direction parallel to the direction of particle flow.

As discussed below, one or more estimated characteristics of a particle flowing through a flow cytometry system can be employed to arrive at a sorting decision regarding that particle, i.e., whether or not to sort that particle. Some examples of processing methods that can be used to operate on the waveform data to obtain an estimate of at least one characteristic of a particle are discussed below in the context of using the estimates of characteristics of cells flowing through a flow cytometer to arrive at sorting decisions regarding those cells. It should be understood that such processing methods can be used to obtain estimates of characteristics of particle other than cells, and further the estimated characteristics may not be used for sorting purposes.

In a related aspect, methods are disclosed for automatic gating (e.g., computer-assisted gating) of a population of particles, e.g., cells, flowing through a flow cytometer based on one or more characteristics of the particles. By way of example, such a method can gate a subset of a plurality of particles flowing through a flow cytometer based on the sizes of the particles being within a predefined range. For example, with reference to the flow chart of FIG. 16AA, such a method can include introducing a sample containing a plurality of particles into a flow cytometer (step 1), and obtaining, from one or more flow cytometer measurements, estimates of at least one particle characteristic for the plurality of the particles (step 2). The step of obtaining at least one particle characteristic can include illuminating a particle as it flows through the flow cytometer with radiation having at least two optical frequencies shifted from one another by a radiofrequency to elicit a radiative response from the particle, detecting the radiative response from the particle to generate temporal waveform data associated with the response, and processing said temporal waveform data to obtain a value of said at least one particle characteristic by analyzing one or more beat frequencies modulating said temporal waveform data. The method can further include identifying, via a computer processor, a gate indicative of one or more particles having a value of the particle characteristic that lies within a predefined range. By way of example, the particles having a dimensional size (e.g., a lateral size) within a predefined range can be gated.

A system such as the system depicted in FIG. 16B can be employed to perform the above gating methods. For example, the analyzer 3006 can be programmed to determine an estimate of at least one characteristic of a plurality of particles, e.g., based on the analysis of one or more beat frequencies in the fluorescent radiation emitted by those particles in response to illumination by a radiofrequency-modulated optical beam, and determine whether the estimate of the characteristic of a particle is within a predefined range in order to arrive at a gating decision with respect to that particle (e.g., if the determined characteristic is within a predefined range, the particle will be gated). In some embodiments, the teachings of U.S. Pat. No. 8,990,047 titled "Neighborhood Thresholding in Mixed Model Density Gating", as modified based on the present teachings can be used to gate particles flowing through a flow cytometer. U.S. Pat. No. 8,990,047 is hereby incorporated by reference in its entirety.

In some aspects, methods and systems are disclosed for sorting cells based on interrogation of those cells via radiofrequency modulated optical radiation, e.g., an optical radiation beam comprising two or more optical frequencies separated from one another by one or more radiofrequencies. In some embodiments, the optical beam can include a plurality of angularly or spatially separated beamlets each of which has a radiofrequency shift relative to another. In some cases, the use of such a beam allows illuminating different locations within a particle (e.g., a cell) at different radiofrequency-shifted optical frequencies. As discussed in more detail below, such methods can provide a sorting decision by employing the time-varying signal generated by the cells in response to illumination by the optical beam without a need to compute a fluorescence image based on the detected signal(s). While various embodiments of the methods according to the present teachings are discussed below in the context of sorting cells (e.g., in a flow cytometry system), the methods described herein can also be employed for sorting other types of particles, such as, small organisms (e.g., the nematode c. elegan), beads, microparticles, nanoparticles, viral particles, bacteria, exosomes, or pharmaceutical products. In some embodiments, the particles that can be sorted using the present teachings can have a size (e.g., a maximum size) in a range of about 50 nanometers to about 1 millimeter, e.g., in a range of about 100 nanometers to about 1 micrometer.

Further, in many embodiments, the sort methods discussed herein can be employed to provide sort decisions with a low latency, e.g., such that a cell or other particle can be sorted using a sorting apparatus operating at a high particle throughput (e.g., more than 1000 sorting operations per second may be performed). By way of example, the methods described herein can be used to make a sort decision with a latency equal to or less than about 100 microseconds, e.g., in a range of about 10 microseconds to about 100 microseconds, or in a range of about 20 microseconds to about 80 microseconds, or in a range of about 30 microseconds to about 70, or 50, microseconds. The term "latency" is used herein to indicate the time lapse between illuminating a particles, e.g., a cell, with interrogating radiation and arriving at a characteristic of the particle and/or a sorting decision regarding that particle.

Figure 16C:
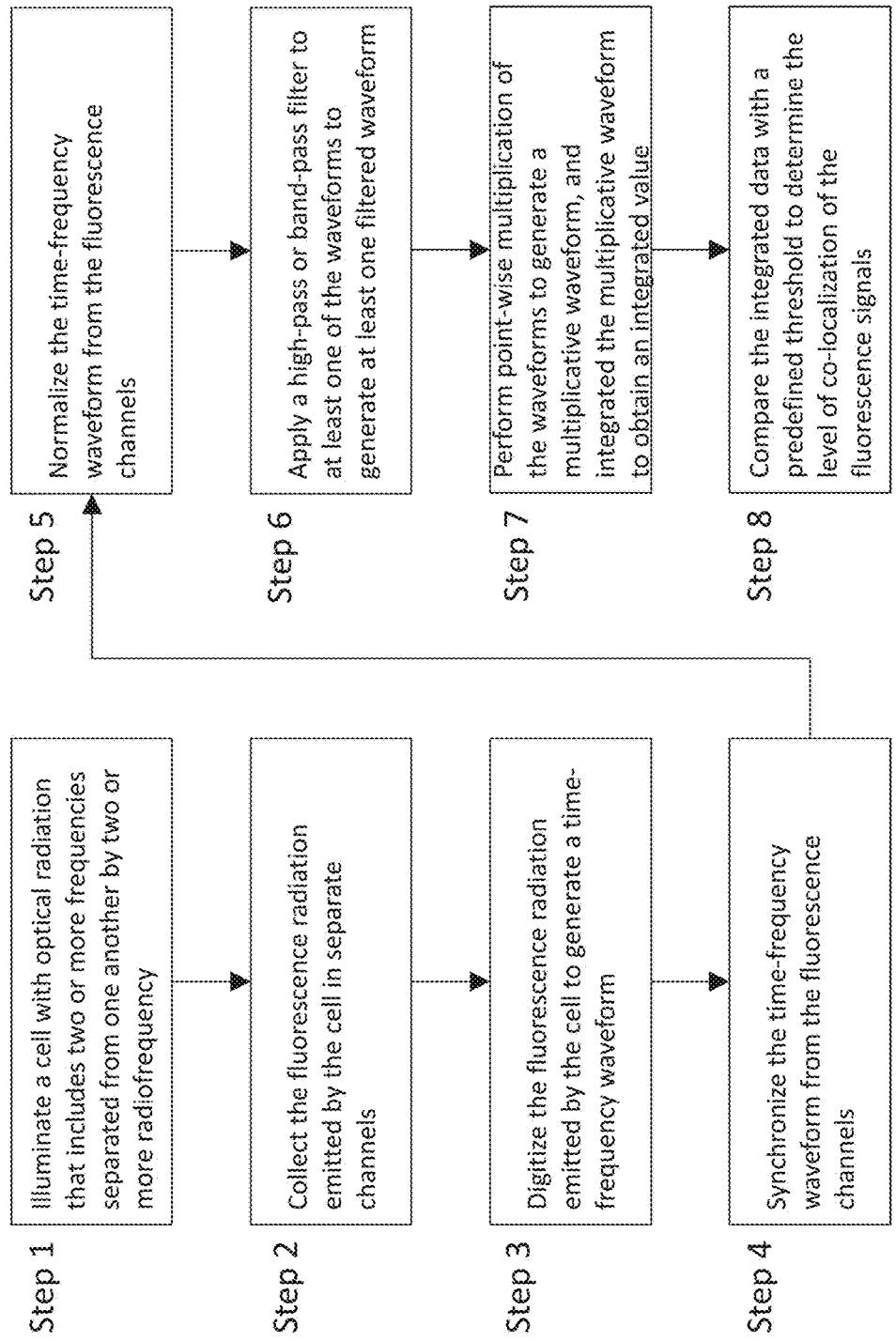

By way of example, the flow chart of FIG. 16C depicts a method according to an embodiment for sorting particles (e.g., cells) based on the degree of co-localization of fluorescence signals corresponding to two or more fluorophores (e.g., exogenous and/or endogenous fluorophores) emanating from the particles. Without any loss of generality, the particle is assumed to be a cell in the following discussion. In step (1), a cell is optically interrogated via illumination with an optical radiation beam that includes two or more optical frequencies that are separated from one another by one or more radiofrequencies. In some cases, the optical beam can include a plurality of angularly or spatially separated beamlets each of which has a radiofrequency shift relative to another. The use of such a beam allows illuminating different locations within the cell at different optical frequencies, which are shifted from one another by one or more radiofrequencies. The optical frequencies can be selected to excite two or more fluorophores that are expected to be associated with the cell. For example, the fluorophores can be fluorescent dye molecules with which the cell are tagged, e.g., via staining. By way of example, in some embodiments, the optical frequencies of the radiation beam can be in a range of about 300 THZ to about 1000 THZ and the radiofrequency separation between the optical frequencies can be, for example, in a range of about 50 MHz to about 250 MHz.

The fluorescent radiation emanating from the excited cell can then be collected in two (or more) separate fluorescence channels, each of which corresponds to fluorescent radiation emitted by one of the fluorophores (step 2). This can be achieved, for example, by employing the detector arrangement discussed above in connection with FIG. 9A. The collected fluorescent radiation in each channel can be digitized (step 3) and represented as a time sequence of signal values (fluorescence intensity). In this and other embodiments, such a time sequence of signal values, which can encode beat frequencies present in the fluorescent radiation is referred to as time-frequency waveform. The digitized time-frequency waveform corresponding to two or more fluorescence channels are temporally synchronized (step 4) and normalized (step 5). The normalization can be achieved, for example, by dividing each waveform by its maximum value and multiplying the waveform by a scaling factor.

A high-pass or a band-pass filter can be applied to at least one of the waveforms to generate at least one filtered waveform (step 6). In some embodiments, a low-pass filter is applied that allows the passage of frequencies less than about 1 MHz, and substantially blocks higher frequencies. Some examples of suitable low-pass filters include, without limitation, time-domain finite impulse response (FIR) filters or Fourier-domain filters.

The waveforms can then be point-wise multiplied to obtain a multiplicative waveform, and the multiplicative waveform can be integrated to obtain an integrated value (step 7). By way of illustration, FIG. 17 shows an array 1700 that represents the filtered normalized time-sequenced digitized fluorescence signal detected in one fluorescence channel and an array 1701 that represents the filtered normalized time-sequenced digitized fluorescence signal detected in another fluorescence channel, which is temporally synchronized with the array 1700 (for simplicity, in this illustrative example, the number of fluorescence channels is chosen to be two and the number of array elements is chosen to be ten, it should be understood that the number of fluorescence channels may be more than 2 and the number of array elements more than 10). This data is herein referred to as a time-frequency waveform. A resultant array 1702 is obtained via point-wise multiplication of the data in the arrays 1700 and 1701.

The temporal fluorescence signal from each channel includes beat frequencies corresponding to the interference of the radiofrequency-separated optical frequencies of the optical radiation beam. As such, the multiplication of their respective digitized data would exhibit the sum and difference of those frequencies. If the signals in the two or more fluorescence channels originate from substantially similar spatial locations within the excited cell, the resultant time-domain data obtained via multiplication of those signals would include frequency components at DC or close to DC based on the degree of co-localization of the signals in different fluorescence channels emanating from the excited cell.

In step (8), the integrated result is compared with a predefined threshold to determine whether the interrogated cell exhibits sufficient co-localization of the fluorescence signals to be qualified as a cell that satisfies the criterion for sorting. For example, if the integrated result equals or exceeds the predefined threshold, the cell would be selected for sorting. Otherwise, the cell would not be selected for sorting.

Figure 18A:
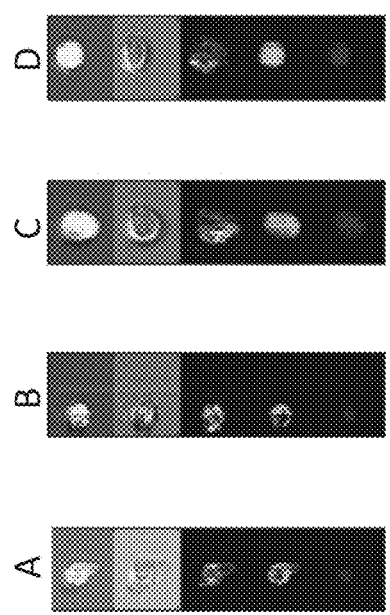
FIG. 18A shows fluorescence images of four cells labeled as A, B, C, and D, including green and red fluorescence images obtained by marking the cells with a green dye and a red dye as well as brightfield, darkfield images.
Figure 18B:
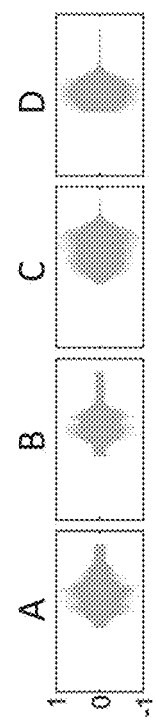
FIG. 18B shows the measured green fluorescence time-domain signal for the cells shown in FIG. 18A.
Figure 18C:
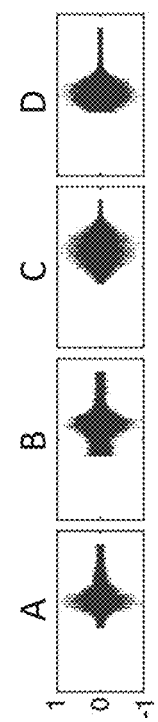
FIG. 18C shows measured red fluorescence time-domain signal for the cells shown in FIG. 18A.
Figure 18D:
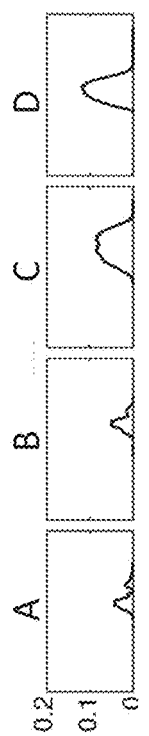
FIG. 18D shows, for each cell, a co-localization time-domain waveform obtained by multiplying the normalized red and green fluorescence waveforms shown in FIGS. 18B and 18C and passing the resultant waveform through a low pass filter.

By way of further illustration of the above co-localization method, FIG. 18A shows fluorescence images of four cells labeled as A, B, C, and D, where A and B cells were human leukocytes stained with anti-CD45-FITC and Propidium Iodide (PI), and cells C and D were HeLa cells stained with Calcein AM. These image sets contain 2-color fluorescence images obtained by detecting fluorescence from the cells stained with the above-mentioned stains, as well as brightfield and darkfield images. FIG. 18B shows the measured green (FITC) fluorescence time-domain signal, and FIG. 18C shows measured red (Propidium Iodide) fluorescence time-domain signal, obtained from cells A, B, C, and D in response to the illumination of these cells with optical radiation beating at frequencies in the range of 20 MHz-60 MHz. FIG. 18D shows, for each cell, a co-localization time-domain waveform is obtained by multiplying the normalized red and green fluorescence waveforms and passing the resultant waveform through a low pass filter (Fourier-domain low pass filter) to generate a filtered signal.

Figure 19:
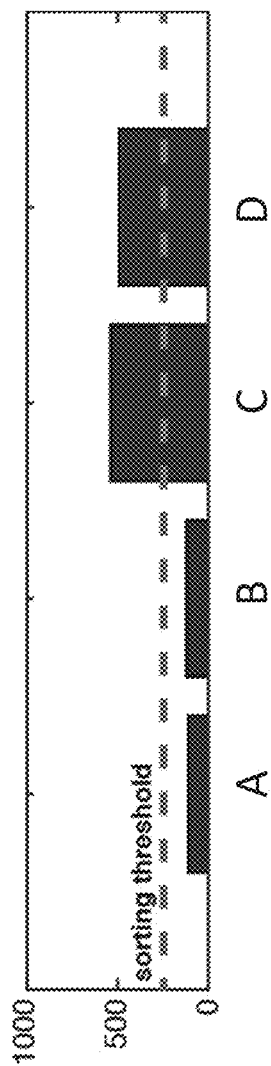
FIG. 19 shows the values of the integrated filtered signals for each of the cells A, B, C, and D (the dashed line in this figure represents the sorting threshold)

FIG. 19 shows the values of the integrated filtered signal for each of the cells A, B, C, and D. The dashed line in this figure represents the sorting threshold. While the integrated signals for cells A and B are below the sorting threshold, the integrated signals for cells C and D are above the sorting threshold. Thus, a positive sorting decision is adopted for cells C and D (i.e., cells C and D are selected for sorting) and a negative sorting decision is adopted for cells A and B.

The above sorting method based on fluorescence co-localization can be used in a variety of applications, for example, for translocation analysis.

In another aspect, a method for sorting cells in a flow cytometry system based on an estimate of the cell size is provided, where an estimate of the cell size is obtained via analysis of fluorescent radiation emitted by the cell. For example, the method utilizes the duration of a fluorescence pulse emanating from a cell to estimate the dimension of the cell along the direction of flow and analyzes the power contained in a low-pass filtered signal obtained by passing the square of the fluorescence signal through a low-pass filter to perform a sorting decision based on an estimate of a lateral dimension of the cell (e.g., a dimension of the cell orthogonal to the direction of cell flow).

More specifically, with reference to FIG. 19, in one embodiment, a cell is optically interrogated via illumination with an optical radiation beam that includes two or more optical frequencies that are separated from one another by one or more radiofrequencies (step 1). Similar to the previous embodiments, the optical beam can include, for example, a plurality of angularly or spatially separated beamlets each of which has a radiofrequency shift relative to another. The optical frequencies can be selected to excite one or more exogenous and/or endogenous fluorophores associated with the cell. The cell passes through the optical radiation beam and emits fluorescence in response to excitation by the beam. Without loss of generality, in this embodiment, the cell is assumed to flow in a vertical direction through the illumination beam and the emitted fluorescence is detected in a lateral (horizontal) direction that is substantially orthogonal to the flow direction of the cell.

A fluorescence signal emanated from the cell is then detected and digitized to generate a time-frequency waveform (step 2). The detected fluorescence radiation can then be analyzed to estimate the cell size, as discussed below. In some embodiments, the duration of a light scatter pulse emanated from the cell can be used to estimate the cell size along the direction of flow.

The duration of a fluorescence pulse emanating from a cell is related to the dwell time of the cell within the interrogating optical radiation beam, which is in turn related to the dimension of the beam in a direction parallel to the flow direction, the cell size in the direction of flow and the flow velocity of the cell. If the beam illuminating the cell has a diameter (H), and the flow velocity of the cell is V, and the cell has a size D (e.g., a diameter) in the direction of flow, then the size D can be approximated by the following relation:

$$D = V*T - 2*H \qquad \text{Eq. (2)}$$

where T is the detected optical pulse width. Hence, in step (3), the cell size in the direction of flow is estimated based on the temporal duration of the fluorescence or light scatter pulse emanated from the cell, e.g., using the above relation.

Figure 20:
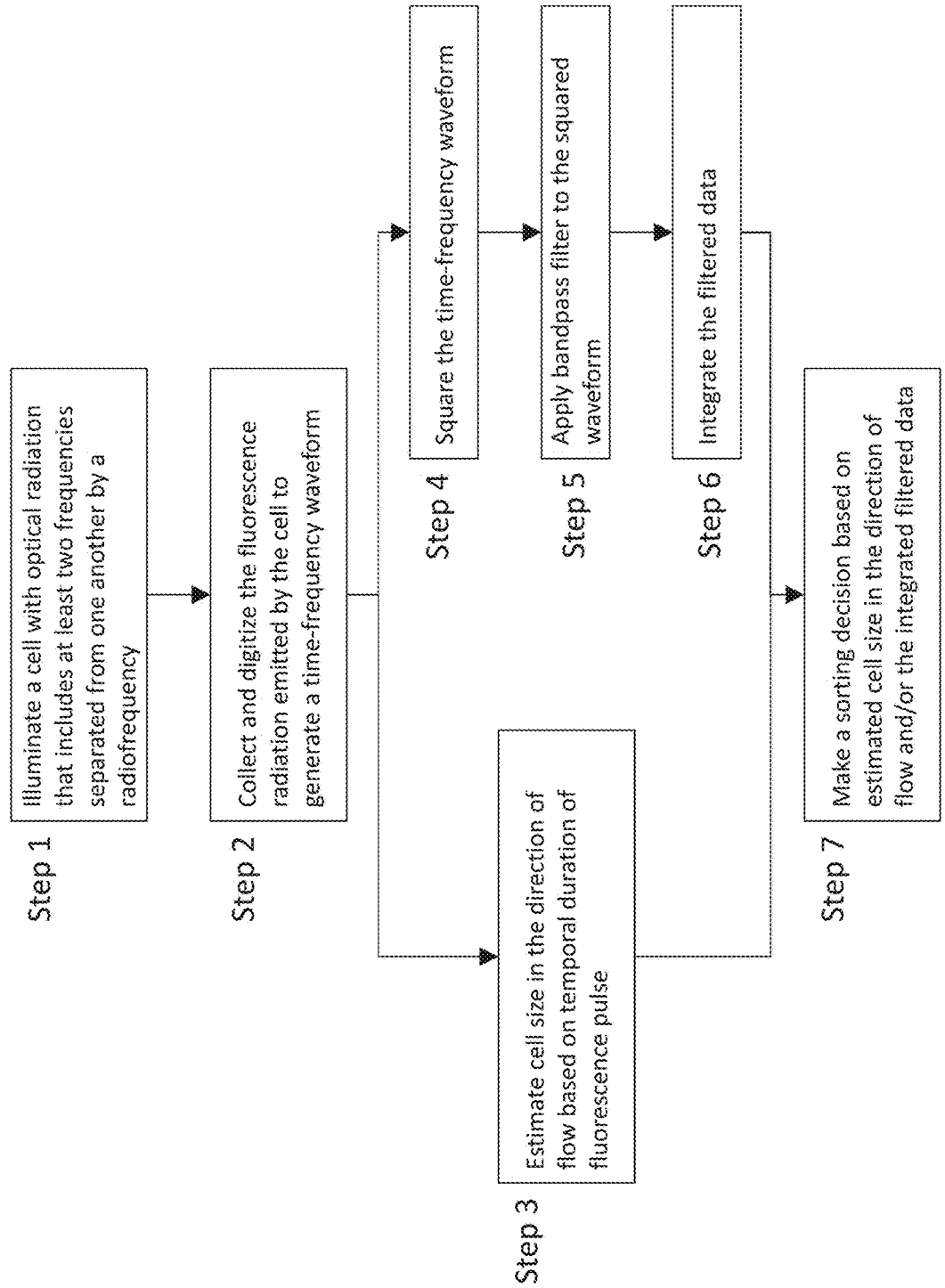
FIG. 20 is a flow chart depicting various steps in a cell sorting based on a cell size in accordance with an embodiment of the present invention, FIG. 21A schematically depicts a hypothetical cell illuminated by a hypothetical beam comprising a plurality of radiofrequency-modulated beamlets, FIG. 21B schematically depicts a hypothetical fluorescence waveform obtained from the illuminated cell shown in FIG. 21A as well as a waveform obtained by squaring the fluorescence waveform.

With continued reference to the flow chart of FIG. 20, in order to estimate the lateral size of the cell, the digitized fluorescence data is squared (step 4) and a bandpass filter is applied to the squared fluorescence data (step 5). The filtered data is then integrated to obtain a measure of integrated pulse power (step 6). The integrated pulse power can provide a measure of the lateral size of the cell. More specifically, based on the power present in the difference frequencies (which result as a consequence of the squaring operation) that fall within the band of the bandpass filter, the integrated pulse power can provide a measure of the lateral size of the cell.

In step (7), the estimate of the cell size in the flow direction and/or the integrated pulse power associated with the filtered data can be employed to make a sorting decision with respect to the cell. For example, in some embodiments, the estimated cell size in the direction of flow can be compared with a first threshold and the integrated pulse power can be compared with a second threshold to make a sorting decision. By way of example, in some cases, if both the estimated cell size in the direction of flow and the integrated pulse power exceed the respective thresholds, a positive sorting decision is made (i.e., the cell is selected). Alternatively, the sorting decision can rely only on the estimate of the cell size in the direction of the flow or the integrated pulse power. As discussed further below, in some cases, the ratio of the estimated vertical and horizontal cell sizes can be employed to make a sorting decision.

Figure 21:
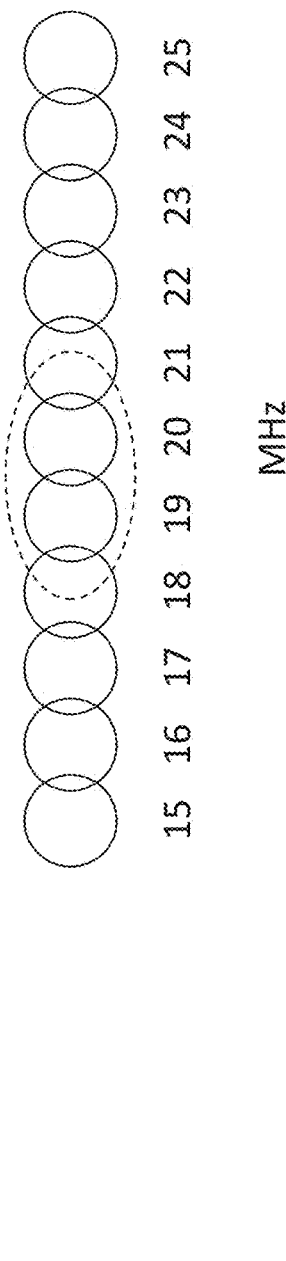

By way of further illustration of making a sorting decision based on an estimate of the lateral size of a cell, FIG. 21A schematically depicts a hypothetical cell illuminated by a hypothetical beam comprising a plurality of radiofrequency-modulated beamlets with radiofrequency modulations extending from 15 MHz to 25 MHz separated from one another by 1 MHz. The dashed line schematically depicts a cross-sectional view of the illuminated cell in a plane orthogonal to the direction of illumination. The fluorescence radiation collected from the cell and digitized can be in the form of a time-sequenced array 2100 of digitized fluorescence values, as shown schematically in FIG. 21B (the array is shown here only for illustrative purposes and not to limit the number of array elements that may be present in an actual fluorescence waveform). The waveform 2100 is squared to obtain the waveform 2101. A bandpass filter is then applied to the squared fluorescence waveform 2101, where the filter allows the passage of selected modulation frequencies between two frequencies $f_1$ and $f_2$ (where $f_2 > f_1$) while substantially blocking those modulation frequencies that are lower than $f_1$ or greater than $f_2$. By way of example, the bandpass filter can be an FIR bandpass filter, though other suitable filters known in the art may also be employed. The filtered data is indicative of the power present in the detected fluorescence pulse at modulation frequencies between $f_1$ and $f_2$. The filtered data is then integrated to obtain a measure of the total pulse power at frequencies between $f_1$ and $f_2$. This integrated result can then be compared with a threshold value to make a sorting decision. For example, the lateral size of the cell can be estimated to be less than a certain value based on the fact that the integrated result in less than the predefined threshold.

In this example, the cell size results in the illumination of the cell by optical radiation having radiofrequency modulations ranging from about 18 MHz to about 21 MHz. Hence, the difference between the maximum and the minimum modulation frequencies in the square of the fluorescence data would be about 6 MHz. If detection of cells having larger sizes that would result in difference frequencies in the square of their fluorescence data in a range of about 10 MHz to about 15 MHz were desired, a bandpass filter that would discriminate against frequencies below 10 MHz and above 15 MHz could be applied to the square of fluorescence data. In this example, the application of such a bandpass filter to the square of the fluorescence data would not result in a sufficiently large signal to indicate the presence of cells having the desired lateral sizes, as the difference modulations frequencies in the square of the fluorescence data are below 10 MHz.

The above sorting method based on cell size can have a variety of different applications, e.g., isolation by size of circulating tumor cells (CTCs).

Figure 22:
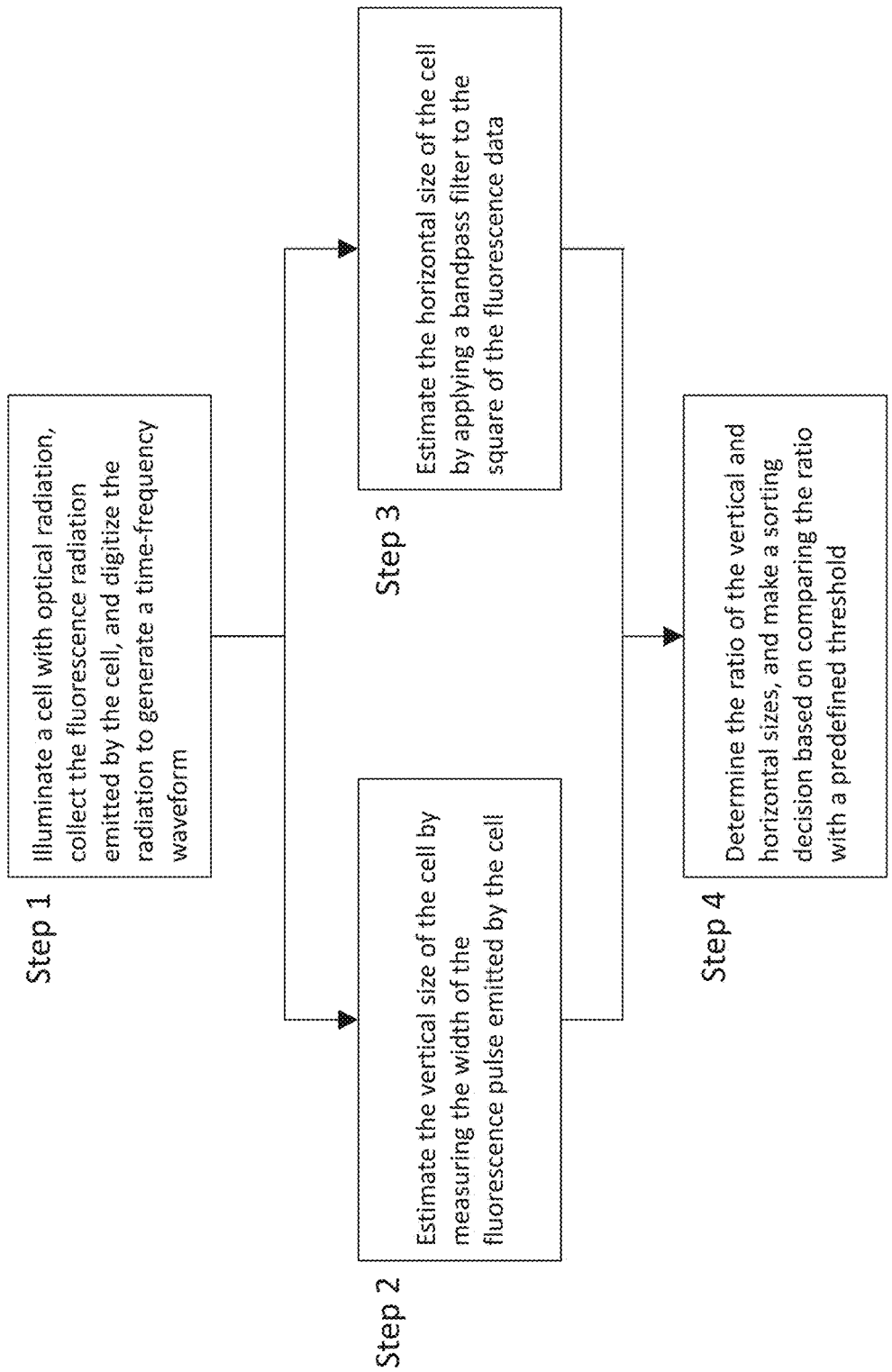
FIG. 22 is a flow chart depicting various steps in a method for sorting cells based on the cells' aspect ratio.

In another aspect, a method of sorting cells based on cells' aspect ratios is disclosed. For example, with reference to the flow chart of FIG. 22, a cell passing through an optical interrogation region is excited with radiation and fluorescence radiation emitted by the cell is collected and digitized (step 1) to generate a digitized time-frequency waveform. The digitized fluorescence data is then analyzed in a manner discussed above to estimate the vertical (along the direction of flow) cell size (step 2) and the horizontal (along a direction orthogonal to the direction of flow) cell sizes (step 3). More specifically, the vertical size of the cell can be estimated using the temporal width of a fluorescence or light scatter (or light transmitted) pulse emitted by the cell (step 2), and the horizontal size of the cell can be estimated using, for example, the method discussed above based on applying a bandpass filter to the square of the fluorescence data (step 3). In step (4), a ratio of the estimates of the cell's vertical and horizontal sizes is determined and compared with a predefined threshold to make a sorting decision with regard to that cell. For example, in some cases, if the ratio exceeds the threshold, a positive sorting decision can be made with respect to that cell.

The above sorting method based on a cell's aspect ratio can be used, e.g., in cell cycle analysis, DNA analysis, etc.

Figure 23A:
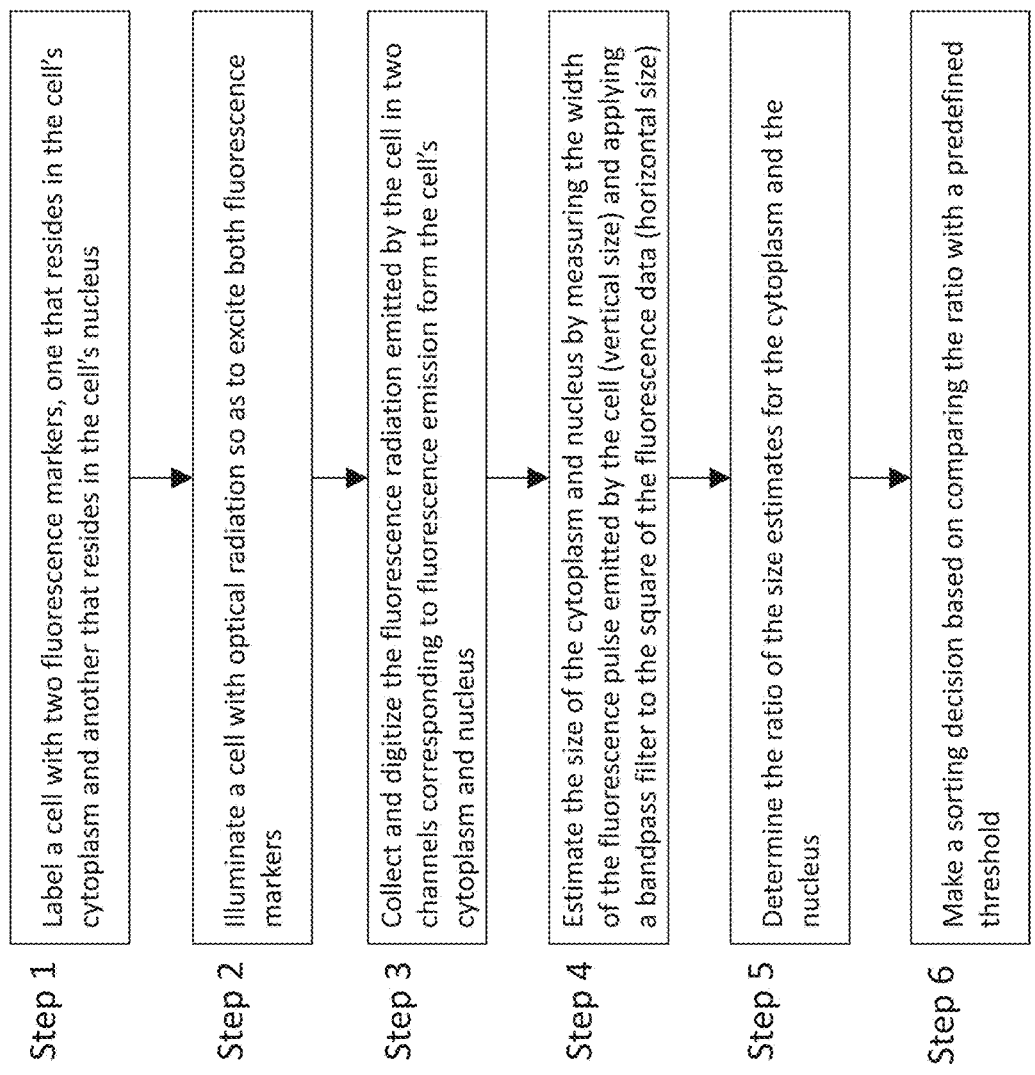
FIG. 23A is a flow chart depicting various steps in a method for estimating the ratio of the size of a cell's nucleus and the cell's cytoplasm.

In another aspect, a method of determining the ratio of the size of a cell's nucleus relative to the size of its cytoplasm is disclosed. In some embodiments, such a ratio can be employed to make a sorting decision. With reference to the flow chart of FIG. 23A, in one such embodiment, a cell is labeled (e.g., stained) with two fluorescence markers, one of which would reside on the cell's membrane (boundary of the cytoplasm) and the other can permeate the cell membrane to enter the cytoplasm and stain the cell's nucleus (e.g., via internal machinery of the cell) (step 1). Some examples of fluorescence markers that would bind to the cell membrane include any antibody tagged with a fluorophore that binds to a membrane protein, such as anti-CD45-FITC, or anti-EpCAM-PE. Other common surface proteins that can be employed for binding a fluorescence marker to the cell membrane include, for example, CD3, CD4, CD8, etc. Some examples of suitable nuclear fluorescence stains include, without limitation, Propidium Iodide, SYTO16, 7-AAD, and DAPI.

The cell is then illuminated with radiation so as to excite both types of fluorescence markers (step 2), and the emitted fluorescence is detected and digitized in two channels corresponding to fluorescence emission from the cell membrane and from its nucleus (step 3). The fluorescence data corresponding to the cell membrane is used, for example, in a manner discussed above, to obtain an estimate of the size of the cytoplasm, and the fluorescence data corresponding to the nucleus is used to obtain an estimate of the nucleus size (step 4). For example, the width of the fluorescence or light scatter pulse in each channel can be employed, e.g., in a manner discussed above, to estimate the cell size along one dimension (i.e., along the direction of flow). Further, the lateral size of the cytoplasm or the nucleus can be estimated by applying a bandpass filter to the square of the fluorescence data in the respective channel in a manner discussed above. The result of integrating this bandpass-filtered data provides a value to compare with a predefined threshold in order to sort cells that are larger or smaller than the threshold. Further, the size estimates of the cell in the two dimensions can be combined, e.g., by obtaining the square root of the sum of the squares of the vertical and horizontal size estimates, to arrive at a sort decision based upon an estimate of the total cell size.

In step (5), the ratio of the size estimates for the cytoplasm and the nucleus is obtained, e.g., the ratio of the sizes in the vertical or the horizontal direction, or the ratio of the combined sizes.

Figure 23B:
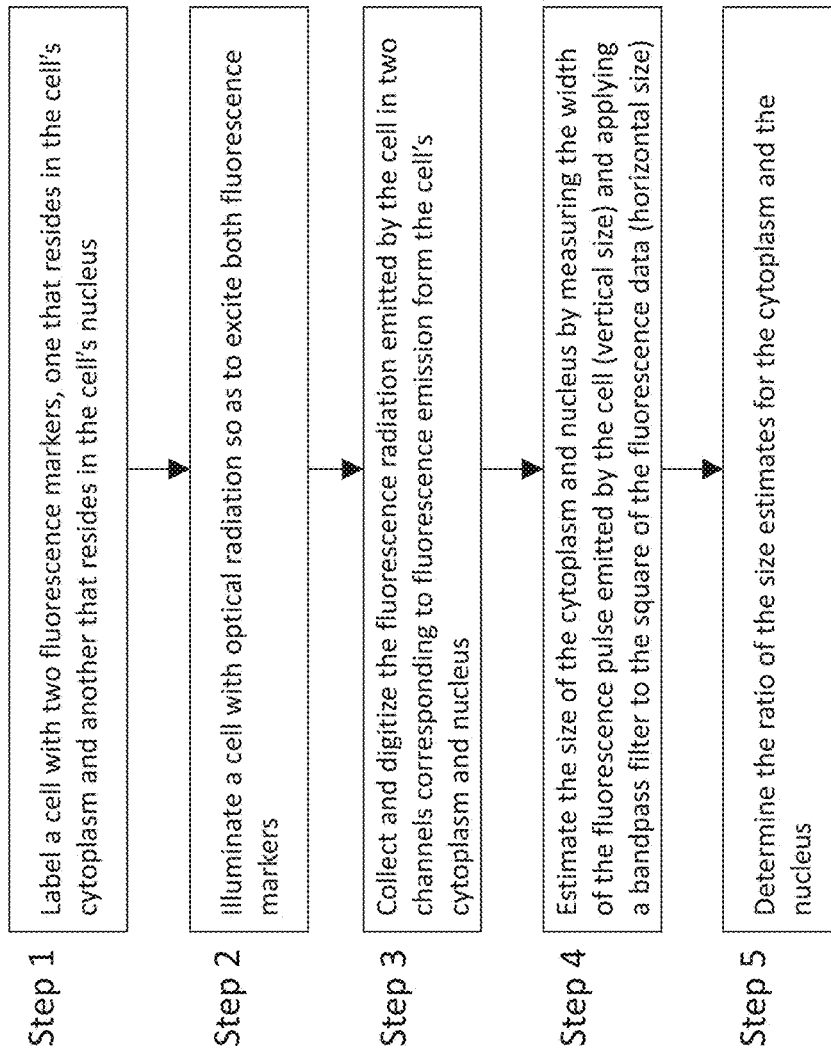
FIG. 23B is a flow chart depicting various steps in a method for sorting cells based on the estimated ratio of the size of a cell's nucleus and the cell's cytoplasm.

With reference to the flow chart of FIG. 23B, in some embodiments, the ratio of the size of the cell's nucleus relative to the size of its cytoplasm, which can be determined, e.g., in a manner discussed above and represented in steps (1)-(5) of the flow chart of FIG. 23B, can be used to make a sorting decision. For example, the ratio can be compared with a predefined threshold to make a sorting decision (step 6). By way of example, if the ratio exceeds the threshold, a positive sorting decision is made (i.e., the cell is selected).

By way of example, the above sorting method based on the nuclear-to-cytoplasm size ratio can be used in classification of circulating tumor cells.

In another aspect, a method of estimating cellular granularity of fluorescent radiation emitted from cells (fluorescence punctateness) is disclosed, which in some embodiments can be used for sorting the cells. In other words, a sorting decision can made based on whether the emitted fluorescent radiation from a cell can be characterized as emanating from a diffuse intracellular distribution of emitting centers, or can be characterized as emanating from emitting centers that are not diffusely distributed within the cell.

Figure 24A:
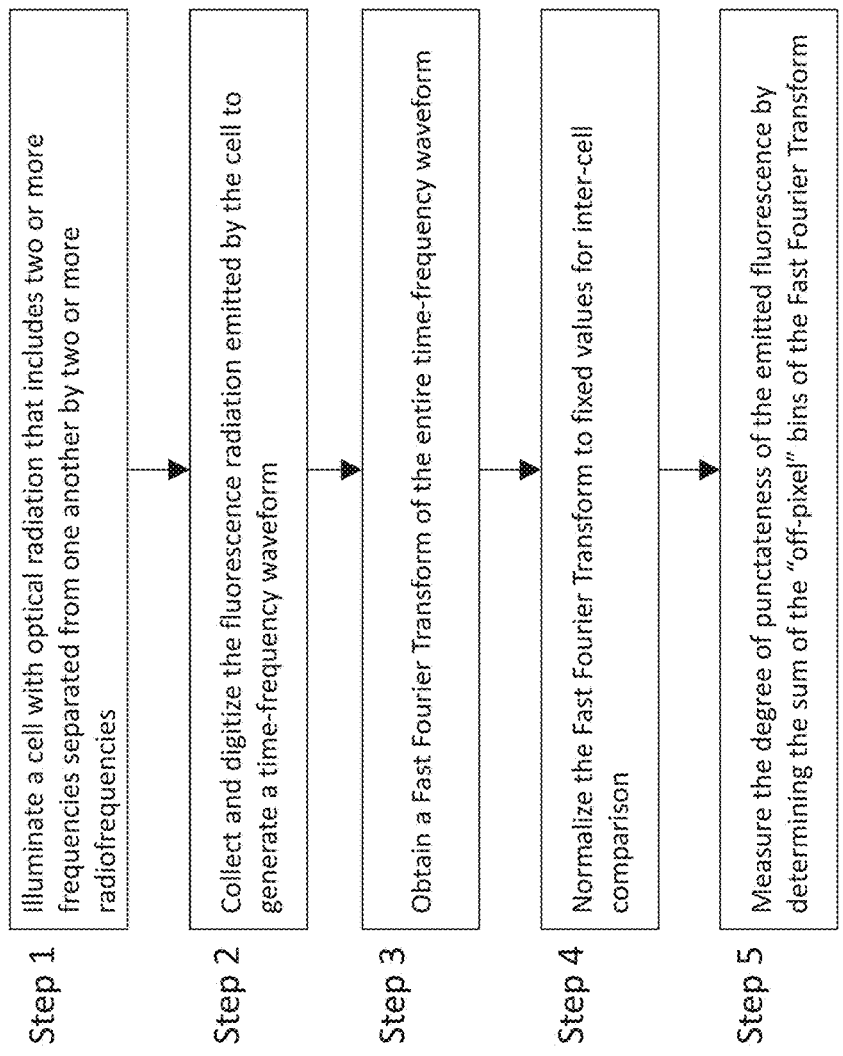
FIG. 24A is a flow chart depicting various steps in a method for estimating cellular granularity of fluorescence radiation emitted from cells.
Figure 25:
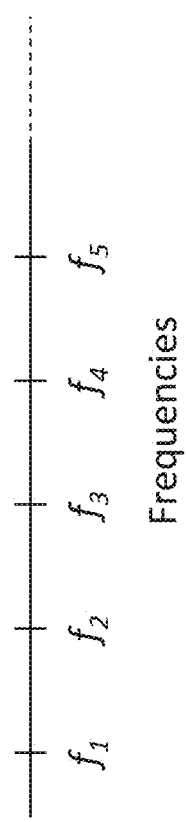

More specifically, with reference to the flow chart depicted in FIG. 24A, in one embodiment, a cell having one or more exogenous and/or endogenous fluorescence markers is illuminated with optical radiation having two or more optical frequencies separated from one another by one or more radiofrequencies so as to elicit fluorescence radiation from the marker(s) (step 1). Similar to the previous embodiments, in some cases, the optical beam can include a plurality of angularly or spatially separated beamlets, each of which has a radiofrequency shift relative to another. By way of example, with reference to FIG. 25, in an illustrative, exemplary embodiment the optical radiation beam can include modulation frequencies $f_1$, $f_2$, $f_3$, $f_4$, $f_5$, which can span, e.g., from 10 MHz ($f_1$) to 15 MHz ($f_5$) with a separation of 0.5 MHz. As discussed in more detail below, the punctateness of the emitted fluorescence radiation can be estimated by the extent in which the emitted fluorescence radiation exhibits modulation frequencies other than those employed to modulate the optical beam (e.g., other that $f_1$, $f_2$, $f_3$, $f_3$, $f_5$, in this embodiment). The other frequencies, which can be frequencies between the frequencies used to modulate the optical beam, are herein referred to as "off-pixel frequencies." In other words, the "leakage" of fluorescence power into off-pixel frequencies is indicative of the degree of punctateness of the emitted fluorescence; the more the leakage the more is the punctateness of the emitted fluorescence.

Referring again to the flow chart of FIG. 24A, the fluorescent radiation can be collected and digitized to generate a time-frequency waveform (step 2). In step (3), a Fourier transform, e.g., a Fast Fourier Transform (FFT), of the entire waveform is obtained. Subsequently, the generated FFT is normalized to fixed values for inter-cell comparison (step 4), e.g., by dividing the time-domain waveform by its maximum value and then re-scaling the waveform by a desired constant. The sum of the "off-pixel" bins of the FFT (i.e., the bins corresponding to frequencies between the modulation frequencies present in the illuminating optical radiation) is determined (step 5). The sum is indicative of the degree of "leakage" of fluorescence power to off-pixel frequencies, and hence a measure of the degree of punctateness of the emitted fluorescent radiation.

Figure 24B:
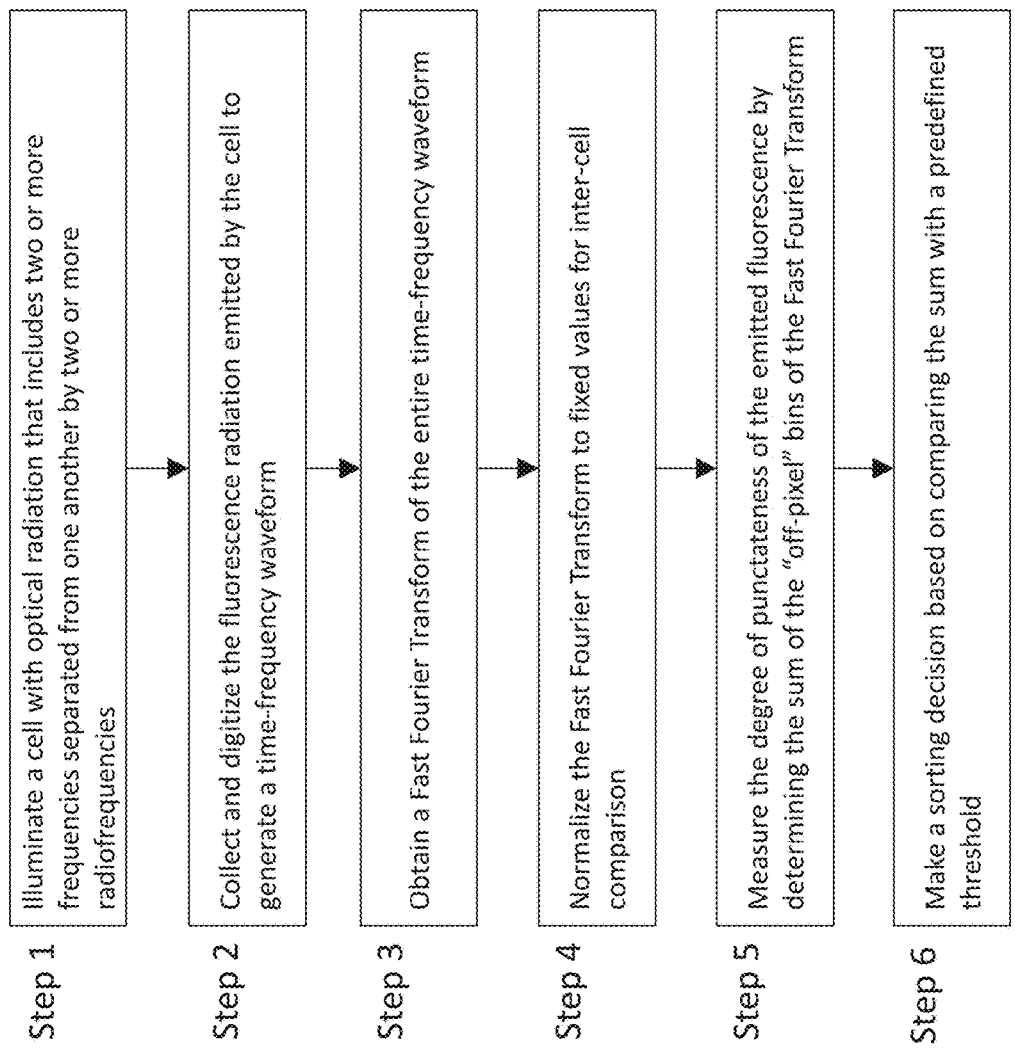
FIG. 24B is a flow chart depicting various steps in a method for sorting cells based on estimating cellular granularity of fluorescence radiation emitted from the cells, FIG. 25 schematically shows modulation frequencies used to modulate an optical beam employed in the method described in the flow chart of FIG. 24 for eliciting fluorescence radiation from the cells, FIG. 26 schematically depicts a sorting system that incorporates the present teachings for sorting cells, FIG. 27 schematically depicts an exemplary implementation of the analysis/control module employed in the system of FIG. 26.

With reference to FIG. 24B, in some embodiments, the measure of the degree of punctateness of the emitted fluorescent radiation, which can be determined in a manner discussed above and represented in steps (1)-(5) of the flow chart of FIG. 24B, can be used for sorting the cells. In particular, in step (6), the sum of the "off-pixel" bins of the FFT, which is indicative of the degree of "leakage" of fluorescence power to off-pixel frequencies, can be compared with a predefined threshold to make a sorting decision. For example, when it is desired to sort cells exhibiting a relatively high degree of fluorescence punctateness, a cell is sorted (selected) if the sum is greater than the threshold. Alternatively, when it is desired to sort cells exhibiting diffuse fluorescence, a cell is sorted if the sum is less than the threshold.

Such sorting of cells based on the analysis of the emitted fluorescent radiation can be employed in a variety of applications, such as spot counting, fluorescence in-situ hybridization (FISH), intracellular transport and localization, and droplet-based single-cell analysis.

Figure 26:
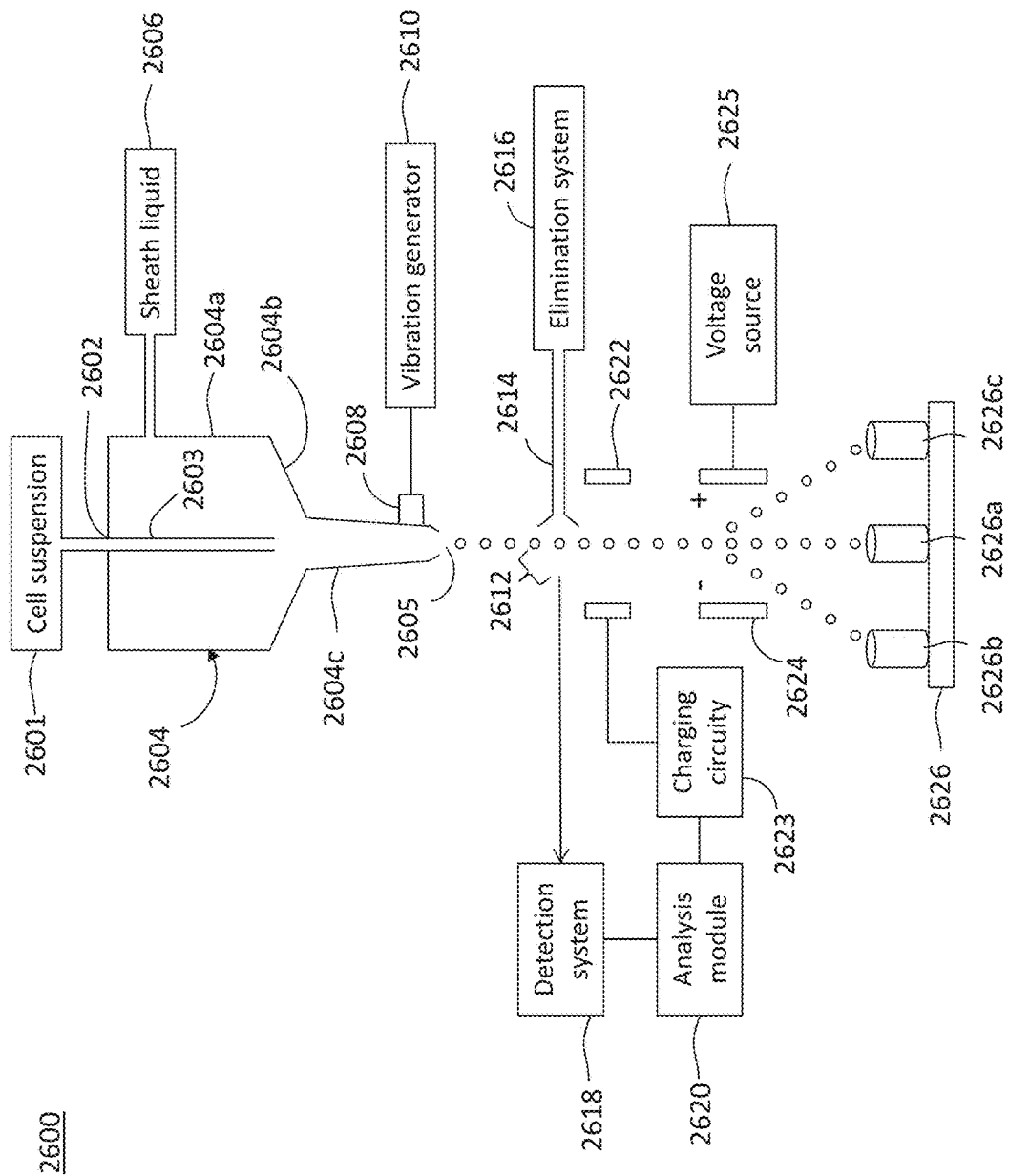

The above methods for making sorting decisions for particles (e.g., cells flowing in a flow cytometry system) can be implemented in a variety of ways. By way of example, FIG. 26 schematically depicts an exemplary system 2600 for sorting cells, which can employ the present teachings for making a sorting decision. The system 2600 can include a container 2601 for storing a suspension fluid in which a plurality of cells is suspended. The cell suspension container 2601 is fluidly coupled via an inlet 2602 to a sample conduit 2603, which can be formed, for example, of a rigid metal such as stainless steel. The sample conduit 2603 is disposed within a vessel 2604 that includes an upper cylindrical portion 2604a that extends, via a tapered portion 2604b, to a lower cylindrical portion 2604c having a smaller diameter, which includes a nozzle 2605 at a distal end thereof. The vessel 2604 is fluidly coupled to a sheath fluid source 2606. An acoustic vibrator 2608 (e.g., a piezoelectric driver) is coupled to the nozzle and is configured to cause vibration of the nozzle when energized by a generator 2610. By way of example, the vibration frequency can be about 60 kHz, though other vibration frequencies can be also used.

In use, the suspension fluid stored in the container 2601 is introduced via the inlet 2602 into the conduit 2603. A thin flow of the fluid containing cells that exits the container 2603 is entrained by the sheath fluid and is carried to the nozzle 2605. The vibratory motion of the nozzle can be configured in a manner known in the art to split the flow through the nozzle into a plurality of droplets D each of which contains a single cell particle. At least some of the cells are associated with one or more endogenous and/or exogenous fluorophores, which can emit fluorescent radiation in response to illumination by an excitation radiation. A wide range of fluorophores can be used. In some cases, a fluorophore can be attached to an antibody that recognizes a target (e.g., a receptor) on a cell. In some cases, a fluorophore can be attached to a chemical entity that has an affinity for the cell membrane or another cellular structure, e.g., the cell's nucleus. Further, in some cases, a cell can be labelled with a combination of different fluorophores.

With continued reference to FIG. 26, as each cell passes through an interrogation region 2612 it is illuminated by a laser beam 2614 generated by an illumination system 2616 to elicit fluorescent radiation from one or more fluorophores associated with the cell. As discussed above, the laser beam can include a plurality of optical frequencies that are shifted relative to one another by one or more radiofrequencies. By way of example, the optical beam can be in the form of a plurality of angularly or spatially separated beamlets having radiofrequency shifts relative to one another. The fluorescent radiation emitted from the cell can be detected by a detection system 2618, which can include one or more photodetectors. The detected fluorescent can be analyzed by an analysis module 2620, in a manner discussed above, to make a sorting decision regarding that cell.

By way of example, the illumination the detection systems can be those discussed above, e.g., in connection with FIGS. 1-12. It should, however, be understood that the practice of the present teachings for sorting particle is not limited to the use of any particular illumination and detection system. Rather, a variety of different systems can be employed so as long as they provide the requisite data (e.g., fluorescence and/or scatter data) for use in the above methods for making sorting decisions.

Referring again to FIG. 26, the system 2600 further includes a charging collar 2622, which is energized by a charging circuity 2623, which is in turn under the control of the analysis module 2620. The charging collar can impart a positive, or a negative charge to a cell droplet as it passes through the collar. Alternatively, the collar can allow a cell droplet to pass through without imparting a charge thereto.

More specifically, the analysis module 2620 can employ the above teachings to make a sorting decision regarding a cell. Based on that decision, the analysis module can determine whether the cell droplet needs to be charged, and if so, which charge polarity should be imparted to the cell. The analysis module can then control the charging circuity 2623 to impart, via the collar 2622, the requisite charge to the cell droplet. The cell then passes through a gap between a pair of deflection plates 2624, which are disposed downstream of the collar 2622. A voltage source 2625 applies a voltage to at least one of the plates 2624 to establish an electric field between the plates. The electric field can deflect the path of the negative and positive cell droplets along different directions so that they can be collected, respectively, by tubes 2626b and 2626c of the cell collector 2626. The cells that are not electrically charged by the collar 2622 are not deflected and are captured by the tube 2626a of the cell collector.

Figure 27:
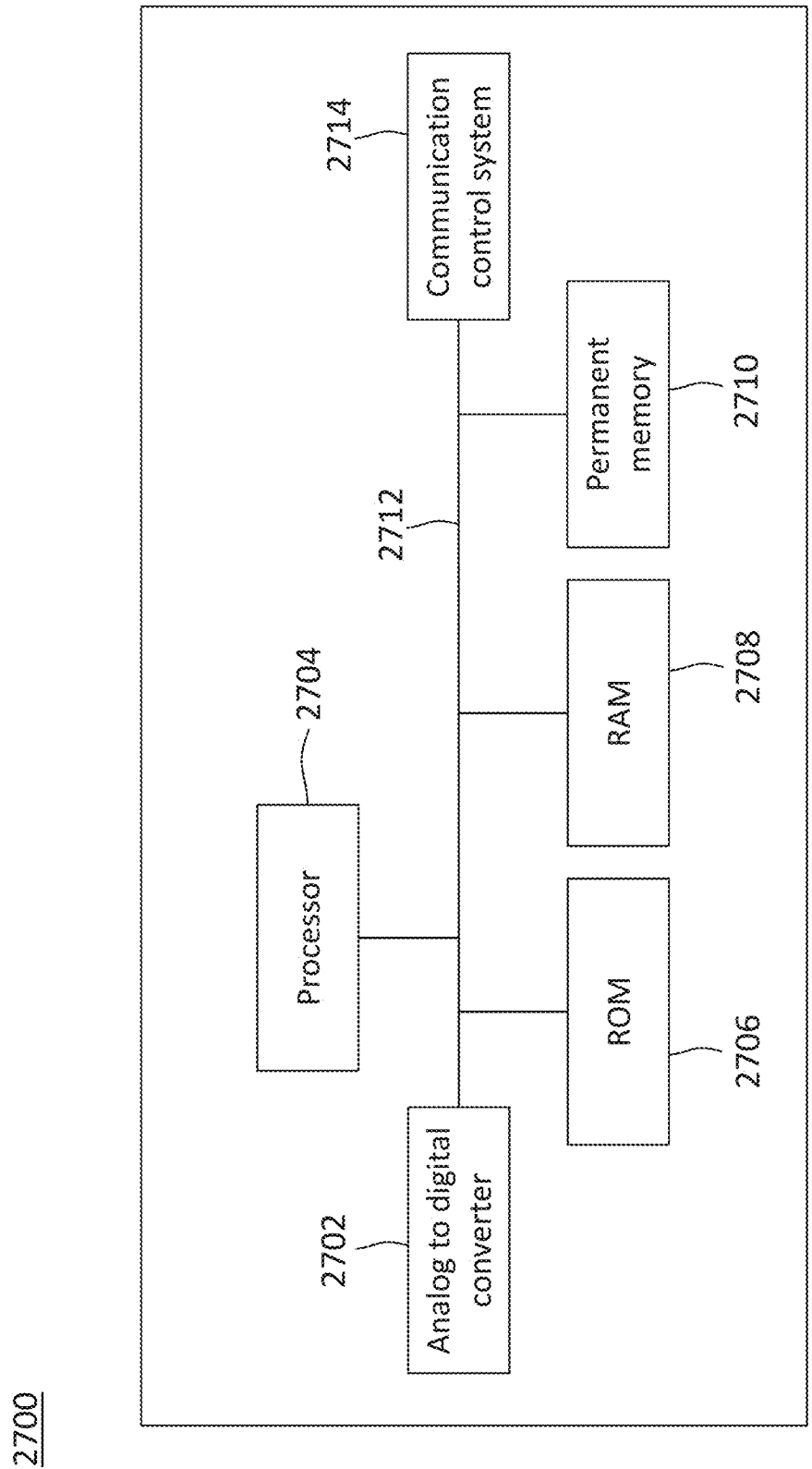

The analysis/control modules discussed herein, such as the analysis/control module 2620, can be implemented in a variety of different ways in hardware, firmware and/or software using techniques known in the art and in accordance with the present teachings. By way of example, FIG. 27 schematically depicts an exemplary implementation 2700 of the analysis/control module 2620, which includes an analog-to-digital converter 2702 for receiving fluorescence signal(s) from the detection system 2618 and digitizing the signal(s) to generate digitized fluorescence data. The analysis/control module 2700 can further include a processor 2704 for processing the fluorescence data in accordance with the present teachings to arrive at a sorting decision regarding a cell under interrogation. The analysis/control module 2700 can also include ROM (read only memory) 2706, RAM (random access memory) 2708 and permanent memory 2710. A communication bus 2712 facilitates communication among various components of the analysis module. The memory modules can be used to store instructions for analyzing the fluorescence signal(s) and the analysis results. For example, in some embodiments, instructions for analyzing the fluorescence data to arrive at a sorting decision in accordance with the present teachings can be stored in the ROM 2706. The processor 2704 can employ these instructions to operate on the digitized fluorescence data stored in RAM 2708 so as to determine a sorting decision. In some embodiments, the processor can be implemented as an ASIC (application specific integrated circuit) that is configured to perform the instructions according to the present teachings for operating on fluorescence data to arrive at a sorting decision. In this embodiment the analysis/control module 2700 can further include a communication/control module 2714 for sending appropriate signals to the charging circuitry based on the sort decision so as to impart suitable charge to a cell under interrogation.

As discussed above, the methods according to the present teachings operate on temporal fluorescence data to arrive at a sort decision for a particle (e.g., a cell) without the need to form a pixel-by-pixel fluorescence image of the cell. This in turn allows sorting cells with a low latency, e.g., less than about 100 microseconds, which in turn allows sorting cells at a high rate. For example, the sorting methods according to the present teachings can allow sorting cells at a rate of equal to or greater than 1000 cells per second, e.g., in a range of about 1000 to about 100,000 cells per second.

Though not limited to any particular illumination or detection technology, as noted above, in some embodiments the cell sorting methods according to the present teachings can be effectively used in flow cytometry systems that employ frequency domain multiplexing to excite a row of pixels, each "tagged" at a unique radiofrequency generated, for example, by beating of two frequency-offset baser beams. Using frequency-domain multiplexing, fluorescent (or scattered) radiation from hundreds of pixels in a single row of an image can be detected and read out using, for example, a single photomultiplier tube (PMT) for each fluorescent color or scattered direction. Since the excitation of each pixel in a row of the image is modulated at a unique beat frequency, the pixel rate scales with the total RF bandwidth of the system, which can provide shot noise-limited sensitivity at pixel rates of more than 100 MHz. As discussed above, the sorting methods according to the present teachings can employ the image data, which is encoded in a time-frequency format, to perform sorting decisions without actually computing the image.

Further, the above system can be employed to sort particles (e.g., cells) based on the scattered radiation emanating from the particles in response illumination. The scattered radiation can be detected and analyzed, e.g., in a manner discussed above, to arrive at a sort decision.

By way of further examples, the following U.S. patents provide information regarding sorting systems that can be modified in accordance to the present teachings to practice the sorting methods and systems disclosed herein: U.S. Pat. No. 3,380,584 entitled "Particle Separator," U.S. Pat. No. 9,034,259 entitled "Flow Cytometer and Flow Cytometry," and U.S. Pat. No. 7,417,734 entitled "System and Process for Sorting Biological Particles," each of which is herein incorporated by reference in its entirety.

By way of further elucidation, Appendix A provides additional information regarding various aspects of the present teachings.

Those having ordinary skill in the art will appreciate that various changes can be made without departing from the scope of the present teachings. In particular, various features, structures, or characteristics of embodiments discussed above can be combined in a suitable manner. For example, the detection systems discussed in connection with one embodiment may be used in another embodiment.

Appendix A

As discussed above, in some embodiments, two or more beamlets with a radiofrequency amplitude modulation illuminate a sample at spatially-distinct locations. The interaction between the sample and each beamlet can produce optical at least one of scattered, transmission, and fluorescent emission signals, each of which is amplitude-modulated with the beamlet's corresponding radiofrequency. The collected signal can be represented as the sum of the contributions from each modulated beamlet:

$$S(t)=\Sigma_i P_i(t)\cdot(1+A_m \cos(\omega_i t+\phi_i)) \quad \text{Eq. (3)}$$

where S(t) represents the collected signal, $P_i(t)$ represents the time-dependent scattered, transmission, or fluorescent emission signal associated with the ith beamlet, $A_m$ represents the modulation depth of the beamlet, and $\omega_i$ and $\phi_i$ represent the angular frequency and phase of the radiofrequency modulation of the beamlet, respectively. An image representation of the particle can be derived by assigning each beamlet to a different column of the image, and each moment in time to a different row of the image. This image representation is connected to the collected signal via the Fourier Transform:

$$\text{Im}(x, y)=R\cdot W\cdot F\cdot S(t) \quad \text{Eq. (4)}$$

where F is a matrix implementing the short-time Fourier Transform, W is a matrix that maps Fourier components to image pixels, and R is a matrix that performs any desired linear image-domain post-processing such as filtering, background subtraction, and vignette correction. Any linear feature of a particle can be represented by a matrix multiplication on an image. Therefore, for a matrix M that computes any desired linear feature, the feature can be computed directly, i.e., without the need to first compute an image, from collected signals via:

$$M\cdot\text{Im}(x, y)=M\cdot R\cdot W\cdot F\cdot S(t)=Q\cdot S(t) \quad \text{Eq. (5)}$$

$$Q=M\cdot R\cdot W\cdot F \quad \text{Eq. (6)}$$

where Q is a matrix representing the transformation from the present particle representation to the desired linear feature. Hence, any linear feature can be computed by initially computing the matrix Q, e.g., offline in a pre-processing step, then performing a dot product as indicated in Eq. (5), e.g., online, to extract the desired feature. In many embodiments, for all features, it is desired to also subtract the contribution of background signal to the feature. This process can be summarized as follows:

Compute: $Q=M\cdot R\cdot W\cdot F$

Compute: $Q_{bkg}=M\cdot R\cdot W_{bkg}\cdot F$

While data is being collected:
  If a particle is detected:

Compute: $D=Q\cdot S(t)$

Else:

Compute: $D_{bkg}(i)=Q_{bkg}\cdot S(t)$

Compute: $D_{bkg}=\text{mean}(D_{bkg}(i))$

Yield: $D-D_{bkg}$

Figure 28:
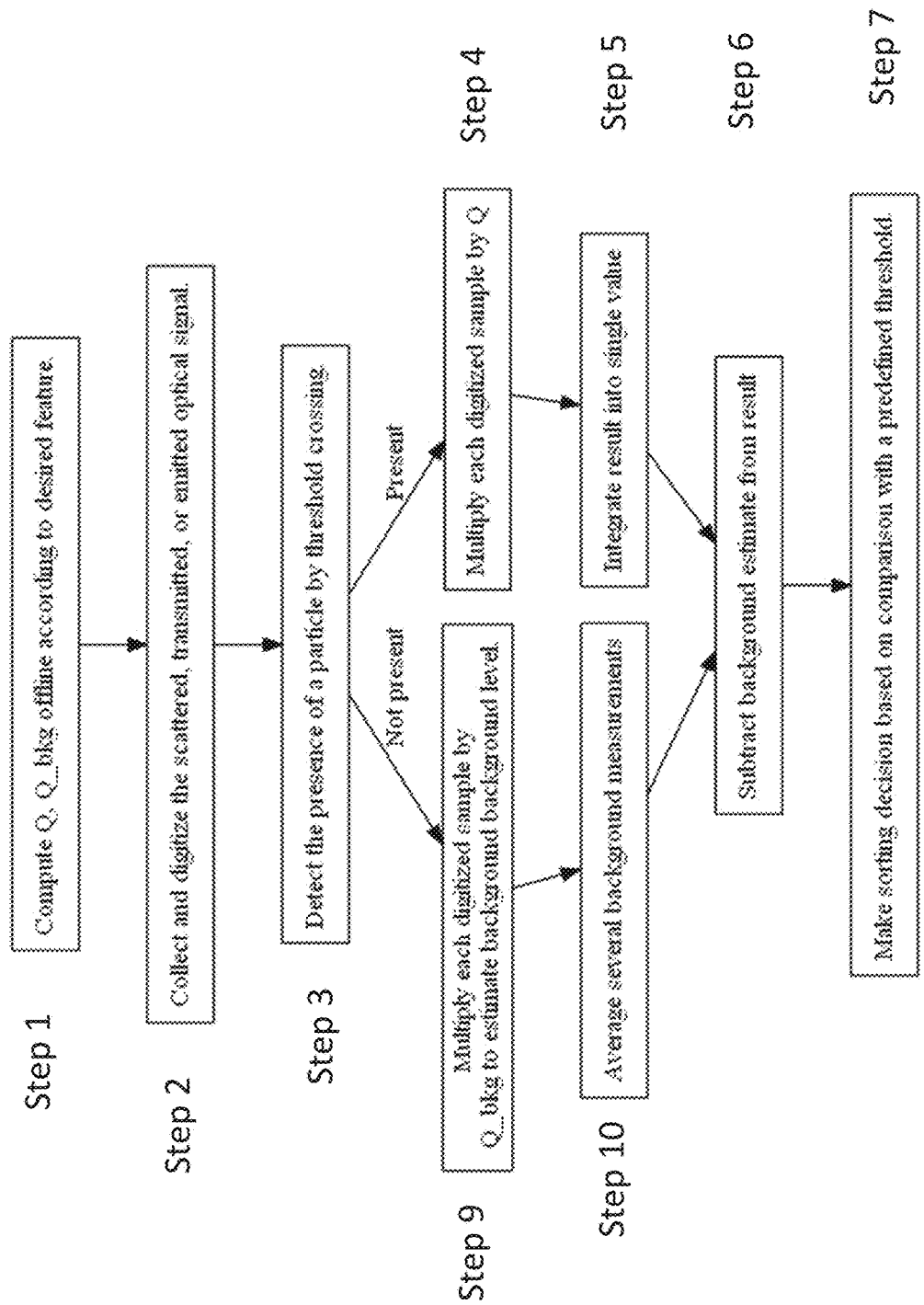
FIG. 28 is a flow depicting various steps in an exemplary method for determining a characteristic or a particle and using that characteristic to make a sorting decision in accordance with an embodiment.

As discussed above, in some embodiments, one or more computed features of a particle can be employed for making a sorting decision regarding that particle. By way of a further example, FIG. 28 shows a flow chart depicting various steps in such a sorting method. In an initial step (1), the above Q, and $Q_{bkg}$ matrices can be computed based on a desired particle feature (characteristic). Subsequently, scattered, transmitted or emitted optical signal, e.g., from a flow cell of a flow cytometer illuminated with radiofrequency-modulated optical radiation, can be collected and digitized (step 2). The signal can be compared with a threshold crossing to determine whether the signal is from a particle, i.e., whether a particle was present (step 3). If it is determined that a particle was present, each digitized sample signal is multiplied by Q (step 4) followed by integrating the result into a single value (step 5). A background signal is subtracted from the integrated value (step 6) to obtain an estimate of the desired feature (characteristic) of the particle. A sorting decision can be made via comparison of the estimate of the feature with a threshold (step 7). With continued reference to the flow chart of FIG. 28, one or more digitized signals obtained in absence of a particle, can be multiplied by $Q_{bkg}$ (step 8), and several background measurements can be averaged to obtain the background estimate employed in the step (6).

In some embodiments, various moments of a received signal can be used to obtain information about the spatial distribution of scattered, transmitted, or emitted radiation. Image moments are a class linear image features representing the weighted sum of pixels according to their distance from an arbitrary origin, taken to some arbitrary power:

$$M_{m,n} = \Sigma(x-\bar{x})^m(y-\bar{y})^n \text{Im}(x, y) = M \cdot \text{Im}(x, y) \quad \text{Eq. (7)}$$

Each image moment encodes different information about the spatial distribution of scattered, transmitted, or emitted light. Higher-order moments weigh pixels more according to their distance from the origin, with each moment providing different information about the distribution of signal. In various embodiments, all of these features can be computed directly from the measured signal S(t) by pre-computing an appropriate Q.

Spatial Fourier components can be computed in the same way, with M defined as follows:

$$M(u, v) = \exp(-j2\pi(ux+vy)) \quad \text{Eq. (8)}$$

The desired components can be selected before an experiment, and a separate Q can be pre-computed for each one. By of example, Fourier components can be used to determine if a particle is in focus of illuminating radiation.

Some image features involve nonlinear transformations on the data prior to feature extraction. For a subset of such features, it is possible to represent them as nonlinear combinations of linear features. Computing such features can involve first computing multiple features as in the previous section in parallel, then combining the results in a nonlinear way. There are many useful image features that can be expressed by nonlinear combinations of image moments. For example, the center of mass of the pixels can be calculated by the ratio of the first- and zero-order moments:

$$\text{Center of Mass} = \frac{M_{1,0}}{M_{0,0}} \quad \text{Eq. (9)}$$

Several other particle characteristics can be represented this way. A non-exhaustive list is in Table 1 below.

Figure 29:
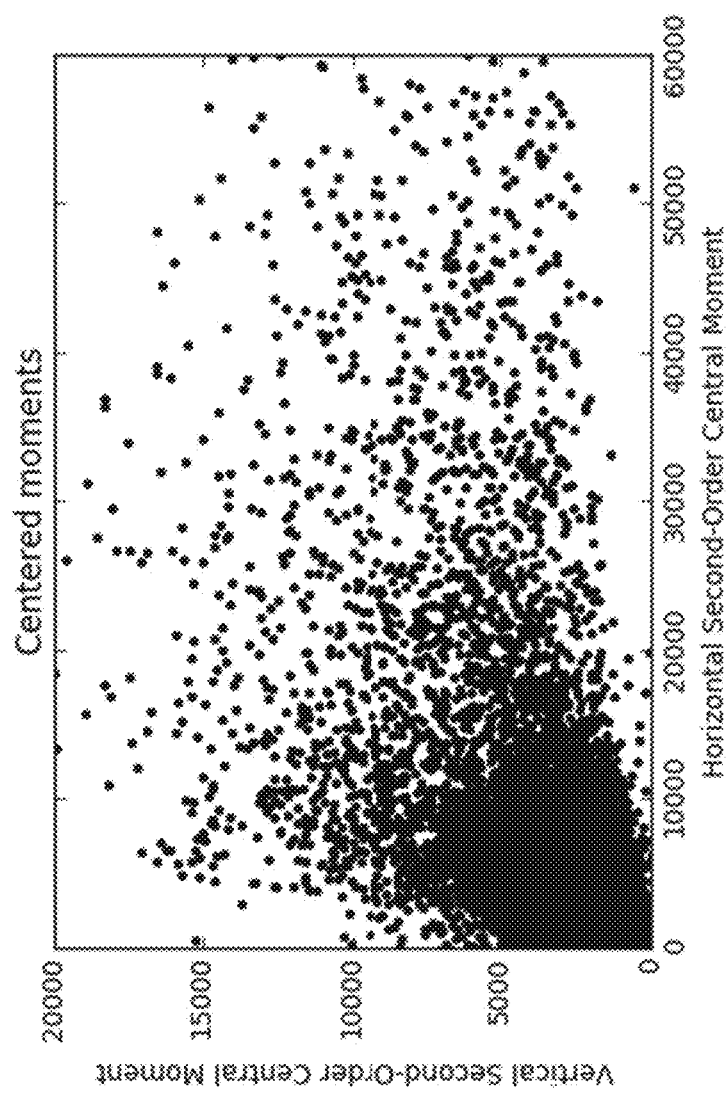
FIG. 29 is a scatter plot of vertical and horizontal second-order central moments for a plurality of cells.

In some embodiments, central second-order moments can be used to discriminate doublets. Particles with high second-order moments in scattered or transmitted light signals indicate a larger distribution of signal. By way of example, FIG. 29 shows a scatter plot corresponding to horizontal and vertical central moments of a plurality of blood cells.

Colocalization and Similarity

In some embodiments, similarity between a particle and a reference can be computed the same way as co-localization. In the co-localization case, the two waveforms correspond to different detectors looking at the same particle; in the similarity case, the two waveforms correspond to the same detector looking at two different particles. An exemplary algorithm for detecting similarity between a particle and a reference is summarized below:

Let R represent the waveform corresponding to a reference particle, Filt be a high-pass or band-pass filter that passes only modulated frequencies, and N be the number of pixels in an image representation of the reference particle. The algorithm will then include:

Compute $$\bar{R} = \frac{M_{0,0}(R)}{N},$$

Compute $R'=\text{Filt}(R)$,

Compute $R_2 = \|R'\|^2$,

For each incoming waveform S corresponding to a particle under study:

Compute $$\bar{S} = \frac{M_{0,0}(S)}{N}$$

Compute $S'=\text{Filt}(S)$

TABLE 1

| Extracted Feature | Nonlinear combination of linear features |
|---|---|
| Center of Mass | $\dfrac{M_{1,0}}{M_{0,0}}$ |
| Orientation | $\dfrac{1}{2}\arctan\dfrac{2\left(M_{1,1} - \dfrac{M_{1,0}M_{0,1}}{M_{0,0}}\right)}{M_{2,0} - \dfrac{M_{2,0}^2}{M_{0,0}} - M_{0,2} + \dfrac{M_{0,2}^2}{M_{0,0}}}$ |
| Eccentricity | $\dfrac{M_{2,0} - \dfrac{M_{2,0}^2}{M_{0,0}^2} + M_{0,2} - \dfrac{M_{0,2}^2}{M_{0,0}^2} - \sqrt{4\left(M_{1,1} - \dfrac{M_{1,0}M_{0,1}}{M_{0,0}^2}\right)^2 + \left(M_{2,0} - \dfrac{M_{2,0}^2}{M_{0,0}} - M_{0,2} + \dfrac{M_{0,2}^2}{M_{0,0}}\right)^2}}{M_{2,0} - \dfrac{M_{2,0}^2}{M_{0,0}^2} + M_{0,2} - \dfrac{M_{0,2}^2}{M_{0,0}^2} + \sqrt{4\left(M_{1,1} - \dfrac{M_{1,0}M_{0,1}}{M_{0,0}^2}\right)^2 + \left(M_{2,0} - \dfrac{M_{2,0}^2}{M_{0,0}} - M_{0,2} + \dfrac{M_{0,2}^2}{M_{0,0}}\right)^2}}$ |
| Central Moments (Second-order) | $M_{2,0} - \dfrac{M_{1,0}^2}{M_{0,0}}, M_{0,2} - \dfrac{M_{0,1}^2}{M_{0,0}}$ |

Compute $D = S'\cdot R'$

Compute $S_2 = \|S'\|^2$

Return $$\frac{D - \overline{S}\overline{R}N}{(R_2 - \overline{R}^2 N)(S_2 - \overline{S}^2 N)}$$

as a measure of the similarly of the particle with the reference particle.

What is claimed is:

1. A method for sorting cells of a biological sample in a flow cytometry system, comprising:

illuminating with a laser the biological sample with radiation having two or more optical frequencies which differ from one another by one or more radiofrequencies to elicit fluorescent radiation from cells in the biological sample, detecting the fluorescent radiation with a photodetector to generate temporal fluorescence data, and processing said temporal fluorescence data to arrive at a sorting decision regarding said cells in the biological sample with a latency equal to or less than about 100 microseconds.

2. A method for sorting cells of a biological sample in a flow cytometry system, comprising:

illuminating with a laser the biological sample with an optical radiation beam having at least two optical frequencies which differ from one another by a radiofrequency to elicit fluorescent radiation from cells in the biological sample, detecting the fluorescent radiation with a photodetector to generate temporal fluorescence data, and processing said temporal fluorescence data to arrive at a sorting decision regarding said cells in the biological sample.

3. The method of claim 2, wherein said processing step comprising operating on said fluorescence data to obtain an estimate of a characteristic of the cells in the biological sample and making said sorting decision based on said estimate.

4. The method of claim 3, wherein said processing step comprising analyzing at least one beat frequency associated with said radiofrequency in said temporal fluorescence data to obtain said estimate of a characteristic of the cells in the biological sample.

5. The method of claim 3, wherein said characteristic is associated with an internal organelle.

6. The method of claim 2, wherein said processing step arrives at said sorting decision without generating a fluorescence image based on said fluorescence data.

7. The method of claim 2, wherein said characteristic of the cells in the biological sample comprises any of a dimensional size of the cell, a ratio of sizes of the cell in along two different dimensions, co-localization of fluorescence radiation emitted by two or more markers associated with the cell, a ratio of sizes of the cell's cytoplasm and nucleus, a degree of punctateness of fluorescent radiation emitted from the cell, a measure of the spatial distribution of the fluorescent radiation, a measure of location or orientation of the cell, a measure of the eccentricity of the cell, a measure of the cell's similarity to a reference cell, a combination of one or more spatial Fourier components of the cell, a measure of the degree to which the cell lies in a focal point of the illuminating radiation.

8. The method of claim 2, wherein said processing step comprises a latency associated with arriving at said sorting decision that is less than about 100 microseconds.

9. The method of claim 8, wherein said latency is less than about 20 microseconds.

10. The method of claim 2, wherein said optical beam is configured such that an optical frequency at which each of a plurality of spatial locations within a cell in the biological sample is illuminated corresponds to a different one of said different optical frequencies.

11. The method of claim 2, wherein said cells in the biological sample are stained with at least two fluorescence markers and said optical radiation is configured to elicit fluorescent radiation from said markers.

12. The method of claim 11, further comprising collecting and digitizing fluorescent radiation emanated from said markers to generate temporal fluorescence waveforms each corresponding to one of said markers.

13. The method of claim 12, wherein said processing step comprises operating on said fluorescence waveforms to obtain a measure of co-localization of said fluorescence signals corresponding to said fluorescence markers and making said sorting decision based on said co-localization measure.

14. The method of claim 13, wherein said step of operating on said waveforms comprises applying a high-pass or a band-pass filter to at least one of said waveforms to generate at least one filtered waveform followed by point-wise multiplication of said waveforms to generate a resultant multiplicative waveform, integrating said filtered waveform to obtain an integrated value, and comparing the integrated value with a predefined threshold to obtain said measure of co-localization.

15. The method of claim 14, wherein said step of operating on said waveforms comprises applying a high-pass or a band-pass filter to at least one of said waveforms to generate at least one filtered waveform followed by point-wise multiplication of said waveforms to generate a resultant multiplicative waveform, integrating said multiplicative waveform to obtain an integrated value, subtracting a background value from the integrated value and scaling the resultant value by intensity to generate a finalized value, and comparing the finalized value with a predefined threshold to obtain said measure of co-localization.

16. The method of claim 2, wherein said processing step comprises operating on said fluorescence data to obtain an estimate of a size of cells in the biological sample and making said sorting decision based on said estimated cell size.

17. The method of claim 16, wherein said estimate of the cell size can be any of an estimate of the cell size in a direction of flow in the flow cytometry system and a lateral size of the cell.

18. The method of claim 17, further comprising estimating said cell size in the direction of flow based on a temporal duration of a pulse of fluorescent radiation emanated from the cell.

19. The method of claim 17, wherein the estimate of the lateral size of the cell is obtained by squaring the detected temporal fluorescence data, applying a bandpass filter to the squared fluorescence data, integrating the filtered data, and comparing the filtered data with a predefined threshold.

20. The method of claim 2, wherein said processing step comprises operating on said fluorescence data to obtain a ratio of the size of one or more cells in the biological sample along two different dimensions and utilizing said ratio to make the sorting decision.

21. The method of claim 2, further comprising: labeling cells in the biological sample with two fluorescence markers, wherein a first fluorescent marker couples to the cellular membrane and a second fluorescent marker couples to the nucleus.

22. The method of claim 21, wherein the optical radiation is configured to elicit fluorescent radiation from both of said markers, and wherein said detecting step comprises detecting the fluorescent radiation emanated from both markers in two different channels.

23. The method of claim 2, wherein said processing step comprises analyzing the detected fluorescent radiation in said channels to obtain an estimate of a dimensional size of the cytoplasm of one or more cells in the biological sample and the nucleus and making the sorting decision based on a ratio of said dimensional size estimates of the nucleus and cytoplasm.

24. The method of claim 2, further comprising obtaining a Fourier transform of said fluorescence data, and determining frequencies in the transform different from said radiofrequencies, obtaining a sum of Fourier transform values at said different frequencies, and comparing said sum with a predefined threshold to make the sorting decision.

* * * * *